United States Patent
Wandless et al.

(10) Patent No.: US 11,891,634 B2
(45) Date of Patent: Feb. 6, 2024

(54) PDE5A DESTABILIZING DOMAINS

(71) Applicant: The Board of Trustees of the Leland Stanford Junior University, Stanford, CA (US)

(72) Inventors: Thomas J. Wandless, Stanford, CA (US); Ling-Chun Chen, Stanford, CA (US); Yusaku Miyamae, Ibaraki (JP)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 692 days.

(21) Appl. No.: 16/625,644

(22) PCT Filed: Jun. 22, 2018

(86) PCT No.: PCT/US2018/039096
§ 371 (c)(1),
(2) Date: Dec. 20, 2019

(87) PCT Pub. No.: WO2018/237323
PCT Pub. Date: Dec. 27, 2018

(65) Prior Publication Data
US 2020/0123514 A1    Apr. 23, 2020

Related U.S. Application Data

(60) Provisional application No. 62/524,384, filed on Jun. 23, 2017.

(51) Int. Cl.
*C12N 9/00* (2006.01)
*C12N 15/62* (2006.01)
*C12N 15/10* (2006.01)
*C12N 9/16* (2006.01)
*C07K 14/435* (2006.01)

(52) U.S. Cl.
CPC .............. *C12N 9/16* (2013.01); *C07K 14/435* (2013.01); *C12N 15/1055* (2013.01); *C12N 15/62* (2013.01); *C12Y 301/04017* (2013.01); C07K 2319/70 (2013.01)

(58) Field of Classification Search
CPC ........ C12N 9/16; C12N 15/62; C07K 14/435; C12Y 301/04017
See application file for complete search history.

(56) References Cited

U.S. PATENT DOCUMENTS

| | | | |
|---|---|---|---|
| 11,241,485 B2 * | 2/2022 | Suri | A61K 38/2086 |
| 2005/0048573 A1 | 3/2005 | Artis et al. | |
| 2009/0215169 A1 | 8/2009 | Wandless et al. | |
| 2010/0034777 A1 | 2/2010 | Wandless et al. | |
| 2011/0039257 A1 * | 2/2011 | Binkowski | C12Q 1/66 435/8 |
| 2020/0101142 A1 * | 4/2020 | Suri | A61K 39/3955 |

FOREIGN PATENT DOCUMENTS

| WO | WO 2000/023091 A2 | 4/2000 |
|---|---|---|
| WO | WO 2007/142929 A2 | 12/2007 |
| WO | WO 2018/160993 A1 | 9/2018 |
| WO | WO 2018/237323 A1 | 12/2018 |

OTHER PUBLICATIONS

International Search Report from International Application No. PCT/US2018/039096, 5 pages, dated Oct. 4, 2018, application now published as International Publication No. WO2018/237323 on Dec. 27, 2018.

* cited by examiner

*Primary Examiner* — Maryam Monshipouri
(74) *Attorney, Agent, or Firm* — McDermott Will & Emery LLP; Judy M. Mohr; Peter Brunovskis

(57) ABSTRACT

Disclosed herein are systems, methods, and compositions for rapidly and reversibly destabilizing a target protein in vitro or in vivo, in the presence or absence of a cell-permeable, synthetic molecule or ligand.

2 Claims, 2 Drawing Sheets
Specification includes a Sequence Listing.

SEQUENCE LISTING

```
<160> NUMBER OF SEQ ID NOS: 77

<210> SEQ ID NO 1
<211> LENGTH: 875
<212> TYPE: PRT
<213> ORGANISM: Homo sapiens

<400> SEQUENCE: 1

Met Glu Arg Ala Gly Pro Ser Phe Gly Gln Gln Arg Gln Gln Gln Gln
1               5                   10                  15

Pro Gln Gln Gln Lys Gln Gln Arg Asp Gln Asp Ser Val Glu Ala
            20                  25                  30

Trp Leu Asp Asp His Trp Asp Phe Thr Phe Ser Tyr Phe Val Arg Lys
        35                  40                  45

Ala Thr Arg Glu Met Val Asn Ala Trp Phe Ala Glu Arg Val His Thr
    50                  55                  60

Ile Pro Val Cys Lys Glu Gly Ile Arg Gly His Thr Glu Ser Cys Ser
65                  70                  75                  80
```

-continued

```
Cys Pro Leu Gln Gln Ser Pro Arg Ala Asp Asn Ser Ala Pro Gly Thr
                 85                  90                  95

Pro Thr Arg Lys Ile Ser Ala Ser Glu Phe Asp Arg Pro Leu Arg Pro
            100                 105                 110

Ile Val Val Lys Asp Ser Glu Gly Thr Val Ser Phe Leu Ser Asp Ser
            115                 120                 125

Glu Lys Lys Glu Gln Met Pro Leu Thr Pro Pro Arg Phe Asp His Asp
            130                 135                 140

Glu Gly Asp Gln Cys Ser Arg Leu Leu Glu Leu Val Lys Asp Ile Ser
145                 150                 155                 160

Ser His Leu Asp Val Thr Ala Leu Cys His Lys Ile Phe Leu His Ile
                165                 170                 175

His Gly Leu Ile Ser Ala Asp Arg Tyr Ser Leu Phe Leu Val Cys Glu
                180                 185                 190

Asp Ser Ser Asn Asp Lys Phe Leu Ile Ser Arg Leu Phe Asp Val Ala
            195                 200                 205

Glu Gly Ser Thr Leu Glu Glu Val Ser Asn Asn Cys Ile Arg Leu Glu
            210                 215                 220

Trp Asn Lys Gly Ile Val Gly His Val Ala Ala Leu Gly Glu Pro Leu
225                 230                 235                 240

Asn Ile Lys Asp Ala Tyr Glu Asp Pro Arg Phe Asn Ala Glu Val Asp
                245                 250                 255

Gln Ile Thr Gly Tyr Lys Thr Gln Ser Ile Leu Cys Met Pro Ile Lys
                260                 265                 270

Asn His Arg Glu Glu Val Val Gly Val Ala Gln Ala Ile Asn Lys Lys
            275                 280                 285

Ser Gly Asn Gly Gly Thr Phe Thr Glu Lys Asp Glu Lys Asp Phe Ala
            290                 295                 300

Ala Tyr Leu Ala Phe Cys Gly Ile Val Leu His Asn Ala Gln Leu Tyr
305                 310                 315                 320

Glu Thr Ser Leu Leu Glu Asn Lys Arg Asn Gln Val Leu Leu Asp Leu
                325                 330                 335

Ala Ser Leu Ile Phe Glu Glu Gln Gln Ser Leu Glu Val Ile Leu Lys
            340                 345                 350

Lys Ile Ala Ala Thr Ile Ile Ser Phe Met Gln Val Gln Lys Cys Thr
            355                 360                 365

Ile Phe Ile Val Asp Glu Asp Cys Ser Asp Ser Phe Ser Ser Val Phe
            370                 375                 380

His Met Glu Cys Glu Glu Leu Glu Lys Ser Ser Asp Thr Leu Thr Arg
385                 390                 395                 400

Glu His Asp Ala Asn Lys Ile Asn Tyr Met Tyr Ala Gln Tyr Val Lys
                405                 410                 415

Asn Thr Met Glu Pro Leu Asn Ile Pro Asp Val Ser Lys Asp Lys Arg
            420                 425                 430

Phe Pro Trp Thr Thr Glu Asn Thr Gly Asn Val Asn Gln Gln Cys Ile
            435                 440                 445

Arg Ser Leu Leu Cys Thr Pro Ile Lys Asn Gly Lys Lys Asn Lys Val
            450                 455                 460

Ile Gly Val Cys Gln Leu Val Asn Lys Met Glu Glu Asn Thr Gly Lys
465                 470                 475                 480

Val Lys Pro Phe Asn Arg Asn Asp Glu Gln Phe Leu Glu Ala Phe Val
                485                 490                 495

Ile Phe Cys Gly Leu Gly Ile Gln Asn Thr Gln Met Tyr Glu Ala Val
```

```
            500                 505                 510
Glu Arg Ala Met Ala Lys Gln Met Val Thr Leu Glu Val Leu Ser Tyr
        515                 520                 525
His Ala Ser Ala Ala Glu Glu Thr Arg Glu Leu Gln Ser Leu Ala
    530                 535                 540
Ala Ala Val Val Pro Ser Ala Gln Thr Leu Lys Ile Thr Asp Phe Ser
545                 550                 555                 560
Phe Ser Asp Phe Glu Leu Ser Asp Leu Glu Thr Ala Leu Cys Thr Ile
                565                 570                 575
Arg Met Phe Thr Asp Leu Asn Leu Val Gln Asn Phe Gln Met Lys His
            580                 585                 590
Glu Val Leu Cys Arg Trp Ile Leu Ser Val Lys Lys Asn Tyr Arg Lys
        595                 600                 605
Asn Val Ala Tyr His Asn Trp Arg His Ala Phe Asn Thr Ala Gln Cys
    610                 615                 620
Met Phe Ala Ala Leu Lys Ala Gly Lys Ile Gln Asn Lys Leu Thr Asp
625                 630                 635                 640
Leu Glu Ile Leu Ala Leu Leu Ile Ala Ala Leu Ser His Asp Leu Asp
                645                 650                 655
His Arg Gly Val Asn Asn Ser Tyr Ile Gln Arg Ser Glu His Pro Leu
            660                 665                 670
Ala Gln Leu Tyr Cys His Ser Ile Met Glu His His His Phe Asp Gln
        675                 680                 685
Cys Leu Met Ile Leu Asn Ser Pro Gly Asn Gln Ile Leu Ser Gly Leu
    690                 695                 700
Ser Ile Glu Glu Tyr Lys Thr Thr Leu Lys Ile Ile Lys Gln Ala Ile
705                 710                 715                 720
Leu Ala Thr Asp Leu Ala Leu Tyr Ile Lys Arg Arg Gly Glu Phe Phe
                725                 730                 735
Glu Leu Ile Arg Lys Asn Gln Phe Asn Leu Glu Asp Pro His Gln Lys
            740                 745                 750
Glu Leu Phe Leu Ala Met Leu Met Thr Ala Cys Asp Leu Ser Ala Ile
        755                 760                 765
Thr Lys Pro Trp Pro Ile Gln Gln Arg Ile Ala Glu Leu Val Ala Thr
    770                 775                 780
Glu Phe Phe Asp Gln Gly Asp Arg Glu Arg Lys Glu Leu Asn Ile Glu
785                 790                 795                 800
Pro Thr Asp Leu Met Asn Arg Glu Lys Lys Asn Lys Ile Pro Ser Met
                805                 810                 815
Gln Val Gly Phe Ile Asp Ala Ile Cys Leu Gln Leu Tyr Glu Ala Leu
            820                 825                 830
Thr His Val Ser Glu Asp Cys Phe Pro Leu Leu Asp Gly Cys Arg Lys
        835                 840                 845
Asn Arg Gln Lys Trp Gln Ala Leu Ala Glu Gln Gln Glu Lys Met Leu
    850                 855                 860
Ile Asn Gly Glu Ser Gly Gln Ala Lys Arg Asn
865                 870                 875

<210> SEQ ID NO 2
<211> LENGTH: 2628
<212> TYPE: DNA
<213> ORGANISM: Homo sapiens

<400> SEQUENCE: 2
```

-continued

| | | | | | |
|---|---|---|---|---|---|
| atggagcggg | ccggccccag | cttcgggcag | cagcgacagc | agcagcagcc | ccagcagcag | 60 |
| aagcagcagc | agagggatca | ggactcggtc | gaagcatggc | tggacgatca | ctgggacttt | 120 |
| accttctcat | actttgttag | aaaagccacc | agagaaatgg | tcaatgcatg | gtttgctgag | 180 |
| agagttcaca | ccatccctgt | gtgcaaggaa | ggtatcagag | ccacaccga | atcttgctct | 240 |
| tgtcccttgc | agcagagtcc | tcgtgcagat | aacagtgccc | ctggaacacc | aaccaggaaa | 300 |
| atctctgcct | ctgaatttga | ccggcctctt | agacccattg | ttgtcaagga | ttctgaggga | 360 |
| actgtgagct | tcctctctga | ctcagaaaag | aaggaacaga | tgcctctaac | ccctccaagg | 420 |
| tttgatcatg | atgaagggga | ccagtgctca | agactcttgg | aattagtgaa | ggatatttct | 480 |
| agtcatttgg | atgtcacagc | cttatgtcac | aaaattttct | tgcatatcca | tggactgata | 540 |
| tctgctgacc | gctattccct | gttccttgtc | tgtgaagaca | gctccaatga | caagtttctt | 600 |
| atcagccgcc | tctttgatgt | tgctgaaggt | tcaacactgg | aagaagtttc | aaataactgt | 660 |
| atccgcttag | aatggaacaa | aggcattgtg | ggacatgtgg | cagcgcttgg | tgagcccttg | 720 |
| aacatcaaag | atgcatatga | ggatcctcgg | ttcaatgcag | aagttgacca | aattacaggc | 780 |
| tacaagacac | aaagcattct | ttgtatgcca | attaagaatc | atagggaaga | ggttgttggt | 840 |
| gtagcccagg | ccatcaacaa | gaaatcagga | aacggtggga | catttactga | aaaagatgaa | 900 |
| aaggactttg | ctgcttattt | ggcattttgt | ggtattgttc | ttcataatgc | tcagctctat | 960 |
| gagacttcac | tgctggagaa | caagagaaat | caggtgctgc | ttgaccttgc | tagtttaatt | 1020 |
| tttgaagaac | aacaatcatt | agaagtaatt | ttgaagaaaa | tagctgccac | tattatctct | 1080 |
| ttcatgcaag | tgcagaaatg | caccattttc | atagtggatg | aagattgctc | cgattctttt | 1140 |
| tctagtgtgt | ttcacatgga | gtgtgaggaa | ttagaaaaat | catctgatac | attaacaagg | 1200 |
| gaacatgatg | caaacaaaat | caattacatg | tatgctcagt | atgtcaaaaa | tactatggaa | 1260 |
| ccacttaata | tcccagatgt | cagtaaggat | aaaagatttc | cctggacaac | tgaaaataca | 1320 |
| ggaaatgtaa | accagcagtg | cattagaagt | ttgctttgta | cacctataaa | aaatggaaag | 1380 |
| aagaataaag | ttataggggt | ttgccaactt | gttaataaga | tggaggagaa | tactggcaag | 1440 |
| gttaagcctt | tcaaccgaaa | tgacgaacag | tttctggaag | cttttgtcat | cttttgtggc | 1500 |
| ttggggatcc | agaacacgca | gatgtatgaa | gcagtggaga | gagccatggc | caagcaaatg | 1560 |
| gtcacattgg | aggttctgtc | gtatcatgct | tcagcagcag | aggaagaaac | aagagagcta | 1620 |
| cagtcgttag | cggctgctgt | ggtgccatct | gcccagaccc | ttaaaattac | tgactttagc | 1680 |
| ttcagtgact | ttgagctgtc | tgatctggaa | acagcactgt | gtacaattcg | gatgtttact | 1740 |
| gacctcaacc | ttgtgcagaa | cttccagatg | aaacatgagg | ttctttgcag | atggatttta | 1800 |
| agtgttaaga | agaattatcg | gaagaatgtt | gcctatcata | attggagaca | tgcctttaat | 1860 |
| acagctcagt | gcatgtttgc | tgctctaaaa | gcaggcaaaa | ttcagaacaa | gctgactgac | 1920 |
| ctggagatac | ttgcattgct | gattgctgca | ctaagccacg | atttggatca | ccgtggtgtg | 1980 |
| aataactctt | acatacagcg | aagtgaacat | ccacttgccc | agctttactg | ccattcaatc | 2040 |
| atggaacacc | atcattttga | ccagtgcctg | atgattctta | atagtccagg | caatcagatt | 2100 |
| ctcagtggcc | tctccattga | agaatataag | accacgttga | aaataatcaa | gcaagctatt | 2160 |
| ttagctacag | acctagcact | gtacattaag | aggcgaggag | aatttttga | acttataaga | 2220 |
| aaaaatcaat | tcaatttgga | agatcctcat | caaaaggagt | tgttttttggc | aatgctgatg | 2280 |
| acagcttgtg | atctttctgc | aattacaaaa | ccctggcctta | ttcaacaacg | gatagcagaa | 2340 |
| cttgtagcaa | ctgaattttt | tgatcaagga | gacagagaga | gaaaagaact | caacatagaa | 2400 |

```
cccactgatc taatgaacag ggagaagaaa aacaaaatcc caagtatgca agttgggttc    2460
atagatgcca tctgcttgca actgtatgag gccctgaccc acgtgtcaga ggactgtttc    2520
cctttgctag atggctgcag aaagaacagg cagaaatggc aggcccttgc agaacagcag    2580
gagaagatgc tgattaatgg ggaaagcggc caggccaagc ggaactga               2628

<210> SEQ ID NO 3
<211> LENGTH: 833
<212> TYPE: PRT
<213> ORGANISM: Homo sapiens

<400> SEQUENCE: 3

Met Leu Pro Phe Gly Asp Lys Thr Arg Glu Met Val Asn Ala Trp Phe
1               5                   10                  15

Ala Glu Arg Val His Thr Ile Pro Val Cys Lys Glu Gly Ile Arg Gly
            20                  25                  30

His Thr Glu Ser Cys Ser Cys Pro Leu Gln Gln Ser Pro Arg Ala Asp
        35                  40                  45

Asn Ser Ala Pro Gly Thr Pro Thr Arg Lys Ile Ser Ala Ser Glu Phe
    50                  55                  60

Asp Arg Pro Leu Arg Pro Ile Val Val Lys Asp Ser Glu Gly Thr Val
65                  70                  75                  80

Ser Phe Leu Ser Asp Ser Glu Lys Lys Glu Gln Met Pro Leu Thr Pro
                85                  90                  95

Pro Arg Phe Asp His Asp Glu Gly Asp Gln Cys Ser Arg Leu Leu Glu
            100                 105                 110

Leu Val Lys Asp Ile Ser Ser His Leu Asp Val Thr Ala Leu Cys His
        115                 120                 125

Lys Ile Phe Leu His Ile His Gly Leu Ile Ser Ala Asp Arg Tyr Ser
    130                 135                 140

Leu Phe Leu Val Cys Glu Asp Ser Ser Asn Asp Lys Phe Leu Ile Ser
145                 150                 155                 160

Arg Leu Phe Asp Val Ala Glu Gly Ser Thr Leu Glu Glu Val Ser Asn
                165                 170                 175

Asn Cys Ile Arg Leu Glu Trp Asn Lys Gly Ile Val Gly His Val Ala
            180                 185                 190

Ala Leu Gly Glu Pro Leu Asn Ile Lys Asp Ala Tyr Glu Asp Pro Arg
        195                 200                 205

Phe Asn Ala Glu Val Asp Gln Ile Thr Gly Tyr Lys Thr Gln Ser Ile
    210                 215                 220

Leu Cys Met Pro Ile Lys Asn His Arg Glu Glu Val Val Gly Val Ala
225                 230                 235                 240

Gln Ala Ile Asn Lys Lys Ser Gly Asn Gly Gly Thr Phe Thr Glu Lys
                245                 250                 255

Asp Glu Lys Asp Phe Ala Ala Tyr Leu Ala Phe Cys Gly Ile Val Leu
            260                 265                 270

His Asn Ala Gln Leu Tyr Glu Thr Ser Leu Leu Glu Asn Lys Arg Asn
        275                 280                 285

Gln Val Leu Leu Asp Leu Ala Ser Leu Ile Phe Glu Glu Gln Gln Ser
    290                 295                 300

Leu Glu Val Ile Leu Lys Lys Ile Ala Ala Thr Ile Ile Ser Phe Met
305                 310                 315                 320

Gln Val Gln Lys Cys Thr Ile Phe Ile Val Asp Glu Asp Cys Ser Asp
                325                 330                 335
```

```
Ser Phe Ser Ser Val Phe His Met Glu Cys Glu Leu Glu Lys Ser
            340                 345                 350

Ser Asp Thr Leu Thr Arg Glu His Asp Ala Asn Lys Ile Asn Tyr Met
            355                 360                 365

Tyr Ala Gln Tyr Val Lys Asn Thr Met Glu Pro Leu Asn Ile Pro Asp
        370                 375                 380

Val Ser Lys Asp Lys Arg Phe Pro Trp Thr Thr Glu Asn Thr Gly Asn
385                 390                 395                 400

Val Asn Gln Gln Cys Ile Arg Ser Leu Leu Cys Thr Pro Ile Lys Asn
                405                 410                 415

Gly Lys Lys Asn Lys Val Ile Gly Val Cys Gln Leu Val Asn Lys Met
                420                 425                 430

Glu Glu Asn Thr Gly Lys Val Lys Pro Phe Asn Arg Asn Asp Glu Gln
            435                 440                 445

Phe Leu Glu Ala Phe Val Ile Phe Cys Gly Leu Gly Ile Gln Asn Thr
    450                 455                 460

Gln Met Tyr Glu Ala Val Glu Arg Ala Met Ala Lys Gln Met Val Thr
465                 470                 475                 480

Leu Glu Val Leu Ser Tyr His Ala Ser Ala Glu Glu Thr Arg
                485                 490                 495

Glu Leu Gln Ser Leu Ala Ala Ala Val Val Pro Ser Ala Gln Thr Leu
            500                 505                 510

Lys Ile Thr Asp Phe Ser Phe Ser Asp Phe Glu Leu Ser Asp Leu Glu
                515                 520                 525

Thr Ala Leu Cys Thr Ile Arg Met Phe Thr Asp Leu Asn Leu Val Gln
    530                 535                 540

Asn Phe Gln Met Lys His Glu Val Leu Cys Arg Trp Ile Leu Ser Val
545                 550                 555                 560

Lys Lys Asn Tyr Arg Lys Asn Val Ala Tyr His Asn Trp Arg His Ala
                565                 570                 575

Phe Asn Thr Ala Gln Cys Met Phe Ala Ala Leu Lys Ala Gly Lys Ile
            580                 585                 590

Gln Asn Lys Leu Thr Asp Leu Glu Ile Leu Ala Leu Leu Ile Ala Ala
        595                 600                 605

Leu Ser His Asp Leu Asp His Arg Gly Val Asn Asn Ser Tyr Ile Gln
    610                 615                 620

Arg Ser Glu His Pro Leu Ala Gln Leu Tyr Cys His Ser Ile Met Glu
625                 630                 635                 640

His His His Phe Asp Gln Cys Leu Met Ile Leu Asn Ser Pro Gly Asn
                645                 650                 655

Gln Ile Leu Ser Gly Leu Ser Ile Glu Glu Tyr Lys Thr Thr Leu Lys
        660                 665                 670

Ile Ile Lys Gln Ala Ile Leu Ala Thr Asp Leu Ala Leu Tyr Ile Lys
    675                 680                 685

Arg Arg Gly Glu Phe Phe Glu Leu Ile Arg Lys Asn Gln Phe Asn Leu
        690                 695                 700

Glu Asp Pro His Gln Lys Glu Leu Phe Leu Ala Met Leu Met Thr Ala
705                 710                 715                 720

Cys Asp Leu Ser Ala Ile Thr Lys Pro Trp Pro Ile Gln Gln Arg Ile
                725                 730                 735

Ala Glu Leu Val Ala Thr Glu Phe Phe Asp Gln Gly Asp Arg Glu Arg
            740                 745                 750
```

| | | | | | | | | | | | | |
|---|---|---|---|---|---|---|---|---|---|---|---|---|
|Lys|Glu|Leu|Asn|Ile|Glu|Pro|Thr|Asp|Leu|Met|Asn|Arg|Glu|Lys|Lys|
| | |755| | | |760| | | |765| | | | | |

| | | | | | | | | | | | |
|---|---|---|---|---|---|---|---|---|---|---|---|
|Asn|Lys|Ile|Pro|Ser|Met|Gln|Val|Gly|Phe|Ile|Asp|Ala|Ile|Cys|Leu|
| | |770| | | |775| | | |780| | | | | |

| | | | | | | | | | | | |
|---|---|---|---|---|---|---|---|---|---|---|---|
|Gln|Leu|Tyr|Glu|Ala|Leu|Thr|His|Val|Ser|Glu|Asp|Cys|Phe|Pro|Leu|
|785| | | |790| | | |795| | | |800| | | |

| | | | | | | | | | | | |
|---|---|---|---|---|---|---|---|---|---|---|---|
|Leu|Asp|Gly|Cys|Arg|Lys|Asn|Arg|Gln|Lys|Trp|Gln|Ala|Leu|Ala|Glu|
| | | |805| | | |810| | | |815| | | | |

| | | | | | | | | | | | |
|---|---|---|---|---|---|---|---|---|---|---|---|
|Gln|Gln|Glu|Lys|Met|Leu|Ile|Asn|Gly|Glu|Ser|Gly|Gln|Ala|Lys|Arg|
| | |820| | | |825| | | |830| | | | | |

Asn

<210> SEQ ID NO 4
<211> LENGTH: 6836
<212> TYPE: DNA
<213> ORGANISM: Homo sapiens

<400> SEQUENCE: 4

```
tggttctgag tcgccgacct cacctcacct cacctgcgcg cgttgttgcc cctacggagc      60
ctcctggagt ccaggatcgg cggagttcga aaacgaactt cccacgtttg ctatgttgcc     120
ctttggagac aaaacaagag aaatggtcaa tgcatggttt gctgagagag ttcacaccat     180
ccctgtgtgc aaggaaggta tcagaggcca caccgaatct tgctcttgtc ccttgcagca     240
gagtcctcgt gcagataaca gtgcccctgg aacaccaacc aggaaaatct ctgcctctga     300
atttgaccgg cctcttagac ccattgttgt caaggattct gagggaactg tgagcttcct     360
ctctgactca gaaaagaagg aacagatgcc tctaaccccc tccaaggttt gatcatgatga    420
aggggaccag tgctcaagac tcttggaatt agtgaaggat attctagtc atttggatgt      480
cacagcctta tgtcacaaaa ttttcttgca tatccatgga ctgatatctg ctgaccgcta     540
ttccctgttc cttgtctgtg aagacagctc caatgacaag tttcttatca gccgcctctt     600
tgatgttgct gaaggttcaa cactggaaga agtttcaaat aactgtatcc gcttagaatg     660
gaacaaaggc attgtgggac atgtggcagc gcttggtgag cccttgaaca tcaaagatgc     720
atatgaggat cctcggttca tgcagaagt tgaccaaatt acaggctaca agacacaaag      780
cattctttgt atgccaatta agaatcatag ggaagaggtt gttggtgtag cccaggccat     840
caacaagaaa tcaggaaacg gtgggacatt tactgaaaaa gatgaaaagg actttgctgc     900
ttatttggca ttttgtggta ttgttcttca taatgctcag ctctatgaga cttcactgct     960
ggagaacaag agaaatcagg tgctgcttga ccttgctagt ttaattttg aagaacaaca    1020
atcattagaa gtaattttga agaaaatagc tgccactatt atctctttca tgcaagtgca    1080
gaaatgcacc attttcatag tggatgaaga ttgctccgat tcttttttcta gtgtgtttca   1140
catggagtgt gaggaattag aaaaatcatc tgatacatta acaagggaac atgatgcaaa    1200
caaaatcaat tacatgtatg ctcagtatgt caaaaatact atggaaccac ttaatatccc    1260
agatgtcagt aaggataaaa gatttccctg gacaactgaa atacaggaa atgtaaacca     1320
gcagtgcatt agaagtttgc tttgtacacc tataaaaaat ggaagaagaa ataaagttat    1380
aggggtttgc aacttgtta ataagatgga ggagaatact ggcaaggtta agcctttcaa     1440
ccgaaatgac gaacagtttc tggaagcttt tgtcatcttt tgtggcttgg ggatccagaa    1500
cacgcagatg tatgaagcag tggagagagc catggccaag caaatggtca cattggaggt    1560
tctgtcgtat catgcttcag cagcagagga agaaacaaga gagctacagt cgttagcggc    1620
```

```
tgctgtggtg ccatctgccc agacccttaa aattactgac tttagcttca gtgactttga    1680
gctgtctgat ctggaaacag cactgtgtac aattcggatg tttactgacc tcaaccttgt    1740
gcagaacttc cagatgaaac atgaggttct ttgcagatgg attttaagtg ttaagaagaa    1800
ttatcggaag aatgttgcct atcataattg gagacatgcc tttaatacag ctcagtgcat    1860
gtttgctgct ctaaaagcag gcaaaattca gaacaagctg actgacctgg agatacttgc    1920
attgctgatt gctgcactaa gccacgattt ggatcaccgt ggtgtgaata actcttacat    1980
acagcgaagt gaacatccac ttgcccagct ttactgccat tcaatcatgg aacaccatca    2040
ttttgaccag tgcctgatga ttcttaatag tccaggcaat cagattctca gtggcctctc    2100
cattgaagaa tataagacca cgttgaaaat aatcaagcaa gctattttag ctacagacct    2160
agcactgtac attaagaggc gaggagaatt ttttgaactt ataagaaaaa atcaattcaa    2220
tttggaagat cctcatcaaa aggagttgtt tttggcaatg ctgatgacag cttgtgatct    2280
ttctgcaatt acaaaaccct ggcctattca acaacggata gcagaacttg tagcaactga    2340
atttttgat caaggagaca gagagagaaa agaactcaac atagaaccca ctgatctaat     2400
gaacagggag aagaaaaaca aaatcccaag tatgcaagtt gggttcatag atgccatctg    2460
cttgcaactg tatgaggccc tgacccacgt gtcagaggac tgtttccctt tgctagatgg    2520
ctgcagaaag aacaggcaga aatggcaggc ccttgcagaa cagcaggaga agatgctgat    2580
taatggggaa agcggccagg ccaagcggaa ctgagtggcc tatttcatgc agagttgaag    2640
tttacagaga tggtgtgttc tgcaatatgc ctagtttctt acacactgtc tgtatagtgt    2700
ctgtatttgg tatatacttt gccactgctg tattttatt tttgcacaac ttttgagagt     2760
atagcatgaa tgttttaga ggactattac atatttttg tatatttgtt ttatgctact      2820
gaactgaaag gatcaacaac atccactgtt agcacattga taaagcatt gtttgtgata     2880
tttcgtgtac tgcaaagtgt atgcagtatt cttgcactga ggttttttg cttggggatt     2940
attttaaata attggttttt gtgttttctg aattaccatt ttttcaagaa tgtttggaat    3000
ctttcctttt tcaaaagtag gttaggagca aattatcata cattctgtga catttaaagc    3060
ctttatagga tagtgaaaaa tgctggctga gtggatttta agagaaataa ttgtatttgt    3120
taacagtgtc tttttttaaa aagttaaggc actctgaaac aaatggaaag tcctatgaaa    3180
ctgtattgta aagaaaacat tatttaattg atatgctgtt ttgtgagaga acaggcaaga    3240
cagaactttg tcacttcagt gcagtacatt tttctgaaag ctacccataa aatcactttc    3300
atctcaccta cctgatgcaa agcaggtgaa accttaggag atgatccagt cactgacttg    3360
attgagggat aagtgtgatt tagaaatgga atggccttgg atgtctatca gtgaagaaaa    3420
atgttctgtt agaagatctc tctaagagtt ttttccttc tgagcttcct tttcaaaata     3480
aaagtgacaa ttgtagcatt gacttgaagt gagacatggt tatagataag agagtacaaa    3540
atgactcttt ttcctgtcaa ttgaaattta agaaaagtt ttaattatat aaatagcaaa     3600
gggctattgc caatactagg gtcaaaaatg aatttgaggg aacagtgggt aagaaacttt    3660
atgcctgaat aacatttagc agtattgtga ttgaaaaatt gccatatttt gatgtatagg    3720
acaagtcaac tgagatccag agaatcctgg atgtgaatgc taaacactgg cccttaactc    3780
acattcaatg tattttcttc ccataacatt tagtatagtt aatatttct tagaatttga     3840
gcccatttaa gtggattaat attctacatg tgtgccccta agacacatt tactcaatat     3900
tggagaagta gataatgaat taagcaactg gtctaggaaa ggaaaatttg tttcaaatat    3960
gcaggaatgt ttggatttgg ggagagtaga aggagagatt tgcttgattt gttaacttct    4020
```

```
acctccaacc cacaaaaaag atatttgatc tgagtttcta tcactaattt ggatagaaaa    4080
tttctaaggg acatggtaat ccagcattct caaggacctt tcgccaaaat gtgttttcca    4140
tctatgtccc gattcccta  aattttgcct aaaattcagt atgttcctta agttttttaaa  4200 attctgagtg tgtacaaata tcttgacata atgcagtttt attttatca ttctggtaaa    4260 aaaacaaaaa atagaagcaa aacacattgt attgccatta ttttgtattt ggtaaaggtt   4320
aatctaggaa gttaccaact gtttaatgct atatgtattg tatacttgta ttttcaggat   4380 atttttatttt ttttgccata cagataaaat ttgtaaggtt gccctttgt ggcactggtg   4440 tgtaaaatac acagactatc actaaaataa tagttatata tacatacagg tgtatactta   4500
tgcatgcata cataaatcct tagtatagaa aaattgcata agaatagca atctttaata    4560 aacctttta ttacattgtg atttagcagt tatgctaaaa tatgtactta tgctttagta    4620
gtttgtttgg tccctctag tatgtgtcac tgagaaattt tttaaagaca tggtagatcg    4680
tgtttagagg ctttgtatgt gtgtcatttt aataagcaag aagatatatt tagattagaa   4740
atggtttggt ctgcctttga atattgttta ttttacttta ctagttgaga cattaaagga   4800
agctgggcaa tgcctatttt atttctttgt tggatatttt agttcataca aagcagagta   4860
cttctttagg gctggttaat tggttcaaat aatttttaat ttccttcta gtatcttctc    4920 aagttggaaa atatacata cagtcctcct tcaccttact ctgtatttat attacccata    4980
actagcaaga agttcttgtt ctagattttt tgtttgttta gttataacag agtaacatac   5040
catttaatta caattttag ccagaaaagt ccccactatt ttactaactt gttaaaagat    5100
atctatataa ttgcctggcc ttatattttt cagtagatta gaccgtgcca atcacaatcc   5160
tgggtggatt tgtgtaagtc acttaacctc tgtgtgccta aacaagttgt gcttttttaa   5220
aaggagttat gtttgggcaa agcctttgtc ttcaagcaga atgtcacaga aggcagctac   5280
tttataagcc ccaatgggcc atggagacca ctgtcagaaa tgggatatta gtctagagag   5340
aaggtgatct attcccacat gtcatttcta atgttgagtt tccatgactg aacaaagaga   5400
atatatttat tcagcttcac ttgcagatca ctagtgaatg tgagatttag agctcattga   5460
gtatattgct tcaaggtaca aacccaggat gatgatgttg tcaccactgt ctcttaattt   5520
tgaataatag tttccttaa taggagtatt agagataaga aagtatatga aaatatactg    5580
gaaatattgg attcttggag aaaactgttc agtcacagat atattcttgc ctagcagtga   5640
agtgccttta ttttcagcat agcaaataaa tattagacct gttccaattt gatctacaat   5700
ttttttctgt gttttcacc agattgtact cctaaaactt aacaggccat cacaagcaat    5760
tgtcttttgt ttacaagatt gatttaatat gagaggatac aaaatgtcat cgttatcctc   5820
tcttatgaac aactgtagtc aaaataaggt ggcacaattt aattgttttg tatcagaaat   5880
acactgaccc accttttatt gagtcctgcc acatgttagg taccgtgctc tgctgtggag   5940
acagagcagt gaccccaagg agctcacggt ccctgaagga ggtgctagag aagagactta   6000
gcttctgata ctgccaattt aatgtgagaa catggggtat actgcatcat ttccattttc   6060
atcaataaca tatgttttat gcaccttctt tacctgaaac ttactaagaa tctaccagta   6120
aacaaacatc ctgtctttt gcaagtatga atcacttaac ctgctgatag ttgaagaaca   6180
ctttaggagt tttgtattct tgtatatagt ttatttttc catgtgctag ccaggtaaag    6240
attacacagt tcttctggac tgttaaattg tgcatggttt tggacccctt ctgctctact   6300
acagagagtg aagaagaaag tattaaagct cactttacca ttccatatac ttactaaaag   6360
```

```
cctgtgtaaa catgtcttaa tgaatgttgt tgaaagcaat gtaaatagtt gaaaatataa    6420
atttatatta cagtttaaga aaaccttatg aggcatcact agccactgtt aatatctatt    6480
tgtattctta taccttttca atatatttga acaaatatag tttctggcac tattttata     6540 ctaggaaaag gagttactat gtatattatg cttagctttt aaggcatttt aaataaccat    6600
gaatgttgat ttcattactt tcctttcctc catcacgaga gtcatttcag atgactcttt    6660
catgacaaaa tcactttaaa ggaacactta cctccgattc ctgtataaag tcatgagatg    6720
gtcaaggtgg ttttccattg tgcaaattct tcacctgtca gtggtttcct cattttgcca    6780
tgctttgtaa aaataaaaag aatgatcaag taggtatgaa aaaaaaaaaa aaaaaa        6836

<210> SEQ ID NO 5
<211> LENGTH: 823
<212> TYPE: PRT
<213> ORGANISM: Homo sapiens

<400> SEQUENCE: 5

Met Val Asn Ala Trp Phe Ala Glu Arg Val His Thr Ile Pro Val Cys
1               5                   10                  15

Lys Glu Gly Ile Arg Gly His Thr Glu Ser Cys Ser Cys Pro Leu Gln
            20                  25                  30

Gln Ser Pro Arg Ala Asp Asn Ser Ala Pro Gly Thr Pro Thr Arg Lys
        35                  40                  45

Ile Ser Ala Ser Glu Phe Asp Arg Pro Leu Arg Pro Ile Val Val Lys
    50                  55                  60

Asp Ser Glu Gly Thr Val Ser Phe Leu Ser Asp Ser Glu Lys Lys Glu
65                  70                  75                  80

Gln Met Pro Leu Thr Pro Pro Arg Phe Asp His Asp Glu Gly Asp Gln
                85                  90                  95

Cys Ser Arg Leu Leu Glu Leu Val Lys Asp Ile Ser Ser His Leu Asp
            100                 105                 110

Val Thr Ala Leu Cys His Lys Ile Phe Leu His Ile His Gly Leu Ile
        115                 120                 125

Ser Ala Asp Arg Tyr Ser Leu Phe Leu Val Cys Glu Asp Ser Ser Asn
    130                 135                 140

Asp Lys Phe Leu Ile Ser Arg Leu Phe Asp Val Ala Glu Gly Ser Thr
145                 150                 155                 160

Leu Glu Glu Val Ser Asn Asn Cys Ile Arg Leu Glu Trp Asn Lys Gly
                165                 170                 175

Ile Val Gly His Val Ala Ala Leu Gly Glu Pro Leu Asn Ile Lys Asp
            180                 185                 190

Ala Tyr Glu Asp Pro Arg Phe Asn Ala Glu Val Asp Gln Ile Thr Gly
        195                 200                 205

Tyr Lys Thr Gln Ser Ile Leu Cys Met Pro Ile Lys Asn His Arg Glu
    210                 215                 220

Glu Val Val Gly Val Ala Gln Ala Ile Asn Lys Lys Ser Gly Asn Gly
225                 230                 235                 240

Gly Thr Phe Thr Glu Lys Asp Glu Lys Asp Phe Ala Ala Tyr Leu Ala
                245                 250                 255

Phe Cys Gly Ile Val Leu His Asn Ala Gln Leu Tyr Glu Thr Ser Leu
            260                 265                 270

Leu Glu Asn Lys Arg Asn Gln Val Leu Leu Asp Leu Ala Ser Leu Ile
        275                 280                 285

Phe Glu Glu Gln Gln Ser Leu Glu Val Ile Leu Lys Lys Ile Ala Ala
```

```
            290                 295                 300
Thr Ile Ile Ser Phe Met Gln Val Gln Lys Cys Thr Ile Phe Ile Val
305                 310                 315                 320

Asp Glu Asp Cys Ser Asp Ser Phe Ser Ser Val Phe His Met Glu Cys
                    325                 330                 335

Glu Glu Leu Glu Lys Ser Ser Asp Thr Leu Thr Arg Glu His Asp Ala
                340                 345                 350

Asn Lys Ile Asn Tyr Met Tyr Ala Gln Tyr Val Lys Asn Thr Met Glu
            355                 360                 365

Pro Leu Asn Ile Pro Asp Val Ser Lys Asp Lys Arg Phe Pro Trp Thr
370                 375                 380

Thr Glu Asn Thr Gly Asn Val Asn Gln Gln Cys Ile Arg Ser Leu Leu
385                 390                 395                 400

Cys Thr Pro Ile Lys Asn Gly Lys Lys Asn Lys Val Ile Gly Val Cys
                405                 410                 415

Gln Leu Val Asn Lys Met Glu Glu Asn Thr Gly Lys Val Lys Pro Phe
                420                 425                 430

Asn Arg Asn Asp Glu Gln Phe Leu Glu Ala Phe Val Ile Phe Cys Gly
            435                 440                 445

Leu Gly Ile Gln Asn Thr Gln Met Tyr Glu Ala Val Glu Arg Ala Met
        450                 455                 460

Ala Lys Gln Met Val Thr Leu Glu Val Leu Ser Tyr His Ala Ser Ala
465                 470                 475                 480

Ala Glu Glu Glu Thr Arg Glu Leu Gln Ser Leu Ala Ala Ala Val Val
                485                 490                 495

Pro Ser Ala Gln Thr Leu Lys Ile Thr Asp Phe Ser Phe Ser Asp Phe
                500                 505                 510

Glu Leu Ser Asp Leu Glu Thr Ala Leu Cys Thr Ile Arg Met Phe Thr
            515                 520                 525

Asp Leu Asn Leu Val Gln Asn Phe Gln Met Lys His Glu Val Leu Cys
530                 535                 540

Arg Trp Ile Leu Ser Val Lys Lys Asn Tyr Arg Lys Asn Val Ala Tyr
545                 550                 555                 560

His Asn Trp Arg His Ala Phe Asn Thr Ala Gln Cys Met Phe Ala Ala
                565                 570                 575

Leu Lys Ala Gly Lys Ile Gln Asn Lys Leu Thr Asp Leu Glu Ile Leu
                580                 585                 590

Ala Leu Leu Ile Ala Ala Leu Ser His Asp Leu Asp His Arg Gly Val
            595                 600                 605

Asn Asn Ser Tyr Ile Gln Arg Ser Glu His Pro Leu Ala Gln Leu Tyr
        610                 615                 620

Cys His Ser Ile Met Glu His His His Phe Asp Gln Cys Leu Met Ile
625                 630                 635                 640

Leu Asn Ser Pro Gly Asn Gln Ile Leu Ser Gly Leu Ser Ile Glu Glu
                645                 650                 655

Tyr Lys Thr Thr Leu Lys Ile Ile Lys Gln Ala Ile Leu Ala Thr Asp
                660                 665                 670

Leu Ala Leu Tyr Ile Lys Arg Arg Gly Glu Phe Phe Glu Leu Ile Arg
            675                 680                 685

Lys Asn Gln Phe Asn Leu Glu Asp Pro His Gln Lys Glu Leu Phe Leu
        690                 695                 700

Ala Met Leu Met Thr Ala Cys Asp Leu Ser Ala Ile Thr Lys Pro Trp
705                 710                 715                 720
```

```
Pro Ile Gln Gln Arg Ile Ala Glu Leu Val Ala Thr Glu Phe Phe Asp
            725                 730                 735

Gln Gly Asp Arg Glu Arg Lys Glu Leu Asn Ile Glu Pro Thr Asp Leu
        740                 745                 750

Met Asn Arg Glu Lys Lys Asn Lys Ile Pro Ser Met Gln Val Gly Phe
            755                 760                 765

Ile Asp Ala Ile Cys Leu Gln Leu Tyr Glu Ala Leu Thr His Val Ser
        770                 775                 780

Glu Asp Cys Phe Pro Leu Leu Asp Gly Cys Arg Lys Asn Arg Gln Lys
785                 790                 795                 800

Trp Gln Ala Leu Ala Glu Gln Gln Glu Lys Met Leu Ile Asn Gly Glu
            805                 810                 815

Ser Gly Gln Ala Lys Arg Asn
            820

<210> SEQ ID NO 6
<211> LENGTH: 6788
<212> TYPE: DNA
<213> ORGANISM: Homo sapiens

<400> SEQUENCE: 6
```

| | |
|---|---:|
| cctcgccctg gccctggctg ggcggggaag ctggggtgag ggacgagtcc acgggacagc | 60 |
| ccaaaggcaa catgacggaa ccttgccaaa agaaatggtc aatgcatggt ttgctgagag | 120 |
| agttcacacc atccctgtgt gcaaggaagg tatcagaggc cacaccgaat cttgctcttg | 180 |
| tcccttgcag cagagtcctc gtgcagataa cagtgcccct ggaacaccaa ccaggaaaat | 240 |
| ctctgcctct gaatttgacc ggcctcttag acccattgtt gtcaaggatt ctgagggaac | 300 |
| tgtgagcttc ctctctgact cagaaaagaa ggaacagatg cctctaaccc ctccaaggtt | 360 |
| tgatcatgat gaaggggacc agtgctcaag actcttggaa ttagtgaagg atatttctag | 420 |
| tcatttggat gtcacagcct tatgtcacaa aattttcttg catatccatg gactgatatc | 480 |
| tgctgaccgc tattccctgt tccttgtctg tgaagacagc tccaatgaca agtttcttat | 540 |
| cagccgcctc tttgatgttg ctgaaggttc aacactggaa gaagtttcaa ataactgtat | 600 |
| ccgcttagaa tggaacaaag gcattgtggg acatgtggca gcgcttggtg agcccttgaa | 660 |
| catcaaagat gcatatgagg atcctcggtt caatgcagaa gttgaccaaa ttacaggcta | 720 |
| caagacacaa agcattcttt gtatgccaat taagaatcat agggaagagg ttgttggtgt | 780 |
| agcccaggcc atcaacaaga atcaggaaac ggtgggaca tttactgaaa aagatgaaaa | 840 |
| ggactttgct gcttatttgg catttttgtgg tattgttctt cataatgctc agctctatga | 900 |
| gacttcactg ctggagaaca agagaaatca ggtgctgctt gaccttgcta gtttaattttt | 960 |
| tgaagaacaa caatcattag aagtaatttt gaagaaaata gctgccacta ttatctcttt | 1020 |
| catgcaagtg cagaaatgca ccattttcat agtggatgaa gattgctccg attcttttc | 1080 |
| tagtgtgttt cacatggagt gtgaggaatt agaaaaatca tctgatacat taacaaggga | 1140 |
| acatgatgca aacaaaatca attacatgta tgctcagtat gtcaaaaata ctatggaacc | 1200 |
| acttaatatc ccagatgtca gtaaggataa aagatttccc tggacaactg aaaatacagg | 1260 |
| aaatgtaaac cagcagtgca ttagaagttt gcttttgtaca cctataaaaa atggaaagaa | 1320 |
| gaataaagtt atagggggttt gccaacttgt taataagatg gaggagaata ctggcaaggt | 1380 |
| taagcctttc aaccgaaatg acgaacagtt tctggaagct tttgtcatct tttgtggctt | 1440 |
| ggggatccag aacacgcaga tgtatgaagc agtggagaga gccatggcca agcaaatggt | 1500 |

```
cacattggag gttctgtcgt atcatgcttc agcagcagag gaagaaacaa gagagctaca    1560
gtcgttagcg gctgctgtgg tgccatctgc ccagacccct aaaattactg actttagctt    1620
cagtgacttt gagctgtctg atctggaaac agcactgtgt acaattcgga tgtttactga    1680
cctcaacctt gtgcagaact tccagatgaa acatgaggtt cttgcagat ggattttaag     1740 tgttaagaag aattatcgga agaatgttgc ctatcataat tggagacatg cctttaatac    1800
agctcagtgc atgtttgctg ctctaaaagc aggcaaaatt cagaacaagc tgactgacct    1860
ggagatactt gcattgctga ttgctgcact aagccacgat ttggatcacc gtggtgtgaa    1920
taactcttac atacagcgaa gtgaacatcc acttgcccag ctttactgcc attcaatcat    1980
ggaacaccat cattttgacc agtgcctgat gattcttaat agtccaggca atcagattct    2040
cagtggcctc tccattgaag aatataagac cacgttgaaa ataatcaagc aagctatttt    2100
agctacagac ctagcactgt acattaagag gcgaggagaa ttttttgaac ttataagaaa    2160
aaatcaattc aatttggaag atcctcatca aaaggagttg ttttggcaa tgctgatgac    2220 agcttgtgat ctttctgcaa ttacaaaacc ctggcctatt caacaacgga tagcagaact    2280
tgtagcaact gaattttttg atcaaggaga cagagagaga aaagaactca acatagaacc    2340
cactgatcta atgaacaggg agaagaaaaa caaaatccca agtatgcaag ttgggttcat    2400
agatgccatc tgcttgcaac tgtatgaggc cctgacccac gtgtcagagg actgtttccc    2460
tttgctagat ggctgcagaa agaacaggca gaaatggcag gcccttgcag aacagcagga    2520
gaagatgctg attaatgggg aaagcggcca ggccaagcgg aactgagtgg cctatttcat    2580
gcagagttga agtttacaga gatggtgtgt tctgcaatat gcctagtttc ttacacactg    2640
tctgtatagt gtctgtattt ggtatatact ttgccactgc tgtattttta ttttgcaca    2700 acttttgaga gtatagcatg aatgttttta gaggactatt acatattttt tgtatatttg    2760
ttttatgcta ctgaactgaa aggatcaaca acatccactg ttagcacatt gataaaagca    2820
ttgtttgtga tatttcgtgt actgcaaagt gtatgcagta ttcttgcact gaggtttttt    2880
tgcttgggga ttattttaaa taattggttt ttgtgttttc tgaattacca ttttttcaag    2940
aatgtttgga atctttcctt tttcaaaagt aggttaggag caaattatca tacattctgt    3000
gacatttaaa gcctttatag gatagtgaaa aatgctggct gagtggattt taagagaaat    3060
aattgtattt gttaacagtg tctttttta aaaagttaag gcactctgaa acaaatggaa     3120
agtcctatga aactgtattg taaagaaaac attatttaat tgatatgctg ttttgtgaga    3180
gaacaggcaa gacagaactt tgtcacttca gtgcagtaca tttttctgaa agctacccat    3240
aaaatcactt tcatctcacc tacctgatgc aaagcaggtg aaaccttagg agatgatcca    3300
gtcactgact tgattgaggg ataagtgtga tttagaaatg gaatggcctt ggatgtctat    3360
cagtgaagaa aaatgttctg ttagaagatc tctctaagag tttttttcct tctgagcttc    3420
cttttcaaaa taaagtgac aattgtagca ttgacttgaa gtgagacatg gttatagata    3480
agagagtaca aaatgactct ttttcctgtc aattgaaatt taagaaaag ttttaattat     3540 ataaatagca aagggctatt gccaatacta gggtcaaaaa tgaatttgag gaacagtgg    3600 gtaagaaact ttatgcctga ataacattta gcagtattgt gattgaaaaa ttgccatatt    3660
ttgatgtata ggacaagtca actgagatcc agagaatcct ggatgtgaat gctaaacact    3720
ggcccttaac tcacattcaa gtatttttct tcccataaca tttagtatag ttaatatttt    3780
cttagaattt gagcccattt aagtggatta atattctaca tgtgtgcccc taaagacaca    3840
```

```
                                       -continued
tttactcaat attggagaag tagataatga attaagcaac tggtctagga aaggaaaatt    3900
tgtttcaaat atgcaggaat gtttggattt ggggagagta gaaggagaga tttgcttgat    3960
ttgttaactt ctacctccaa cccacaaaaa agatatttga tctgagtttc tatcactaat    4020
ttggatagaa aatttctaag ggacatggta atccagcatt ctcaaggacc tttcgccaaa    4080
atgtgttttc catctatgtc ccgattcccc taaattttgc ctaaaattca gtatgttcct    4140
taagttttta aaattctgag tgtgtacaaa tatcttgaca taatgcagtt ttattttat     4200 cattctggta aaaaacaaa aaatagaagc aaaacacatt gtattgccat tatttttgtat    4260 ttggtaaagg ttaatctagg aagttaccaa ctgtttaatg ctatatgtat tgtatacttg    4320
tattttcagg atatttttatt tttttttgcca tacagataaa atttgtaagg ttgccccttt   4380
gtggcactgg tgtgtaaaat acacagacta tcactaaaat aatagttata tatacataca    4440
ggtgtatact tatgcatgca tacataaatc cttagtatag aaaaattgca taaagaatag    4500
caatctttaa taaaccttt tattacattg tgatttagca gttatgctaa aatatgtact     4560
tatgctttag tagtttgttt ggtcccctct agtatgtgtc actgagaaat ttttaaaga     4620 catggtagat cgtgtttaga ggctttgtat gtgtgtcatt ttaataagca agaagatata    4680
tttagattag aaatggtttg gtctgccttt gaatattgtt tattttactt tactagttga    4740
gacattaaag gaagctgggc aatgcctatt ttatttcttt gttggatatt ttagttcata    4800
caaagcagag tacttctta gggctggtta attggttcaa ataattttta atttcctttc    4860
tagtatcttc tcaagttgga aaaatataca tacagtcctc cttcacctta ctctgtattt    4920
atattaccca taactagcaa gaagttcttg ttctagattt tttgtttgtt tagttataac    4980
agagtaacat accatttaat tacaattttt agccagaaaa gtccccacta ttttactaac    5040
ttgttaaaag atatctatat aattgcctgg ccttatattt ttcagtagat tagaccgtgc    5100
caatcacaat cctgggtgga tttgtgtaag tcacttaacc tctgtgtgcc taaacaagtt    5160
gtgctttttt aaaaggagtt atgtttgggc aaagcctttg tcttcaagca gaatgtcaca    5220
gaaggcagct actttataag ccccaatggg ccatggagac cactgtcaga aatgggatat    5280
tagtctagag agaaggtgat ctattcccac atgtcatttc taatgttgag tttccatgac    5340
tgaacaaaga gaatatattt attcagcttc acttgcagat cactagtgaa tgtgagattt    5400
agagctcatt gagtatattg cttcaaggta caaacccagg atgatgatgt tgtcaccact    5460
gtctcttaat tttgaataat agtttccttt aataggagta ttagagataa gaaagtatat    5520
gaaaatatac tggaaatatt ggattcttgg agaaaactgt tcagtcacag atatattctt    5580
gcctagcagt gaagtgcctt tattttcagc atagcaaata aatattagac ctgttccaat    5640
ttgatctaca atttttttct gtgttttca ccagattgta ctcctaaaac ttaacaggcc     5700
atcacaagca attgtcttt gtttacaaga ttgatttaat atgagaggat acaaaatgtc     5760
atcgttatcc tctcttatga acaactgtag tcaaaataag gtggcacaat ttaattgttt    5820
tgtatcagaa atacactgac ccacctttta ttgagtcctg ccacatgtta ggtaccgtgc    5880
tctgctgtgg agacagagca gtgaccccaa ggagctcacg gtccctgaag gaggtgctag    5940
agaagagact tagcttctga tactgccaat ttaatgtgag aacatggggt atactgcatc    6000
atttccattt tcatcaataa catatgtttt atgcaccttc tttacctgaa acttactaag    6060
aatctaccag taaacaaaca tcctgtcttt ttgcaagtat gaatcactta acctgctgat    6120
agttgaagaa cactttagga gttttgtatt cttgtatata gttatttttt tccatgtgct    6180
agccaggtaa agattacaca gttcttctgg actgttaaat tgtgcatggt tttggacccc    6240
```

-continued

```
ttctgctcta ctacagagag tgaagaagaa agtattaaag ctcactttac cattccatat    6300
acttactaaa agcctgtgta acatgtctt aatgaatgtt gttgaaagca atgtaaatag     6360
ttgaaaatat aaatttatat tacagtttaa gaaaaccttga tgaggcatca ctagccactg   6420
ttaatatcta tttgtattct tataccttt caatatattt gaacaaatat agtttctggc     6480
actattttta tactaggaaa aggagttact atgtatatta tgcttagctt ttaaggcatt    6540
ttaaataacc atgaatgttg atttcattac tttccttcc tccatcacga gagtcatttc     6600
agatgactct ttcatgacaa aatcacttta aaggaacact tacctccgat tcctgtataa    6660
agtcatgaga tggtcaaggt ggttttccat tgtgcaaatt cttcacctgt cagtggtttc    6720 ctcatttgc catgctttgt aaaaataaaa agaatgatca agtaggtatg aaaaaaaaaa      6780
aaaaaaaa                                                             6788
```

<210> SEQ ID NO 7
<211> LENGTH: 326
<212> TYPE: PRT
<213> ORGANISM: Homo sapiens

<400> SEQUENCE: 7

```
Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Gln Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270
```

Arg Glu Lys Lys Asn Lys Ile Pro Ser Met Gln Val Gly Phe Ile Asp
            275                 280                 285

Ala Ile Cys Leu Gln Leu Tyr Glu Ala Leu Thr His Val Ser Glu Asp
        290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 8
<211> LENGTH: 978
<212> TYPE: DNA
<213> ORGANISM: Homo sapiens

<400> SEQUENCE: 8

```
gaagaaacaa gagagctaca gtcgttagcg gctgctgtgg tgccatctgc ccagacccttt    60
aaaattactg actttagctt cagtgacttt gagctgtctg atctggaaac agcactgtgt   120
acaattcgga tgtttactga cctcaacctt gtgcagaact tccagatgaa acatgaggtt   180
ctttgcagat ggattttaag tgttaagaag aattatcgga gaatgttgc ctatcataat    240
tggagacatg cctttaatac agctcagtgc atgtttgctg ctctaaaagc aggcaaaatt   300
cagaacaagc tgactgacct ggagatactt gcattgctga ttgctgcact aagccacgat   360
ttggatcacc gtggtgtgaa taactcttac atacagcgaa gtgaacatcc acttgcccag   420
ctttactgcc attcaatcat ggaacaccat cattttgacc agtgcctgat gattcttaat   480
agtccaggca atcagattct cagtggcctc tccattgaag aatataagac cacgttgaaa   540
ataatcaagc aagctatttt agctacagac ctagcactgt acattaagag gcgaggagaa   600
ttttttgaac ttataagaaa aaatcaattc aatttggaag atcctcatca aaaggagttg   660
tttttggcaa tgctgatgac agcttgtgat ctttctgcaa ttacaaaacc ctggcctatt   720
caacaacgga tagcagaact tgtagcaact gaattttttg atcaaggaga cagagagaga   780
aaagaactca acatagaacc cactgatcta atgaacaggg agaagaaaaa caaaatccca   840
agtatgcaag ttgggttcat agatgccatc tgcttgcaac tgtatgaggc cctgacccac   900
gtgtcagagg actgtttccc tttgctagat ggctgcagaa agaacaggca gaaatggcag   960
gcccttgcag aacagcag                                                 978
```

<210> SEQ ID NO 9
<211> LENGTH: 875
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 9

Met Glu Arg Ala Gly Pro Ser Phe Gly Gln Gln Arg Gln Gln Gln Gln
1               5                   10                  15

Pro Gln Gln Gln Lys Gln Gln Gln Arg Asp Gln Asp Ser Val Glu Ala
            20                  25                  30

Trp Leu Asp Gly His Trp Asp Phe Thr Phe Ser Tyr Phe Val Arg Lys
        35                  40                  45

Ala Thr Arg Glu Met Val Asn Ala Trp Phe Ala Glu Arg Val His Thr
    50                  55                  60

```
Ile Pro Val Cys Lys Glu Gly Ile Arg Gly His Thr Glu Ser Cys Ser
 65                  70                  75                  80

Cys Pro Leu Gln Gln Ser Pro Arg Ala Asp Asn Ser Val Pro Gly Thr
             85                  90                  95

Pro Thr Arg Lys Ile Ser Ala Ser Glu Phe Asp Arg Pro Leu Arg Pro
            100                 105                 110

Ile Val Val Lys Asp Ser Glu Gly Thr Val Ser Phe Leu Ser Asp Ser
        115                 120                 125

Glu Lys Lys Glu Gln Met Pro Leu Thr Pro Pro Arg Phe Asp His Asp
130                 135                 140

Glu Gly Asp Gln Cys Ser Arg Leu Leu Glu Leu Val Lys Asp Ile Ser
145                 150                 155                 160

Ser His Leu Asp Val Thr Ala Leu Cys His Lys Ile Phe Leu His Ile
                165                 170                 175

His Gly Leu Ile Ser Ala Asp Arg Tyr Ser Leu Phe Leu Val Cys Glu
            180                 185                 190

Asp Ser Ser Asn Asp Lys Phe Leu Ile Ser Arg Leu Phe Asp Val Ala
        195                 200                 205

Glu Gly Ser Thr Leu Glu Glu Val Ser Asn Asn Cys Ile Arg Leu Glu
210                 215                 220

Trp Asn Lys Gly Ile Val Gly His Val Ala Ala Leu Gly Glu Pro Leu
225                 230                 235                 240

Asn Ile Lys Asp Ala Tyr Glu Asp Pro Arg Phe Asn Ala Glu Val Asp
                245                 250                 255

Gln Ile Thr Gly Tyr Lys Thr Gln Ser Ile Leu Cys Met Pro Ile Lys
            260                 265                 270

Asn His Arg Glu Glu Val Val Gly Val Ala Gln Ala Ile Asn Lys Lys
        275                 280                 285

Ser Gly Asn Gly Gly Thr Phe Thr Glu Lys Asp Glu Lys Asp Phe Ala
290                 295                 300

Ala Tyr Leu Ala Phe Cys Gly Ile Val Leu His Asn Ala Gln Leu Tyr
305                 310                 315                 320

Glu Thr Ser Leu Leu Glu Asn Lys Arg Asn Gln Val Leu Leu Asp Leu
                325                 330                 335

Ala Ser Leu Ile Phe Glu Glu Gln Gln Ser Leu Glu Val Ile Leu Lys
            340                 345                 350

Lys Ile Ala Ala Thr Ile Ile Ser Phe Met Gln Val Gln Lys Cys Thr
        355                 360                 365

Ile Phe Ile Val Asp Glu Asp Cys Ser Asp Ser Phe Ser Ser Val Phe
370                 375                 380

His Met Glu Cys Glu Glu Leu Glu Lys Ser Ser Asp Thr Leu Thr Arg
385                 390                 395                 400

Glu His Asp Ala Asn Lys Ile Asn Tyr Met Tyr Ala Gln Tyr Val Lys
                405                 410                 415

Asn Thr Met Glu Pro Leu Asn Ile Pro Asp Val Ser Lys Asp Lys Arg
            420                 425                 430

Phe Pro Trp Thr Thr Glu Asn Thr Gly Asn Val Asn Gln Gln Cys Ile
        435                 440                 445

Arg Ser Leu Leu Cys Thr Pro Ile Lys Asn Gly Lys Lys Asn Lys Val
450                 455                 460

Ile Gly Val Cys Gln Leu Val Asn Lys Met Glu Glu Asn Thr Gly Lys
465                 470                 475                 480

Val Lys Pro Phe Asn Arg Asn Asp Glu Gln Phe Leu Glu Ala Phe Val
```

```
                    485                 490                 495
Ile Phe Cys Gly Leu Gly Ile Gln Asn Thr Gln Met Tyr Glu Ala Val
                500                 505                 510

Glu Arg Ala Met Ala Lys Gln Met Val Thr Leu Glu Val Leu Ser Tyr
            515                 520                 525

His Ala Ser Ala Ala Glu Glu Thr Arg Glu Leu Gln Ser Leu Ala
        530                 535                 540

Ala Ala Val Val Pro Ser Ala Gln Thr Leu Lys Ile Thr Asp Phe Ser
545                 550                 555                 560

Phe Ser Asp Phe Glu Leu Ser Asp Leu Glu Thr Ala Leu Cys Thr Ile
                565                 570                 575

Arg Met Phe Thr Asp Leu Asn Leu Val Gln Asn Phe Arg Met Lys His
            580                 585                 590

Glu Val Leu Cys Arg Trp Ile Leu Ser Val Lys Lys Asn Tyr Arg Lys
        595                 600                 605

Asn Val Ala Tyr His Asn Trp Arg His Ala Phe Asn Thr Ala Gln Cys
        610                 615                 620

Met Phe Ala Ala Leu Lys Ala Gly Lys Ile Gln Asn Lys Leu Thr Asp
625                 630                 635                 640

Leu Glu Ile Leu Ala Leu Leu Ile Ala Ala Leu Ser His Asp Leu Asp
                645                 650                 655

His Arg Gly Val Asn Asn Ser Tyr Ile Gln Arg Ser Glu His Pro Leu
            660                 665                 670

Ala Gln Leu Tyr Cys His Ser Ile Met Glu His His His Phe Asp Gln
        675                 680                 685

Cys Leu Met Ile Leu Asn Ser Pro Gly Asn Gln Ile Leu Ser Gly Leu
        690                 695                 700

Ser Ile Glu Glu Tyr Lys Thr Thr Leu Lys Ile Ile Lys Gln Ala Ile
705                 710                 715                 720

Leu Ala Thr Asp Leu Ala Leu Tyr Ile Lys Arg Arg Gly Glu Phe Phe
                725                 730                 735

Glu Leu Ile Arg Lys Asn Gln Phe Asn Leu Glu Asp Pro His Gln Lys
            740                 745                 750

Glu Leu Phe Leu Ala Met Leu Met Thr Ala Cys Asp Leu Ser Ala Ile
        755                 760                 765

Thr Lys Pro Trp Pro Ile Gln Gln Arg Ile Ala Glu Leu Val Ala Thr
        770                 775                 780

Glu Phe Phe Asp Gln Gly Asp Arg Glu Arg Lys Glu Leu Asn Ile Glu
785                 790                 795                 800

Pro Thr Asp Leu Met Asn Arg Glu Lys Lys Asn Lys Ile Pro Ser Met
                805                 810                 815

Gln Val Gly Phe Ile Asp Ala Ile Cys Leu Gln Leu Tyr Glu Ala Leu
            820                 825                 830

Thr His Val Ser Glu Asp Cys Phe Pro Leu Leu Asp Gly Cys Arg Lys
        835                 840                 845

Asn Arg Gln Lys Trp Gln Ala Leu Ala Glu Gln Gln Glu Lys Met Leu
        850                 855                 860

Ile Asn Gly Glu Ser Gly Gln Ala Lys Arg Asn
865                 870                 875

<210> SEQ ID NO 10
<211> LENGTH: 2625
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic construct"

<400> SEQUENCE: 10

```
atggagcggg ccggccccag cttcgggcag cagcgacagc agcagcagcc ccagcagcag      60
aagcagcagc agagggatca ggactcggtc gaagcatggc tggacggtca ctgggacttt     120
accttctcat actttgttag aaaagccacc agagaaatgg tcaatgcatg gtttgctgag     180
agagttcaca ccatccctgt gtgcaaggaa ggtatcagag ccacaccga atcttgctct      240
tgtcccttgc agcagagtcc tcgtgcagat aacagtgtcc ctggaacacc aaccaggaaa     300
atctctgcct ctgaatttga ccggcctctt agacccattg ttgtcaagga ttctgaggga     360
actgtgagct cctctctga ctcagaaaag aaggaacaga tgcctctaac ccctccaagg      420
tttgatcatg atgaagggga ccagtgctca agactcttgg aattagtgaa ggatatttct     480
agtcatttgg atgtcacagc cttatgtcac aaaattttct tgcatatcca tggactgata     540
tctgctgacc gctattccct gttccttgtc tgtgaagaca gctccaatga caagtttctt     600
atcagccgcc tctttgatgt tgctgaaggt tcaacactgg aagaagtttc aaataactgt     660
atccgcttag aatggaacaa aggcattgtg ggacatgtgg cagcgcttgg tgagcccttg     720
aacatcaaag atgcatatga ggatcctcgg ttcaatgcag aagttgacca aattacaggc     780
tacaagacac aaagcattct tgtatgcca attaagaatc atagggaaga ggttgttggt     840
gtagcccagg ccatcaacaa gaaatcagga acggtggga catttactga aaaagatgaa     900
aaggactttg ctgcttattt ggcattttgt ggtattgttc ttcataatgc tcagctctat     960
gagacttcac tgctggagaa caagagaaat caggtgctgc tcgaccttgc tagtttaatt    1020
tttgaagaac aacaatcatt agaagtaatt ttgaagaaaa tagctgccac tattatctct    1080
ttcatgcaag tgcagaaatg caccattttc atagtggatg aagattgctc cgattctttt    1140
tctagtgtgt tcacatgga gtgtgaggaa ttagaaaaat catctgatac attaacaagg    1200
gaacatgatg caaacaaaat caattacatg tatgctcagt acgtcaaaaa tactatggaa    1260
ccacttaata tcccagatgt cagtaaggat aaaagatttc cctggacaac tgaaaataca    1320
ggaaatgtaa accagcagtg cattagaagt ttgcttttgta cacctataaa aaatggaaag    1380
aagaataaag ttatagggt ttgccaactt gttaataaga tggaggagaa tactggcaag    1440
gttaaacctt tcaaccgaaa tgacgaacag tttctggaag cttttgtcat ctttttgtggc    1500
ttggggatcc agaacacgca gatgtatgaa gcagtggaga gagccatggc caagcaaatg    1560
gtcacattgg aggttctgtc gtatcatgct tcagcagcag aggaagaaac aagagagcta    1620
cagtcgttag cggctgctgt ggtgccatct gcccagaccc ttaaaattac tgactttagc    1680
ttcagtgact ttgagctgtc tgatctggaa acagcactgt gtacaattcg gatgtttact    1740
gacctcaacc ttgtgcagaa cttccggatg aaacatgagg ttctttgcag atggattta    1800
agtgttaaga gaattatcg gaagaatgtt gcctatcata attggagaca tgcctttaat    1860
acagctcagt gcatgtttgc cgctctaaaa gcaggcaaaa ttcagaacaa gctgactgac    1920
ctggagatac ttgcattgct gattgctgca ctaagccacg atttggatca ccgtggtgtg    1980
aataactctt acatacagcg aagtgaacat ccacttgccc agcttactg ccattcaatc    2040
atggaacacc atcattttga ccagtgcctg atgattctta atagtccagg caatcagatt    2100
ctcagtggcc tctccattga agaatataag accacgttga aataatcaa gcaagctatt    2160
```

```
ttagctacag acctagcact gtacattaag aggcgaggag aatttttga acttataaga    2220 aaaaatcaat tcaatttgga agatcctcat caaaaggagt tgttttggc aatgctgatg    2280 acagcttgtg atctttctgc aattacaaaa ccctggccta ttcaacaacg gatagcggaa    2340
cttgtagcaa ctgaattttt tgatcaagga gacagagaga gaaaagaact caacatagaa    2400
cccactgatc taatgaacag ggagaagaaa aacaaaatcc caagtatgca agttgggttc    2460
atagatgcca tctgcttgca actgtatgag gccctgaccc acgtgtcaga ggactgtttc    2520
cctttgctag atggctgcag aaagaacagg cagaaatggc aggcccttgc agaacagcag    2580
gagaagatgc tgattaatgg ggaaagcggc caggccaagc ggaac                   2625
```

<210> SEQ ID NO 11
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 11

```
Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Gln Met Lys His Glu Val Leu Cys Arg Trp
        50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270
```

```
Arg Glu Lys Lys Asn Lys Ile Pro Ser Met Gln Val Gly Phe Ile Asp
            275                 280                 285

Ala Ile Cys Leu Gln Leu Tyr Glu Ala Leu Thr His Val Ser Glu Asp
        290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 12
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 12
gaagaaacaa gagagctaca gtcgttagcg gctgctgtgg tgccatctgc ccagacccct      60
aaaattactg actttagctt cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaagaag aattatcgga agaatgttgc ctatcataat     240
tggagacatg cctttaatac agctcagtgc atgtttgccg ctctaaaagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ctttactgcc attcaatcat ggaacaccat cattttgacc agtgcctgat gattcttaat     480
agtccaggca atcagattct cagtggcctc tccattgaag aatataagac cacgttgaaa     540
ataatcaagc aagctatttt agctacagac ctagcactgt acattaagag gcgaggagaa     600
ttttttgaac ttataagaaa aaatcaattc aatttggaag atcctcatca aaaggagttg     660 ttttggcaa tgctgatgac agcttgtgat ctttctgcaa ttacaaaacc ctggcctatt     720
caacaacgga tagcggaact tgtagcaact gaatttttg atcaaggaga cagagagaga     780
aaagaactca acatagaacc cactgatcta atgaacaggg agaagaaaaa caaaatccca     840
agtatgcaag ttgggttcat agatgccatc tgcttgcaac tgtatgaggc cctgacccac     900
gtgtcagagg actgtttccc tttgctagat ggctgcagaa agaacaggca gaaatggcag     960
gcccttgcag aacagcag                                                  978

<210> SEQ ID NO 13
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 13

Glu Glu Thr Arg Glu Leu Gln Ser Leu Ala Ala Val Val Pro Ser
1               5                  10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
        35                  40                  45
```

```
Asn Leu Val Gln Asn Phe Arg Met Lys His Glu Val Leu Cys Arg Trp
 50                  55                  60

Ile Leu Ser Val Lys Lys Asn Tyr Arg Lys Asn Val Ala Tyr His Asn
 65                  70                  75                  80

Trp Arg His Ala Phe Asn Thr Ala Gln Cys Met Phe Ala Ala Leu Lys
                 85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
            195                 200                 205

Gln Phe Asn Leu Glu Asp Pro His Gln Lys Glu Leu Phe Leu Ala Met
210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270

Arg Glu Lys Lys Asn Lys Ile Pro Ser Met Gln Val Gly Phe Ile Asp
            275                 280                 285

Ala Ile Cys Leu Gln Leu Tyr Glu Ala Leu Thr His Val Ser Glu Asp
290                 295                 300

Cys Phe Pro Leu Leu Asp Gly Cys Arg Lys Asn Arg Gln Lys Trp Gln
305                 310                 315                 320

Ala Leu Ala Glu Gln Gln Glu Lys Met Leu Ile Asn Gly Glu Ser Gly
                325                 330                 335

Gln Ala Lys Arg Asn
            340
```

<210> SEQ ID NO 14
<211> LENGTH: 1026
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 14

```
gaagaaacaa gagagctaca gtcgttagcg gctgctgtgg tgccatctgc ccagacccctt      60 aaaattactg actttagctt cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaagaag aattatcgga agaatgttgc ctatcataat     240
tggagacatg cctttaatac agctcagtgc atgtttgccg ctctaaaagc aggcaaaatt     300
```

```
cagaacaagc tgactgacct ggagatactt gcattgctga ttgctgcact aagccacgat    360
ttggatcacc gtggtgtgaa taactcttac atacagcgaa gtgaacatcc acttgcccag    420
ctttactgcc attcaatcat ggaacaccat cattttgacc agtgcctgat gattcttaat    480
agtccaggca atcagattct cagtggcctc tccattgaag aatataagac cacgttgaaa    540
ataatcaagc aagctatttt agctacagac ctagcactgt acattaagag gcgaggagaa    600
ttttttgaac ttataagaaa aaatcaattc aatttggaag atcctcatca aaaggagttg    660
tttttggcaa tgctgatgac agcttgtgat ctttctgcaa ttacaaaacc ctggcctatt    720
caacaacgga tagcggaact tgtagcaact gaatttttg atcaaggaga cagagagaga    780
aaagaactca acatagaacc cactgatcta atgaacaggg agaagaaaaa caaaatccca    840
agtatgcaag ttgggttcat agatgccatc tgcttgcaac tgtatgaggc cctgacccac    900
gtgtcagagg actgtttccc tttgctagat ggctgcagaa agaacaggca gaaatggcag    960
gcccttgcag aacagcagga gaagatgctg attaatgggg aaagcggcca ggccaagcgg   1020
aactga                                                             1026
```

<210> SEQ ID NO 15
<211> LENGTH: 410
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 15

```
Gly Val Cys Gln Leu Val Asn Lys Met Glu Glu Asn Thr Gly Lys Val
1               5                   10                  15

Lys Pro Phe Asn Arg Asn Asp Glu Gln Phe Leu Glu Ala Phe Val Ile
            20                  25                  30

Phe Cys Gly Leu Gly Ile Gln Asn Thr Gln Met Tyr Glu Ala Val Glu
        35                  40                  45

Arg Ala Met Ala Lys Gln Met Val Thr Leu Glu Val Leu Ser Tyr His
    50                  55                  60

Ala Ser Ala Ala Glu Glu Thr Arg Glu Leu Gln Ser Leu Ala Ala
65                  70                  75                  80

Ala Val Val Pro Ser Ala Gln Thr Leu Lys Ile Thr Asp Phe Ser Phe
                85                  90                  95

Ser Asp Phe Glu Leu Ser Asp Leu Glu Thr Ala Leu Cys Thr Ile Arg
            100                 105                 110

Met Phe Thr Asp Leu Asn Leu Val Gln Asn Phe Arg Met Lys His Glu
        115                 120                 125

Val Leu Cys Arg Trp Ile Leu Ser Val Lys Lys Asn Tyr Arg Lys Asn
    130                 135                 140

Val Ala Tyr His Asn Trp Arg His Ala Phe Asn Thr Ala Gln Cys Met
145                 150                 155                 160

Phe Ala Ala Leu Lys Ala Gly Lys Ile Gln Asn Lys Leu Thr Asp Leu
                165                 170                 175

Glu Ile Leu Ala Leu Leu Ile Ala Ala Leu Ser His Asp Leu Asp His
            180                 185                 190

Arg Gly Val Asn Asn Ser Tyr Ile Gln Arg Ser Glu His Pro Leu Ala
        195                 200                 205

Gln Leu Tyr Cys His Ser Ile Met Glu His His His Phe Asp Gln Cys
    210                 215                 220
```

Leu Met Ile Leu Asn Ser Pro Gly Asn Gln Ile Ser Gly Leu Ser
225                 230                 235                 240

Ile Glu Glu Tyr Lys Thr Thr Leu Lys Ile Ile Lys Gln Ala Ile Leu
            245                 250                 255

Ala Thr Asp Leu Ala Leu Tyr Ile Lys Arg Arg Gly Glu Phe Phe Glu
            260                 265                 270

Leu Ile Arg Lys Asn Gln Phe Asn Leu Glu Asp Pro His Gln Lys Glu
        275                 280                 285

Leu Phe Leu Ala Met Leu Met Thr Ala Cys Asp Leu Ser Ala Ile Thr
    290                 295                 300

Lys Pro Trp Pro Ile Gln Gln Arg Ile Ala Glu Leu Val Ala Thr Glu
305                 310                 315                 320

Phe Phe Asp Gln Gly Asp Arg Glu Arg Lys Glu Leu Asn Ile Glu Pro
                325                 330                 335

Thr Asp Leu Met Asn Arg Glu Lys Lys Asn Lys Ile Pro Ser Met Gln
            340                 345                 350

Val Gly Phe Ile Asp Ala Ile Cys Leu Gln Leu Tyr Glu Ala Leu Thr
        355                 360                 365

His Val Ser Glu Asp Cys Phe Pro Leu Leu Asp Gly Cys Arg Lys Asn
    370                 375                 380

Arg Gln Lys Trp Gln Ala Leu Ala Glu Gln Gln Glu Lys Met Leu Ile
385                 390                 395                 400

Asn Gly Glu Ser Gly Gln Ala Lys Arg Asn
                405                 410

<210> SEQ ID NO 16
<211> LENGTH: 1233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 16
ggggtttgcc aacttgttaa taagatggag gagaatactg gcaaggttaa gccttttcaac      60 cgaaatgacg aacagttttct ggaagctttt gtcatcttttt gtggcttggg gatccagaac    120
acgcagatgt atgaagcagt ggagagagcc atggccaagc aaatggtcac attggaggtt     180
ctgtcgtatc atgcttcagc agcagaggaa gaaacaagag agctacagtc gttagcggct     240
gctgtggtgc catctgccca gacccttaaa attactgact ttagcttcag tgactttgag     300
ctgtctgatc tggaaacagc actgtgtaca attcggatgt tactgacct caaccttgtg     360 cagaacttcc ggatgaaaca tgaggttctt gcagatgga ttttaagtgt taagaagaat     420
tatcggaaga atgttgccta tcataattgg agacatgcct taatacagc tcagtgcatg      480 tttgccgctc taaagcagg caaaattcag aacaagctga ctgacctgga gatacttgca      540
ttgctgattg ctgcactaag ccacgattttg gatcaccgtg gtgtgaataa ctcttacata    600
cagcgaagtg aacatccact tgcccagctt tactgccatt caatcatgga acaccatcat     660
tttgaccagt gcctgatgat tcttaatagt ccaggcaatc agattctcag tggcctctcc     720
attgaagaat ataagaccac gttgaaaata atcaagcaag ctatttttagc tacagaccta   780 gcactgtaca ttaagaggcg aggagaattt tttgaactta agaaaaaaa tcaattcaat     840 ttggaagatc ctcatcaaaa ggagttgttt ttggcaatgc tgatgacagc ttgtgatctt   900

-continued

```
tctgcaatta caaaaccctg gcctattcaa caacggatag cggaacttgt agcaactgaa      960
ttttttgatc aaggagacag agagagaaaa gaactcaaca tagaacccac tgatctaatg     1020
aacagggaga gaaaaacaa atcccaagt atgcaagttg ggttcataga tgccatctgc      1080
ttgcaactgt atgaggccct gacccacgtg tcagaggact gtttcccttt gctagatggc     1140
tgcagaaaga acaggcagaa atggcaggcc cttgcagaac agcaggagaa gatgctgatt     1200
aatggggaaa gcggccaggc caagcggaac tga                                  1233
```

<210> SEQ ID NO 17
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 17

```
Glu Pro Leu Asn Ile Pro Asp Val Ser Lys Asp Lys Arg Phe Pro Trp
1               5                   10                  15

Thr Thr Glu Asn Thr Gly Asn Val Asn Gln Gln Cys Ile Arg Ser Leu
            20                  25                  30

Leu Cys Thr Pro Ile Lys Asn Gly Lys Lys Asn Lys Val Ile Gly Val
        35                  40                  45

Cys Gln Leu Val Asn Lys Met Glu Glu Asn Thr Gly Lys Val Lys Pro
    50                  55                  60

Phe Asn Arg Asn Asp Glu Gln Phe Leu Glu Ala Phe Val Ile Phe Cys
65                  70                  75                  80

Gly Leu Gly Ile Gln Asn Thr Gln Met Tyr Glu Ala Val Glu Arg Ala
                85                  90                  95

Met Ala Lys Gln Met Val Thr Leu Glu Val Leu Ser Tyr His Ala Ser
            100                 105                 110

Ala Ala Glu Glu Glu Thr Arg Glu Leu Gln Ser Leu Ala Ala Ala Val
        115                 120                 125

Val Pro Ser Ala Gln Thr Leu Lys Ile Thr Asp Phe Ser Phe Ser Asp
    130                 135                 140

Phe Glu Leu Ser Asp Leu Glu Thr Ala Leu Cys Thr Ile Arg Met Phe
145                 150                 155                 160

Thr Asp Leu Asn Leu Val Gln Asn Phe Arg Met Lys His Glu Val Leu
                165                 170                 175

Cys Arg Trp Ile Leu Ser Val Lys Lys Asn Tyr Arg Lys Asn Val Ala
            180                 185                 190

Tyr His Asn Trp Arg His Ala Phe Asn Thr Ala Gln Cys Met Phe Ala
        195                 200                 205

Ala Leu Lys Ala Gly Lys Ile Gln Asn Lys Leu Thr Asp Leu Glu Ile
    210                 215                 220

Leu Ala Leu Leu Ile Ala Ala Leu Ser His Asp Leu Asp His Arg Gly
225                 230                 235                 240

Val Asn Asn Ser Tyr Ile Gln Arg Ser Glu His Pro Leu Ala Gln Leu
                245                 250                 255

Tyr Cys His Ser Ile Met Glu His His His Phe Asp Gln Cys Leu Met
            260                 265                 270

Ile Leu Asn Ser Pro Gly Asn Gln Ile Leu Ser Gly Leu Ser Ile Glu
        275                 280                 285

Glu Tyr Lys Thr Thr Leu Lys Ile Ile Lys Gln Ala Ile Leu Ala Thr
```

```
                290                 295                 300
Asp Leu Ala Leu Tyr Ile Lys Arg Arg Gly Glu Phe Phe Glu Leu Ile
305                 310                 315                 320

Arg Lys Asn Gln Phe Asn Leu Glu Asp Pro His Gln Lys Glu Leu Phe
                325                 330                 335

Leu Ala Met Leu Met Thr Ala Cys Asp Leu Ser Ala Ile Thr Lys Pro
            340                 345                 350

Trp Pro Ile Gln Gln Arg Ile Ala Glu Leu Val Ala Thr Glu Phe Phe
        355                 360                 365

Asp Gln Gly Asp Arg Glu Arg Lys Glu Leu Asn Ile Glu Pro Thr Asp
    370                 375                 380

Leu Met Asn Arg Glu Lys Lys Asn Lys Ile Pro Ser Met Gln Val Gly
385                 390                 395                 400

Phe Ile Asp Ala Ile Cys Leu Gln Leu Tyr Glu Ala Leu Thr His Val
                405                 410                 415

Ser Glu Asp Cys Phe Pro Leu Leu Asp Gly Cys Arg Lys Asn Arg Gln
            420                 425                 430

Lys Trp Gln Ala Leu Ala Glu Gln Gln Glu Lys Met Leu Ile Asn Gly
        435                 440                 445

Glu Ser Gly Gln Ala Lys Arg Asn
    450                 455

<210> SEQ ID NO 18
<211> LENGTH: 1371
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 18
gaaccactta atatcccaga tgtcagtaag gataaaagat ttccctggac aactgaaaat      60
acaggaaatg taaaccagca gtgcattaga agtttgcttt gtacacctat aaaaaatgga    120
aagaagaata aagttatagg ggtttgccaa cttgttaata agatggagga gaatactggc    180
aaggttaagc cttcaaccg aaatgacgaa cagtttctgg aagcttttgt catcttttgt      240
ggcttgggga tccagaacac gcagatgtat gaagcagtgg agagagccat ggccaagcaa    300
atggtcacat tggaggttct gtcgtatcat gcttcagcag cagaggaaga aacaagagag    360
ctacagtcgt tagcggctgc tgtggtgcca tctgcccaga cccttaaaat tactgacttt    420
agcttcagtg actttgagct gtctgatctg gaaacagcac tgtgtacaat tcggatgttt    480
actgacctca accttgtgca gaacttccgg atgaaacatg aggttctttg cagatggatt    540
ttaagtgtta agaagaatta tcggaagaat gttgcctatc ataattggag acatgccttt    600
aatacagctc agtgcatgtt tgccgctcta aaagcaggca aaattcagaa caagctgact    660
gacctggaga tacttgcatt gctgattgct gcactaagcc acgatttgga tcaccgtggt    720
gtgaataact cttacataca gcgaagtgaa catccacttg cccagcttta ctgccattca    780
atcatggaac accatcattt tgaccagtgc ctgatgattc ttaatagtcc aggcaatcag    840
attctcagtg gcctctccat tgaagaatat aagaccacgt tgaaaataat caagcaagct    900
attttagcta cagacctagc actgtacatt aagaggcgag agaattttt tgaacttata    960 agaaaaaatc aattcaattt ggaagatcct catcaaaagg agttgttttt ggcaatgctg    1020
atgacagctt gtgatctttc tgcaattaca aaaccctggc ctattcaaca acggatagcg    1080
```

```
gaacttgtag caactgaatt ttttgatcaa ggagacagag agagaaaaga actcaacata   1140
gaacccactg atctaatgaa cagggagaag aaaaacaaaa tcccaagtat gcaagttggg   1200
ttcatagatg ccatctgctt gcaactgtat gaggccctga cccacgtgtc agaggactgt   1260
ttccctttgc tagatggctg cagaaagaac aggcagaaat ggcaggccct tgcagaacag   1320
caggagaaga tgctgattaa tggggaaagc ggccaggcca agcggaactg a           1371
```

<210> SEQ ID NO 19
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 19

```
Met Glu Glu Thr Arg Glu Leu Gln Ser Leu Ala Ala Val Val Pro
1               5                   10                  15

Ser Ala Gln Thr Leu Lys Ile Thr Asp Phe Ser Phe Ser Asp Phe Glu
            20                  25                  30

Leu Ser Asp Leu Glu Thr Ala Leu Cys Thr Ile Arg Met Phe Thr Asp
        35                  40                  45

Leu Asn Leu Val Gln Asn Phe Arg Met Lys His Glu Val Leu Cys Arg
    50                  55                  60

Trp Ile Leu Ser Val Lys Lys Asn Tyr Arg Lys Asn Val Ala Tyr His
65                  70                  75                  80

Asn Trp Arg His Ala Phe Asn Thr Ala Gln Cys Met Phe Ala Ala Leu
                85                  90                  95

Lys Ala Gly Glu Ile Gln Asn Lys Leu Thr Asp Leu Glu Ile Leu Ala
            100                 105                 110

Leu Leu Ile Ala Ala Leu Ser His Asp Leu Asp His Arg Gly Val Asn
        115                 120                 125

Asn Ser Tyr Ile Gln Arg Ser Glu His Pro Leu Ala Gln Leu Tyr Cys
    130                 135                 140

His Ser Ile Met Glu His His His Phe Asp Gln Cys Leu Met Ile Leu
145                 150                 155                 160

Asn Ser Pro Gly Asn Gln Ile Leu Ser Gly Leu Ser Ile Glu Glu Tyr
                165                 170                 175

Lys Thr Ser Leu Lys Ile Ile Lys Gln Ala Ile Leu Ala Thr Asp Leu
            180                 185                 190

Ala Leu Tyr Ile Lys Arg Arg Gly Glu Phe Phe Glu Leu Ile Arg Lys
        195                 200                 205

Asn Gln Phe Asn Leu Glu Asp Pro His Gln Lys Glu Leu Phe Leu Ala
    210                 215                 220

Met Leu Met Thr Ala Cys Asp Leu Ser Ala Ile Thr Lys Pro Trp Pro
225                 230                 235                 240

Ile Gln Gln Arg Ile Ala Glu Leu Val Ala Thr Glu Phe Phe Asp Gln
                245                 250                 255

Gly Asp Arg Glu Arg Glu Glu Leu Asn Ile Glu Pro Thr Asp Leu Met
            260                 265                 270

Asn Arg Glu Lys Lys Asn Lys Ile Pro Ser Met Gln Val Gly Phe Ile
        275                 280                 285

Asp Ala Ile Cys Leu Gln Leu Tyr Glu Ala Leu Thr His Val Ser Glu
    290                 295                 300
```

```
Asp Cys Phe Pro Leu Leu Asp Gly Cys Arg Lys Asn Arg Gln Glu Trp
305                 310                 315                 320

Gln Ala Leu Ala Glu Gln Gln
                325
```

<210> SEQ ID NO 20
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 20

```
Met Glu Gly Thr Arg Glu Leu Gln Ser Leu Ala Ala Val Val Pro
1               5                   10                  15

Ser Ala Gln Thr Leu Lys Ile Thr Asp Phe Ser Phe Ser Asp Phe Glu
                20                  25                  30

Leu Ser Asp Leu Glu Thr Ala Leu Cys Thr Ile Arg Met Phe Thr Asp
                35                  40                  45

Leu Asn Leu Val Gln Asn Phe Arg Met Lys His Glu Val Leu Cys Arg
50                  55                  60

Trp Ile Leu Ser Val Lys Lys Asn Tyr Arg Lys Asn Val Ala Tyr His
65                  70                  75                  80

Asn Trp Arg His Ala Phe Asn Thr Ala Gln Cys Met Phe Ala Ala Leu
                85                  90                  95

Lys Ala Gly Lys Ile Gln Asn Lys Leu Thr Asp Leu Glu Ile Leu Ala
                100                 105                 110

Leu Leu Ile Ala Ala Leu Ser His Asp Leu Asp His Arg Gly Val Asn
                115                 120                 125

Asn Ser Tyr Ile Gln Arg Ser Glu His Pro Leu Ala Gln Leu Tyr Cys
130                 135                 140

His Ser Ile Met Glu His His His Phe Asp Gln Cys Leu Met Ile Leu
145                 150                 155                 160

Asn Ser Pro Gly Asn Gln Ile Leu Ser Gly Leu Ser Ile Glu Glu Tyr
                165                 170                 175

Lys Thr Thr Leu Lys Ile Ile Lys Gln Ala Ile Leu Ala Thr Asp Leu
                180                 185                 190

Ala Leu Tyr Ile Lys Arg Arg Gly Glu Phe Phe Glu Leu Ile Arg Lys
                195                 200                 205

Asn Gln Phe Asn Leu Glu Asp Pro His Gln Lys Glu Leu Phe Leu Ala
                210                 215                 220

Met Leu Met Thr Ala Cys Asp Leu Ser Ala Ile Thr Lys Pro Trp Pro
225                 230                 235                 240

Ile Gln Gln Arg Ile Ala Glu Leu Val Ala Thr Glu Phe Phe Asp Gln
                245                 250                 255

Gly Asp Arg Glu Arg Lys Glu Leu Asn Ile Glu Pro Thr Asp Leu Met
                260                 265                 270

Asn Arg Glu Lys Lys Asn Lys Ile Pro Ser Met Gln Val Gly Phe Ile
                275                 280                 285

Asp Ala Ile Cys Leu Gln Leu Tyr Glu Ala Leu Thr His Val Ser Glu
                290                 295                 300

Asp Ser Phe Pro Leu Leu Asp Gly Cys Arg Lys Asn Arg Gln Lys Trp
305                 310                 315                 320
```

Gln Ala Leu Ala Glu Gln Gln
            325

<210> SEQ ID NO 21
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 21

Met Glu Glu Thr Arg Glu Leu Gln Ser Leu Ala Ala Val Val Pro
1               5                   10                  15

Ser Ala Gln Thr Leu Lys Ile Thr Asp Phe Ser Phe Ser Asp Phe Glu
                20                  25                  30

Leu Ser Asp Leu Glu Thr Ala Leu Cys Thr Ile Arg Met Phe Thr Asp
                35                  40                  45

Leu Asn Leu Val Gln Ser Phe Arg Met Lys His Glu Val Leu Cys Arg
            50                  55                  60

Trp Ile Leu Ser Val Lys Lys Asn Tyr Arg Glu Asn Val Ala Tyr His
65                  70                  75                  80

Asn Trp Arg His Ala Phe Asn Thr Ala Gln Cys Met Phe Ala Ala Leu
                85                  90                  95

Lys Ala Gly Lys Ile Gln Asn Lys Leu Thr Asp Leu Glu Ile Leu Ala
                100                 105                 110

Leu Leu Ile Ala Ala Leu Ser His Asp Leu Asp His Arg Gly Val Ser
            115                 120                 125

Asn Ser Tyr Ile Gln Arg Ser Glu His Pro Leu Ala Gln Leu Tyr Cys
            130                 135                 140

His Ser Ile Met Glu His His His Phe Asp Gln Cys Leu Met Ile Leu
145                 150                 155                 160

Asn Ser Pro Gly Asn Gln Ile Leu Ser Gly Leu Ser Ile Glu Glu Tyr
                165                 170                 175

Lys Thr Thr Leu Lys Ile Ile Lys Gln Ala Ile Leu Ala Thr Asp Leu
                180                 185                 190

Ala Leu Tyr Ile Lys Arg Arg Gly Glu Phe Phe Glu Leu Ile Arg Lys
            195                 200                 205

Asn Gln Phe Asn Leu Glu Asp Pro His Gln Lys Glu Leu Phe Leu Ala
            210                 215                 220

Met Leu Met Thr Ala Cys Val Leu Ser Ala Ile Thr Lys Pro Trp Pro
225                 230                 235                 240

Ile Gln Gln Arg Ile Ala Glu Leu Val Ala Thr Glu Phe Phe Asp Gln
                245                 250                 255

Gly Asp Arg Glu Arg Lys Glu Leu Asn Ile Glu Pro Thr Asp Leu Met
                260                 265                 270

Asn Arg Glu Lys Lys Asn Lys Ile Pro Ser Met Gln Val Gly Phe Ile
            275                 280                 285

Asp Ala Ile Cys Leu Gln Leu Tyr Glu Ala Leu Thr His Val Ser Glu
            290                 295                 300

Asp Cys Phe Pro Leu Leu Asp Gly Cys Arg Lys Asn Arg Gln Lys Trp
305                 310                 315                 320

Gln Ala Leu Ala Glu Gln Gln
            325

<210> SEQ ID NO 22
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 22

```
Met Glu Glu Thr Arg Glu Leu Gln Ser Leu Ala Ala Val Val Pro
1               5                   10                  15

Ser Ala Gln Thr Leu Lys Ile Thr Asp Phe Ser Phe Ser Asp Phe Glu
                20                  25                  30

Leu Ser Asp Leu Glu Thr Ala Leu Cys Thr Ile Arg Met Phe Thr Asp
            35                  40                  45

Leu Asn Leu Val Gln Asn Phe Arg Met Lys His Glu Val Leu Cys Arg
        50                  55                  60

Trp Ile Leu Ser Val Lys Lys Asn Tyr Arg Lys Asn Val Ala Tyr His
65                  70                  75                  80

Asn Trp Arg His Ala Phe Asn Thr Ala Gln Cys Met Phe Ala Ala Leu
                85                  90                  95

Lys Ala Gly Lys Ile Gln Asn Lys Leu Thr Asp Leu Glu Ile Leu Ala
                100                 105                 110

Leu Leu Ile Ala Ala Leu Ser His Asp Leu Asp His Arg Gly Val Asn
            115                 120                 125

Asn Ser Tyr Ile Gln Arg Ser Glu His Pro Leu Ala Gln Pro Tyr Cys
        130                 135                 140

His Ser Ile Met Glu His His His Phe Asp Gln Cys Leu Met Ile Leu
145                 150                 155                 160

Asn Ser Pro Gly Asn Gln Ile Leu Ser Gly Leu Ser Ile Glu Glu Tyr
                165                 170                 175

Lys Thr Thr Leu Lys Ile Ile Lys Gln Ala Ile Leu Ala Thr Asp Leu
                180                 185                 190

Ala Leu Tyr Ile Lys Arg Arg Gly Glu Phe Phe Glu Leu Ile Arg Lys
            195                 200                 205

Asn Gln Phe Asn Leu Glu Asp Pro His Gln Lys Glu Leu Leu Leu Ala
        210                 215                 220

Met Leu Met Thr Ala Cys Asp Leu Ser Ala Ile Thr Lys Pro Trp Pro
225                 230                 235                 240

Ile Gln Gln Arg Ile Ala Glu Leu Val Ala Thr Glu Phe Phe Asp Gln
                245                 250                 255

Gly Asp Arg Glu Arg Lys Glu Leu Asn Ile Glu Pro Thr Asp Leu Met
                260                 265                 270

Asn Arg Glu Lys Lys Asn Lys Ile Pro Ser Met Gln Val Gly Phe Ile
            275                 280                 285

Asp Ala Ile Cys Leu Gln Leu Tyr Glu Ala Leu Thr His Val Ser Glu
        290                 295                 300

Asp Cys Phe Pro Leu Leu Asp Gly Cys Arg Lys Asn Arg Gln Lys Trp
305                 310                 315                 320

Gln Ala Leu Ala Glu Gln Gln
                325
```

<210> SEQ ID NO 23
<211> LENGTH: 326
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic Destabilizing Domain (DD)"

<400> SEQUENCE: 23
```

| | | | | | | | | | | | | | | |
|---|---|---|---|---|---|---|---|---|---|---|---|---|---|---|
| Glu | Glu | Thr | Arg | Glu | Leu | Gln | Ser | Leu | Ala | Ala | Val | Val | Pro | Ser |
| 1 | | | | 5 | | | | | 10 | | | | | 15 |
| Ala | Gln | Thr | Leu | Lys | Ile | Thr | Asp | Phe | Ser | Phe | Ser | Asp | Phe | Glu | Leu |
| | | | 20 | | | | | 25 | | | | | 30 | | |
| Ser | Asp | Leu | Glu | Thr | Ala | Leu | Cys | Thr | Ile | Arg | Met | Phe | Thr | Asp | Leu |
| | | 35 | | | | | 40 | | | | | 45 | | | |
| Asn | Leu | Val | Gln | Asn | Phe | Arg | Met | Lys | His | Glu | Val | Leu | Cys | Arg | Trp |
| 50 | | | | | 55 | | | | | 60 | | | | | |
| Ile | Leu | Ser | Val | Lys | Lys | Asn | Tyr | Arg | Lys | Asn | Val | Ala | Tyr | His | Asn |
| 65 | | | | 70 | | | | | 75 | | | | | 80 | |
| Trp | Arg | His | Ala | Phe | Asn | Thr | Ala | Gln | Cys | Met | Phe | Ala | Ala | Leu | Lys |
| | | | 85 | | | | | 90 | | | | | 95 | | |
| Ala | Gly | Lys | Ile | Gln | Asn | Lys | Leu | Thr | Asp | Leu | Glu | Ile | Leu | Ala | Leu |
| | | 100 | | | | | 105 | | | | | 110 | | | |
| Leu | Ile | Ala | Ala | Leu | Ser | His | Asp | Leu | Asp | His | Arg | Gly | Val | Asn | Asn |
| | 115 | | | | | 120 | | | | | 125 | | | | |
| Ser | Tyr | Ile | Gln | Arg | Ser | Glu | His | Pro | Leu | Ala | Gln | Leu | Tyr | Cys | His |
| 130 | | | | | 135 | | | | | 140 | | | | | |
| Ser | Ile | Met | Glu | His | His | His | Phe | Ala | Gln | Cys | Leu | Met | Ile | Leu | Asn |
| 145 | | | | 150 | | | | | 155 | | | | | 160 | |
| Ser | Pro | Gly | Asn | Gln | Ile | Leu | Ser | Gly | Leu | Ser | Ile | Glu | Glu | Tyr | Lys |
| | | | 165 | | | | | 170 | | | | | 175 | | |
| Thr | Thr | Leu | Lys | Ile | Ile | Lys | Gln | Ala | Ile | Leu | Ala | Thr | Asp | Leu | Ala |
| | | 180 | | | | | 185 | | | | | 190 | | | |
| Leu | Tyr | Ile | Lys | Arg | Arg | Gly | Glu | Phe | Phe | Glu | Leu | Ile | Arg | Lys | Asn |
| | 195 | | | | | 200 | | | | | 205 | | | | |
| Gln | Phe | Asn | Leu | Glu | Asp | Pro | His | Gln | Lys | Glu | Leu | Phe | Leu | Ala | Met |
| 210 | | | | | 215 | | | | | 220 | | | | | |
| Leu | Met | Thr | Ala | Cys | Asn | Leu | Ser | Ala | Ile | Thr | Lys | Pro | Trp | Pro | Ile |
| 225 | | | | 230 | | | | | 235 | | | | | 240 | |
| Gln | Gln | Arg | Ile | Ala | Glu | Leu | Val | Ala | Thr | Glu | Phe | Phe | Asp | Gln | Gly |
| | | | 245 | | | | | 250 | | | | | 255 | | |
| Asp | Arg | Glu | Arg | Lys | Glu | Leu | Asn | Ile | Glu | Pro | Thr | Asp | Leu | Met | Asn |
| | | 260 | | | | | 265 | | | | | 270 | | | |
| Arg | Glu | Lys | Lys | Asn | Lys | Ile | Pro | Cys | Met | Gln | Val | Gly | Phe | Ile | Asp |
| | 275 | | | | | 280 | | | | | 285 | | | | |
| Ala | Ile | Cys | Leu | Gln | Leu | Tyr | Glu | Ala | Leu | Thr | His | Val | Ser | Glu | Asp |
| 290 | | | | | 295 | | | | | 300 | | | | | |
| Cys | Phe | Pro | Leu | Leu | Asp | Gly | Cys | Arg | Lys | Asn | Arg | Gln | Lys | Trp | Gln |
| 305 | | | | 310 | | | | | 315 | | | | | 320 | |
| Ala | Leu | Ala | Glu | Gln | Gln |
| | | | 325 | | |

```
<210> SEQ ID NO 24
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"
```

<400> SEQUENCE: 24

```
Glu Glu Thr Arg Glu Leu Gln Ser Leu Ala Ala Ala Val Val Pro Ser
1               5                   10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Arg Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Asp Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu His Ile Arg Lys Asn
        195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
                325
```

<210> SEQ ID NO 25
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 25

```
Glu Glu Thr Arg Glu Leu Gln Ser Leu Ala Ala Ala Val Val Pro Ser
```

```
              1               5                  10                 15
Ala Gln Thr Leu Lys Ile Thr Asp Phe Ser Phe Ser Asp Phe Glu Leu
                        20                  25                 30

Ser Asp Leu Glu Thr Ala Leu Cys Thr Ile Arg Met Phe Thr Asp Leu
                        35                  40                 45

Asn Leu Val Gln Asn Phe Arg Met Glu His Glu Val Leu Cys Arg Trp
             50                  55                 60

Ile Leu Ser Val Lys Lys Asn Tyr Arg Lys His Val Ala Tyr His Asn
65                       70                  75                 80

Trp Arg His Ala Phe Asn Thr Ala Gln Cys Met Phe Ala Ala Leu Lys
                        85                  90                 95

Ala Gly Lys Ile Gln Asn Lys Leu Thr Asp Leu Glu Ile Leu Ala Leu
                       100                 105                110

Leu Ile Ala Ala Leu Ser His Asp Leu Asp His Arg Gly Val Asn Asn
                       115                 120                125

Ser Tyr Ile Gln Arg Ser Glu His Pro Leu Ala Gln Leu Tyr Cys His
            130                 135                140

Ser Ile Met Glu His His His Phe Asp Gln Cys Leu Met Ile Leu Asn
145                     150                 155                160

Ser Pro Gly Asn Gln Ile Leu Ser Gly Leu Ser Ile Glu Glu Tyr Lys
                       165                 170                175

Thr Thr Leu Lys Ile Ile Lys Gln Ala Ile Leu Ala Thr Asp Leu Ala
                       180                 185                190

Leu Tyr Ile Lys Arg Arg Gly Glu Phe Phe Glu Leu Ile Arg Lys Asn
            195                 200                205

Gln Phe Asn Leu Glu Asp Pro His Gln Lys Glu Leu Phe Leu Ala Met
            210                 215                220

Leu Met Thr Ala Cys Val Leu Ser Ala Ile Thr Lys Pro Trp Pro Ile
225                     230                 235                240

Gln Gln Arg Ile Ala Glu Leu Val Ala Thr Glu Phe Phe Asp Gln Gly
                       245                 250                255

Asp Arg Glu Arg Lys Glu Leu Asn Ile Glu Pro Thr Asp Leu Met Asn
                       260                 265                270

Arg Glu Lys Lys Asn Lys Ile Pro Ser Met Gln Val Gly Phe Ile Asp
            275                 280                285

Ala Ile Cys Leu Gln Leu Tyr Glu Ala Leu Thr His Val Ser Glu Asp
            290                 295                300

Cys Phe Pro Leu Leu Asp Gly Cys Arg Lys Asn Arg Gln Lys Trp Gln
305                     310                 315                320

Ala Leu Ala Glu Gln Gln
                       325
```

<210> SEQ ID NO 26
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 26

```
              1               5                  10                 15
Glu Glu Thr Arg Glu Leu Gln Ser Leu Ala Ala Ala Val Val Pro Ser

Ala Gln Thr Leu Lys Ile Thr Asp Phe Ser Phe Ser Asp Phe Glu Leu
                        20                  25                 30
```

```
Ser Asp Leu Glu Thr Ala Leu Cys Thr Ile Arg Met Phe Thr Asp Leu
        35                  40                  45

Asn Leu Val Gln Asn Phe Arg Met Lys His Glu Val Leu Cys Arg Trp
 50                  55                  60

Ile Leu Ser Val Lys Lys Asn Tyr Arg Lys Asn Val Ala Tyr His Asn
 65                  70                  75                  80

Trp Arg His Ala Phe Asn Thr Ala Gln Cys Met Phe Ala Ala Leu Lys
                 85                  90                  95

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
                115                 120                 125

Ser Tyr Ile Gln Arg Ser Glu His Pro Leu Ala Gln Leu Tyr Cys His
                130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
                180                 185                 190

Leu Tyr Ile Lys Arg Arg Gly Glu Phe Phe Glu Leu Ile Arg Lys Asn
                195                 200                 205

Gln Phe Asn Leu Glu Asp Pro His Gln Lys Glu Leu Phe Leu Ala Met
                210                 215                 220

Leu Met Thr Ala Cys Gly Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
                260                 265                 270

Arg Glu Lys Lys Asn Lys Ile Pro Ser Met Gln Val Gly Phe Ile Asp
                275                 280                 285

Ala Ile Cys Leu Gln Leu Tyr Glu Ala Leu Thr His Val Ser Glu Asp
                290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 27
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 27

Glu Glu Thr Arg Glu Leu Gln Ser Leu Ala Ala Val Val Pro Ser
1               5                   10                  15

Ala Gln Thr Leu Lys Ile Thr Asp Phe Ser Leu Ser Asp Phe Glu Leu
                20                  25                  30

Ser Asp Leu Glu Thr Ala Leu Cys Thr Ile Arg Met Phe Thr Asp Leu
                35                  40                  45
```

```
Asn Leu Val Gln Asn Phe Arg Met Lys His Glu Val Leu Cys Arg Trp
 50                  55                  60

Ile Leu Ser Val Lys Glu Asn Tyr Arg Lys Asn Val Ala Tyr His Asn
 65                  70                  75                  80

Trp Arg His Ala Phe Asn Thr Ala Gln Cys Met Phe Ala Ala Leu Lys
                 85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asn Leu Ala
            180                 185                 190

Leu Tyr Ile Lys Arg Arg Gly Glu Phe Phe Glu Leu Ile Arg Lys Asn
    195                 200                 205

Gln Phe Asn Leu Glu Asp Pro His Gln Lys Glu Leu Phe Leu Ala Met
210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Phe Asn Ile Glu Pro Thr Asp Leu Met Asn
            260                 265                 270

Arg Glu Lys Lys Asn Lys Ile Pro Ser Met Gln Val Gly Phe Ile Asp
    275                 280                 285

Ala Ile Cys Leu Gln Leu Tyr Glu Ala Leu Thr His Val Ser Glu Asp
290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 28
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 28

Asp Glu Thr Arg Glu Leu Gln Ser Leu Ala Ala Val Val Pro Ser
 1               5                  10                  15

Ala Gln Thr Leu Arg Ile Thr Asp Phe Ser Phe Ser Asp Ser Glu Leu
                 20                  25                  30

Ser Asp Leu Glu Thr Ala Leu Cys Thr Ile Arg Met Phe Thr Asp Leu
             35                  40                  45

Asn Leu Val Gln Asn Phe Arg Met Lys His Glu Val Leu Cys Arg Trp
 50                  55                  60

Ile Leu Ser Val Lys Lys Asn Tyr Arg Lys Asn Val Ala Tyr His Asn
```

```
                    65                  70                  75                  80
Trp Arg His Ala Phe Asn Thr Ala Gln Cys Met Phe Ala Ala Leu Arg
                    85                  90                  95

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
                115                 120                 125

Ser Tyr Ile Gln Arg Ser Glu His Pro Leu Ala Gln Leu Tyr Arg His
                130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
                180                 185                 190

Leu Tyr Ile Lys Arg Arg Gly Glu Phe Phe Glu Leu Ile Arg Lys Ser
                195                 200                 205

Gln Phe Asn Leu Glu Asp Pro His Gln Lys Glu Leu Phe Leu Ala Met
                210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Thr Glu Pro Thr Asp Leu Met Asn
                260                 265                 270

Arg Glu Lys Lys Asn Lys Ile Pro Ser Ala Gln Val Gly Phe Ile Asp
                275                 280                 285

Ala Ile Cys Leu Gln Leu Tyr Glu Ala Leu Thr His Val Ser Glu Asp
                290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 29
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 29

Glu Glu Thr Arg Glu Leu Gln Ser Leu Ala Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
                35                  40                  45

Asn Leu Val Gln Asn Phe Arg Met Lys His Glu Val Leu Cys Arg Trp
                50                  55                  60

Ile Leu Ser Val Lys Lys Asn Tyr Arg Lys His Val Ala Tyr His Asn
65                  70                  75                  80

Trp Arg His Ala Phe Asn Thr Ala Gln Cys Met Phe Ala Ala Leu Lys
                85                  90                  95
```

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Asn Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
    195                 200                 205

Gln Phe Asn Leu Glu Asp Pro His Gln Lys Glu Leu Phe Leu Ala Met
210                 215                 220

Leu Met Thr Ser Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270

Arg Glu Lys Lys Asn Lys Ile Pro Ser Met Gln Val Gly Phe Ile Asp
    275                 280                 285

Ala Ile Cys Leu Gln Leu Tyr Glu Ala Leu Thr His Val Ser Glu Asp
290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 30
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 30

Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Ser Lys Leu Thr Asp Leu Glu Ile Leu Ala Leu
                100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
            130                 135                 140

Ser Ile Met Glu His His His Phe Ala Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
            195                 200                 205

Gln Phe Asn Leu Glu Asp Pro His Gln Lys Glu Leu Phe Leu Ala Met
    210                 215                 220

Leu Met Thr Ala Cys Asn Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270

Arg Glu Lys Lys Asn Lys Ile Pro Cys Met Gln Val Gly Phe Ile Asp
            275                 280                 285

Ala Ile Cys Leu Gln Leu Tyr Glu Ala Leu Thr His Val Ser Glu Asp
            290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 31
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 31

Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
50                  55                  60

Val Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His

```
            130                 135                 140
Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Ala Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Leu Asn Ser Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Pro Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 32
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 32

Glu Glu Thr Arg Glu Leu Gln Ser Leu Ala Ala Val Val Pro Ser
1               5                   10                  15

Ala Gln Thr Leu Lys Ile Thr Asp Phe Gly Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Ala Gln Ser Phe Arg Met Glu His Glu Val Leu Cys Arg Trp
        50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Pro Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160
```

Ser Pro Gly Asn Gln Ile Leu Ser Gly Leu Ser Ile Glu Glu Tyr Lys
            165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
            195                 200                 205

Gln Phe Asn Leu Glu Asp Pro His Gln Lys Glu Leu Phe Leu Ala Met
210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
                260                 265                 270

Arg Glu Lys Lys Asn Lys Ile Pro Ser Met Gln Val Gly Phe Ile Asp
                275                 280                 285

Ala Ile Cys Leu Gln Leu Tyr Glu Ala Leu Thr His Val Ser Glu Asp
                290                 295                 300

Cys Ser Pro Leu Leu Asp Gly Cys Arg Lys Asn Arg Gln Lys Trp Gln
305                 310                 315                 320

Ala Leu Ala Glu Gln Gln
                325

<210> SEQ ID NO 33
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic Destabilizing Domain (DD)"

<400> SEQUENCE: 33

Glu Glu Thr Arg Glu Leu Gln Ser Leu Ala Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
                100                 105                 110

Leu Val Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
        130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
            165                 170                 175

```
Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
            245                 250                 255

Asp Arg Glu Arg Lys Glu Leu Asn Ile Glu Pro Thr Asp Leu Met Asn
        260                 265                 270

Arg Glu Lys Lys Asn Lys Ile Pro Ser Thr Gln Val Gly Phe Ile Asp
        275                 280                 285

Ala Ile Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
            325

<210> SEQ ID NO 34
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 34

Glu Glu Thr Arg Glu Leu Gln Ser Leu Ala Ala Ala Val Val Pro Ser
1               5                   10                  15

Ala Gln Thr Leu Lys Ile Thr Asp Phe Ser Leu Ser Asp Leu Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Arg Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
            85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
            165                 170                 175

Thr Thr Leu Lys Ile Ile Lys Gln Ala Ile Leu Ala Thr Asn Leu Ala
            180                 185                 190

Leu Tyr Ile Lys Arg Arg Gly Glu Phe Phe Glu Leu Ile Arg Lys Asn
```

```
            195                 200                 205
Gln Phe Asn Leu Glu Asp Pro His Gln Lys Glu Leu Phe Leu Ala Met
    210                 215                 220

Leu Met Thr Ala Cys Asp Leu Phe Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Pro Asp Leu Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 35
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 35

Glu Glu Thr Arg Glu Leu Arg Ser Leu Ala Ala Ala Val Val Pro Ser
1               5                   10                  15

Ala Gln Thr Leu Lys Ile Thr Asp Leu Ser Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys Arg
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
    210                 215                 220
```

-continued

```
Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
            260                 265                 270

Arg Glu Lys Lys Asn Lys Ile Pro Ser Met Gln Val Gly Phe Ile Asp
        275                 280                 285

Ala Thr Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
                325
```

<210> SEQ ID NO 36
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 36

```
atggaagaaa caagagagct acagtcgtta gcggctgctg tggtgccatc tgcccagacc    60
cttaaaatta ctgactttag cttcagtgac tttgagctgt ctgatctgga acagcactg   120
tgtacaattc ggatgtttac tgacctcaac cttgtgcaga acttccggat gaaacatgag   180
gttctttgca gatggatttt aagtgttaag aagaattatc ggaagaatgt tgcctatcat   240
aattggagac atgcctttaa tacagctcag tgcatgtttg ccgctctaaa agcaggcgaa   300
attcagaaca agctgactga cctggagata cttgcattgc tgattgctgc actaagccac   360
gatttggatc accgtggtgt gaataactct tacatacagc gaagtgaaca cccacttgcc   420
cagctttact gccattcaat catggaacac catcattttg accagtgcct gatgattctt   480
aatagtccag gcaatcagat tctcagtggc ctctccattg aagaatataa gacctcgttg   540
aaaataatca gcaagctat tttagctaca gacctagcac tgtacattaa gaggcgagga   600
gaattttttg aacttataag aaaaaatcaa ttcaatttgg aagatcctca tcaaaaggag   660
ttgttttttgg caatgctgat gacagcttgt gatctttctg caattacaaa accctggcca   720
attcaacaac ggatagcgga acttgtagca actgaatttt ttgatcaagg agacagagag   780
agagaagaac tcaacataga acccactgat ctaatgaaca gggagaagaa aaacaaaatc   840
ccaagtatgc aagttgggtt catagatgcc atctgcttgc aactgtatga ggccctgacc   900
cacgtgtcag aggactgttt ccctttgcta gatggctgca gaaagaacag gcaggaatgg   960
caggcccttg cagaacagca g                                              981
```

<210> SEQ ID NO 37
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 37

```
atggaaggaa caagagagct acagtcgtta gcggctgctg tggtgccatc tgcccagacc      60
cttaaaatta ctgactttag cttcagtgac tttgagctgt ctgatctgga acagcactg     120 tgtacaattc ggatgtttac tgacctcaac cttgtgcaga acttccggat gaaacatgag    180
gttctttgca gatggatttt aagtgttaag aagaattatc ggaagaatgt tgcctatcat    240
aattggagac atgcctttaa tacagctcag tgcatgtttg ccgctctaaa agcaggcaaa    300
attcagaaca agctgactga cctggagata cttgcattgc tgattgctgc actaagccac    360
gatttggatc accgtggtgt gaataactct tacatacagc gaagtgaaca tccacttgcc    420
cagctttact gccattctat catggaacac catcattttg accagtgcct gatgattctt    480
aatagtccag gcaatcagat tctcagtggc ctctccattg aagaatataa gaccacgttg    540
aaaataatca gcaagctat tttagcaaca gacctagcac tgtacattaa gaggcgagga    600
gaattttttg aacttataag aaaaaatcaa ttcaatttgg aagatcctca tcaaaaggag    660 ttgttttttgg caatgctgat gacagcttgt gatctttctg caattacaaa accctggcct    720
attcaacaac ggatagcgga acttgtagca actgaatttt ttgatcaagg agacagagag    780
agaaaagaac tcaacataga acccactgat ctaatgaaca gggagaagaa aaacaaaatc    840
ccaagtatgc aagttgggtt catagacgcc atctgcttgc aactgtatga ggccctgacc    900
cacgtgtcag aggacagttt ccctttgcta gatggctgca gaagaacag gcagaaatgg    960 caggcccttg cagaacagca g                                             981
```

<210> SEQ ID NO 38
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 38

```
atggaagaaa caagagagct acagtcgtta gcggctgctg tggtgccatc tgcccagacc      60
cttaaaatta ctgactttag cttcagtgac tttgagctgt ctgatctgga acagcactg     120 tgtacaattc ggatgtttac tgacctcaac cttgtgcaga gcttccggat gaaacatgag    180
gttctttgca gatggatttt aagtgttaag aagaattatc gggagaatgt tgcctatcat    240
aattggagac atgcctttaa tacagctcag tgcatgtttg ccgctctaaa agcaggcaaa    300
attcagaaca agctgactga cctggagata cttgcattgc tgattgctgc actaagccac    360
gatttggatc accgtggtgt gagtaactct tacatacagc gaagtgaaca tccacttgcc    420
cagctttact gccattcaat catggaacac catcattttg accagtgcct gatgattctt    480
aatagtccag gcaatcagat tctcagtggc ctctccattg aagaatataa gaccacgttg    540
aaaataatca gcaagctat tttagctaca gacctagcac tgtacattaa gaggcgagga    600
gaattttttg aacttataag aaaaaatcaa ttcaatttgg aagatcctca tcaaaaggag    660 ttgttttttgg caatgctgat gacagcttgt gttctttctg caattacaaa accctggcct    720
attcaacaac ggatagcgga acttgtagca actgaatttt ttgatcaagg agacagagag    780
agaaaagaac tcaacataga acccactgat ctaatgaaca gggagaagaa aaacaaaatc    840
ccaagtatgc aagttgggtt catagatgcc atctgcttgc aactgtatga ggccctgacc    900
cacgtgtcag aggactgttt ccctttgcta gatggctgca gaagaacag gcagaaatgg    960
```

```
caggcccttg cagaacagca g                                             981
```

<210> SEQ ID NO 39
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 39

```
atggaagaaa caagagagct acagtcgtta gcggctgctg tggtgccatc tgcccagacc    60
cttaaaatta ctgactttag cttcagtgac tttgagctgt ctgatctgga aacagcactg   120
tgtacaattc ggatgtttac tgacctcaac cttgtgcaga acttccggat gaaacatgag   180
gttctttgca gatggatttt aagtgttaag aagaattatc ggaagaatgt tgcctatcat   240
aattggagac atgcctttaa tacagctcag tgcatgtttg ccgctctaaa agcaggcaaa   300
attcagaaca agctgactga cctggagata cttgcattgc tgattgctgc actaagccac   360
gatttggatc accgtggtgt gaataactct tacatacagc gaagtgaaca tccacttgcc   420
cagccttact gccattcaat catggaacac catcattttg accagtgcct gatgattctt   480
aatagtccag gcaatcagat tctcagtggc ctctccattg aagaatataa gaccacgttg   540
aaaataatca gcaagctat tttagctaca gacctagcac tgtacattaa gaggcgagga   600
gaattttttg aacttataag aaaaaatcaa ttcaatttgg aagatcctca tcaaaaggag   660
ttgttgttgg caatgctgat gacagcttgt gatctttctg caattacaaa accctggcct   720
attcaacaac ggatagcgga actcgtagca actgaatttt ttgatcaagg agacagagag   780
agaaaagaac tcaacataga acccactgat ctaatgaaca gggagaagaa aaacaaaatc   840
ccaagtatgc aagttgggtt catagatgcc atctgcttgc aactgtatga ggccctgacc   900
cacgtgtcag aggactgttt ccctttgcta gatggctgca gaaagaacag gcagaaatgg   960
caggcccttg cagaacagca g                                             981
```

<210> SEQ ID NO 40
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 40

```
gaagaaacaa gagagctaca gtcgctagcg gctgctgtgg tgccatctgc ccagaccctt    60
aaaattactg actttagctt cagtgacttt gagctgtctg atctggaaac agcactgtgt   120
acaattcgga tgtttactga cctcaacctt gtgcagaact tccggatgaa acatgaggtt   180
ctttgcagat ggattttaag tgttaagaag aattatcgga agaatgttgc ctatcataat   240
tggagacatg cctttaatac agctcagtgc atgtttgccg ctctaaaagc aggcaaaatt   300
cagaacaagc tgactgacct ggagatactt gcattgctga ttgctgcact aagccacgat   360
ttggatcacc gtggtgtgaa taactcttac atacagcgaa gtgaacatcc acttgcccag   420
ctttactgcc attcaatcat ggaacaccat cattttgccc agtgcctgat gattcttaat   480
agtccaggca atcagattct cagtggcctc tccattgaag aatataagac cacgttgaaa   540
ataatcaagc aagctatttt agctacagac ctagcactgt acattaagag gcgaggagaa   600
```

```
ttttttgaac ttataagaaa aaatcaattc aatttggaag atcctcatca gaaggagttg    660
tttttggcaa tgctgatgac agcttgtaat ctttctgcaa ttacaaaacc ctggcctatt    720
caacaacgga tagcggaact tgtagcaact gaattttttg atcaaggaga cagagagaga    780
aaagaactca acatagaacc cactgatcta atgaacaggg agaagaaaaa caaaatccca    840
tgtatgcaag ttgggttcat agatgccatc tgcttgcaac tgtatgaggc cctgacccac    900
gtgtcagagg actgtttccc tttgctagat ggctgcagaa agaacaggca gaaatggcag    960
gcccttgcag aacagcag                                                  978
```

<210> SEQ ID NO 41
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 41

```
gaagaaacaa gagagctaca gtcgttagcg gctgctgtgg tgccatctgc ccagacccCtt    60 aaaattactg actttagctt cagtgacttt gagctgtctg atctggaaac agcactgtgt   120
acaattcgga tgtttactga cctcaacctt gtgcagaact tccggatgaa acatgaggtt   180
ctttgcagat ggattttaag tgttaagaag aattatcgga agaatgttgc ctatcataat   240
tggagacatg cctttaatac agctcagtgc atgtttgccg ctctaaaagc aggcaaaatt   300
cagaacaagc tgactgacct ggagatactt gcattgctga ttgctgcact aagccacgat   360
ttggatcacc gtggtgtgaa taactcttac atacagcgaa gtgaacatcc acttgcccag   420
cttgactgcc attcaatcat ggaacaccat cactttgacc agtgcctgat gattcttaat   480
agtccaggca atcagattct cagtggcctc tccattgaag aatataagac cacgttgaaa   540
ataatcaagc aagctatttt agctacagac ctagcactgt acattaagag gcgaggagaa   600
ttttttgaac atataagaaa aaatcaattc aatttggaag atcctcatca aaaggagttg   660
tttttggcaa tgctgatgac agcttgtgat ctttctgcaa ttacaaaacc ctggcctatt   720
caacaacgga tagcggaact tgtagcaact gaattttttg atcaaggaga cagagagaga   780
aaagaactca acatagaacc cactgatcta atgaacaggg agaagaaaaa caaaatccca   840
agtatgcaag ttgggttcat agatgccatc tgcttgcaac tgtatgaggc cctgacccac   900
gtgtcagagg actgtttccc tttgctagat ggctgcagaa agaacaggca gaaatggcag   960
gcccttgcag aacagcag                                                  978
```

<210> SEQ ID NO 42
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 42

```
gaagaaacaa gagagctaca gtcgttagcg gctgctgtgg tgccatctgc ccagacccCtt    60 aaaattactg actttagctt cagtgacttt gagctgtctg atctggaaac agcactgtgt   120
acaattcgga tgtttactga cctcaacctt gtgcagaact tccggatgga acatgaggtt   180
```

```
ctttgcagat ggattttaag tgttaagaag aattatcgga agcatgttgc ctatcataat      240
tggagacatg cctttaatac agctcagtgc atgtttgccg ctctaaaagc aggcaaaatt      300
cagaacaagc tgactgacct ggagatactt gcattgctga ttgctgcact aagccacgat      360
ttggatcacc gtggtgtgaa taactcttac atacagcgaa gtgaacatcc acttgcccag      420
ctttactgcc attcaatcat ggaacaccat cattttgacc agtgcctgat gattcttaat      480
agtccaggca atcagatact cagtggcctc tccattgaag aatataagac cacgttgaaa      540
ataatcaagc aagctatttt agcaacagac ctagcactgt acattaagag gcgaggagaa      600 tttttttgaac ttataagaaa aaatcaattc aatttggaag atcctcatca aaaggagttg     660
tttttggcaa tgctgatgac agcttgtgtt ctttctgcaa ttacaaaacc ctggcctatt      720
caacaacgga tagcggaact tgtagcaact gaatttttg atcaaggaga cagagagaga      780
aaagaactca acatagaacc cactgattta atgaacaggg agaagaaaaa caaaatccca     840
agtatgcaag ttgggttcat agatgccatc tgcttgcaac tgtatgaggc cctgacccac      900
gtgtcagagg actgtttccc tttgctagat ggctgcagaa agaacaggca gaaatggcag      960
gcccttgcag aacagcag                                                   978
```

<210> SEQ ID NO 43
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic Destabilizing Domain (DD)"

<400> SEQUENCE: 43

```
gaagaaacaa gagagctaca gtcgttagcg gctgctgtgg tgccatctgc ccagacccttt     60 aaaattactg actttagctt cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaagaag aattatcgga agatgttgc ctatcataat      240 tggagacatg cctttaatac agctcagtgc atgtttgccg ctctaaaagc aggcaaaatt      300
cagaacaagc tgactgacct ggagatactt gcattgctga ttgctgcact aagccacgat      360
ttggatcacc gtggtgtgaa taactcttac atacagcgaa gtgaacatcc acttgcccag      420
ctttactgcc attcaatcat ggaacaccat cattttgacc agtgcctgat gattcttaat      480
agtccaggca atcagattct cagtggcctc tccattgaag aatataagac cacgttgaaa      540
ataatcaagc aagctatttt agctacagac ctagcactgt acattaagag gcgaggagaa      600 tttttttgaac ttataagaaa aaatcaattc aatttggaag atcctcatca aaaggagttg     660
tttttggcaa tgctgatgac agcttgtggt ctttctgcaa ttacaaaacc ctggcctatt      720
caacaacgga tagcggaact tgtagcaact gaatttttg atcaaggaga cagagagaga      780
aaagaactca acatagaacc cactgatcta atgaacaggg agaagaaaaa caaaatccca     840
agtatgcaag ttgggttcat agatgccatc tgcttgcaac tgtatgaggc cctgacccac      900
gtgtcagagg actgtttccc tttgctagat ggctgcagaa agaacaggca gaaatggcag      960
gcccttgcag aacagcag                                                   978
```

<210> SEQ ID NO 44
<211> LENGTH: 978
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic Destabilizing Domain (DD)"

<400> SEQUENCE: 44
gaagaaacaa gagagctaca gtcgttagcg gctgctgtgg tgccatctgc ccagacccct      60
aaaattactg actttagcct cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaaggag aattatcgga agaatgttgc ctatcataat     240
tggagacatg cctttaatac agctcagtgc atgtttgccg ctctaaaagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ctttactgcc attcaatcat ggaacaccat cattttgacc agtgcctgat gattcttaat     480
agtccaggca atcagattct cagtggcctc tccattgaag aatataagac cacgttgaaa     540
ataatcaagc aagctatttt agctacaaac ctagcactgt acattaagag gcgaggagaa     600
ttttttgaac ttataagaaa aaatcaattc aatttggaag atcctcatca aaaggagttg     660
tttttggcaa tgctgatgac agcttgtgat ctttctgcaa ttacaaaacc ctggcctatt     720
caacaacgga tagcggaact tgtagcaact gaattttttg atcaaggaga cagagagaga     780
aaagaattca acatagaacc cacagatcta atgaacaggg agaagaaaaa caaaatccca     840
agtatgcaag ttgggttcat agatgccatc tgcttgcaac tgtatgaggc cctgaccccac    900 gtgtcagagg actgtttccc tttgctagat ggctgcagaa agaacaggca gaaatggcag     960
gcccttgcag aacagcag                                                   978

<210> SEQ ID NO 45
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 45
gacgaaacaa gagagctaca gtcgttagcg gctgctgtgg tgccatctgc ccagacccct      60
agaattactg actttagctt cagtgactct gagctgtctg atctggaaac agcactgtgt     120
acaattcgga tgtttactga cctcaacctt gtgcagaact tccggatgaa acatgaggtt     180
ctttgcagat ggattttaag tgttaagaag aattatcgga agaatgttgc ctatcataat     240
tggagacatg cctttaatac agctcagtgc atgtttgccg ctctaagagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ctttaccgcc attcaatcat ggaacaccat cattttgacc agtgcctgat gattcttaat     480
agtcccggca atcagattct cagtggcctc tccattgaag aatataagac cacgctgaaa     540
ataatcaagc aagctatttt agctacagac ctagcactgt acattaagag gcgaggagaa     600
ttttttgaac ttataagaaa aagtcaattc aatttggaag atcctcatca aaaggagttg     660
tttttggcaa tgctgatgac agcttgtgat ctttctgcaa ttacaaaacc ctggcctatt     720
caacaacgga tagcggaact tgtagcaact gaattttttg atcaagggga cagagagaga     780
```

| | |
|---|---|
| aaagagctca acacagaacc cactgatcta atgaacaggg agaagaaaaa caaaatccca | 840 |
| agtgcgcaag ttgggttcat agatgccatc tgcttgcaac tgtatgaggc cctgacccac | 900 |
| gtgtcagagg actgtttccc tttgctagat ggctgcagaa agaacaggca gaaatggcag | 960 |
| gcccttgcag aacagcag | 978 |

<210> SEQ ID NO 46
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 46

| | |
|---|---|
| gaagaaacaa gagagctaca gtcgttagcg gctgctgtgg tgccatctgc ccagacccctt | 60 |
| aaaattactg actttagctt cagtgacttt gagctgtctg atctggaaac agcactgtgt | 120 |
| acaattcgga tgtttactga cctcaacctt gtgcagaact tccggatgaa acatgaggtt | 180 |
| ctttgcagat ggattttaag tgttaagaag aattatcgga agcatgttgc ctatcataat | 240 |
| tggagacatg cctttaatac agctcagtgc atgtttgccg ctctaaaagc aggcaaaatt | 300 |
| cagaacaagc tgactgacct ggagatactt gcattgctga ttgctgcact aagccacgat | 360 |
| ttggatcacc gtggtgtgaa taactcttac atacagcgaa gtgaacatcc acttgcccag | 420 |
| cttaactgcc attcaatcat ggaacaccat cattttgacc agtgcctgat gattcttaat | 480 |
| agtccaggca atcagattct cagtggcctc tccattgaag aatataagac cacgttgaaa | 540 |
| ataatcaagc aagctatttt agctacagac ctagcactgt acattaagag gcgaggagaa | 600 |
| ttttttgaac tttataagaaa aaatcaattc aatttggaag atcctcatca aaaggagttg | 660 |
| tttttggcaa tgctgatgac atcttgtgat cttttctgcaa ttacaaaacc ctggcctatt | 720 |
| caacaacgga tagcggaact tgtagcaact gaatttttttg atcaaggaga cagagagaga | 780 |
| aaagaactca acatagaacc cactgatcta atgaacaggg agaagaaaaa caaaatccca | 840 |
| agtatgcaag ttgggttcat agatgccatc tgcttgcaac tgtatgaggc cctgacccac | 900 |
| gtgtcagagg actgtttccc tttgctagat ggctgcagaa agaacaggca gaaatggcag | 960 |
| gcccttgcag aacagcag | 978 |

<210> SEQ ID NO 47
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 47

| | |
|---|---|
| gaagaaacaa gagagctaca gtcgctagcg gctgctgtgg tgccatctgc ccagaccctt | 60 |
| aaaattactg actttagctt cagtgacttt gagctgtctg atctggaaac agcactgtgt | 120 |
| acaattcgga tgtttactga cctcaacctt gtgcagaact tccggatgaa acatgaggtt | 180 |
| ctttgcagat ggattttaag tgttaagaag aattatcgga agaatgttgc ctatcataat | 240 |
| tggagacatg cctttaatac agctcagtgc atgtttgccg ctctaaaagc aggcaaaatt | 300 |
| cagagcaagc tgactgacct ggagatactt gcattgctga ttgctgcact aagccacgat | 360 |
| ttggatcacc gtggtgtgaa taactcttac atacagcgaa gtgaacatcc acttgcccag | 420 |

```
ctttactgcc attcaatcat ggaacaccat cattttgccc agtgcctgat gattcttaat    480
agtccaggca atcagattct cagtggcctc tccattgaag aatataagac cacgttgaaa    540
ataatcaagc aagctatttt agctacagac ctagcactgt acattaagag gcgaggagaa    600 tttttgaac ttataagaaa aaatcaattc aatttggaag atcctcatca gaaggagttg     660
tttttggcaa tgctgatgac agcttgtaat ctttctgcaa ttacaaaacc ctggcctatt    720
caacaacgga tagcggaact tgtagcaact gaatttttg atcaaggaga cagagagaga    780
aaagaactca acatagaacc cactgatcta atgaacaggg agaagaaaaa caaaatccca    840
tgtatgcaag ttgggttcat agatgccatc tgcttgcaac tgtatgaggc cctgacccac    900
gtgtcagagg actgtttccc tttgctagat ggctgcagaa agaacaggca gaaatggcag    960
gcccttgcag aacagcag                                                  978
```

<210> SEQ ID NO 48
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 48

```
gaagaaacaa gagagctaca gtcgttagcg gctgctgtgg tgccatctgc ccagaccctt    60
aaaattactg actttagctt cagtgacttt gagctgtctg atctggaaac agcactgtgt    120
acaattcgga tgtttactga cctcaacctt gtgcagaact tccggatgaa acatgaggtt    180
ctttgcagat gggttttaag tgttaagaag aattatcgga agaatgttgc ctatcacaat    240
tggagacatg cctttaatac agctcagtgc atgtttgccg ctctaaaagc aggcaaaatt    300
cagaataagc tgactgacct ggagatactt gcattgctga ttgctgcact aagccacgat    360
ttggatcacc gtggtgtgaa taactcttac atacagcgaa gtgaacatcc acttgcccag    420
ctttactgcc attcaatcat ggaacaccat cattttgacc agtgcctgat gattcttaat    480
agtccaggca atcagattct cagtggcctc tccattgaag aatataaggc cacgttgaaa    540
ataatcaagc aagctatttt agctacagac ctagcactgt acattaagag gcgaggagaa    600 tttttgaac ttataagaaa aaatcaactc aattcggaag atcctcatca aaaggagttg     660
tttttggcaa tgctgatgac agcttgtgat ctttctgcaa ttacaaaacc ctggcctatt    720
caacaacgga tagcggaact tgtagcaact gaatttttg atcaaggaga cagagagaga    780
aaagaactta acatagaacc cactgatcca atgaacaggg agaagaaaaa caaaatccca    840
agtatgcaag ttgggttcat agatgccatc tgcttgcaac tgtatgaggc cctgacccac    900
gtgtcagagg actgtttccc tttgctagat ggctgcagaa agaacaggca gaaatggcag    960
gcccttgcag aacagcag                                                  978
```

<210> SEQ ID NO 49
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 49

```
gaagaaacaa gagagctaca gtcgttagcg gctgctgtgg tgccatctgc ccagacccett      60 aaaattactg actttggctt cagtgacttt gagctgtctg atctggaaac agcactgtgt      120
acaattcgga tgtttactga cctcaacctt gcgcagagct tccggatgga acatgaggtt      180
ctttgcagat ggattttaag tgttaagaag aattatcgga agaatgttgc ctatcataat      240
tggagacatg cctttaatac agctcagtgc atgtttgccg ctctaaaagc aggcaaaatt      300
cagaacaagc tgactgacct ggagatactt gcattgctga ttgctgcact aagccacgat      360
ttggatcacc gtggtgtgaa taacccttac atacagcgaa gtgaacatcc acttgcccag      420
ctttactgcc attcaatcat ggaacaccat cattttgacc agtgcctgat gattcttaat      480
agtccaggca atcagattct cagtggcctc tccattgaag aatataagac cacgttgaaa      540
ataatcaagc aagctatttt agctacagac ctagcactgt acattaagag gcgaggagaa      600
ttttttgaac ttataagaaa aaatcaattc aatttggaag atcctcatca aaaggagttg      660
tttttggcaa tgctgatgac agcttgtgat ctttctgcaa ttacaaaacc ctggcctatt      720
caacaacgga tagcggaact tgtagcaact gaattttttg atcaaggaga cagagagaga      780
aaagaactca acatagaacc cactgatcta atgaacaggg agaagaaaaa caaaatccca      840
agtatgcaag ttgggttcat agatgccatc tgcttgcaac tgtatgaggc cctgacccac      900
gtgtcagagg actgttcccc tttgctagat ggctgcagaa agaacaggca gaaatggcag      960
gcccttgcag aacagcag                                                   978

<210> SEQ ID NO 50
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 50
gaagaaacaa gagagctaca gtcgttagcg gctgctgtgg tgccatccgc ccagacccett      60 aaaattactg actttagctt cagtgacttt gagctgtctg atctggaaac agcactgtgt      120
acaattcgga tgtttactga cctcaacctt gtgcagaact tccggatgaa acatgaggtt      180
ctttgcagat ggattttaag tgttaagaag aattatcgga agaatgttgc ctatcataat      240
tggagacatg cctttaatac agctcagtgc atgtttgccg ctctaaaagc aggcaaaatt      300
cagaacaagc tgactgacct ggagatactt gcattgctgg ttgctgcact aagccacgat      360
ttggaccacc gtggtgtgaa taactcttac atacagcgaa gtgaacatcc acttgcccag      420
ctttactgcc attcaatcat ggaacaccat cattttgacc agtgcctgat gattcttaat      480
agtccaggca atcaaattct cagtggcctc tccattgaag aatataagac cacgttgaaa      540
ataatcaagc aggctatttt agctacagac ctagcactgt acattaagag gcgaggagaa      600
ttttttgaac ttataagaaa aaatcaattc aatttggaag atcctcatca aaaggagttg      660
tttttggcaa tgctgatgac agcttgtgat ctttctgcaa ttacaaaacc ctggcctatt      720
caacaacgga tagcggaact tgtagcaact gaattttttg atcaaggaga cagagagaga      780
aaagaactca acatagaacc cactgatcta atgaacaggg agaagaaaaa caaaatccca      840
agtacgcaag ttgggttcat agatgccatc tgcttgcaac tgtatgaggc cctgacccac      900
gtgtcagagg actgtttccc tttgctagat ggctgcagaa agaacaggca gaaatggcag      960
gcccttgcag aacagcag                                                   978
```

<210> SEQ ID NO 51
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 51

| | | | | | |
|---|---|---|---|---|---|
| gaagaaacaa | gagagctaca | gtcgttagcg | gctgctgtgg | tgccatctgc | ccagacccctt | 60 |
| aaaattactg | actttagcct | cagtgacctt | gagctgtctg | atctggaaac | agcactgtgt | 120 |
| acaattcgga | tgtttactga | cctcaacctt | gtgcagaact | tccggatgaa | acatgaggtt | 180 |
| ctttgcagat | ggattttaag | tgttaagaag | aattatcgga | agaatgttgc | ctatcataat | 240 |
| tggagacatg | cctttaatac | agctcagtgc | atgtttgccg | ctctaaaagc | aggcaaaatt | 300 |
| cagaacaagc | tgactgacct | ggagatactt | gcattgctga | ttgctgcact | aagccacgat | 360 |
| ttggatcacc | gtggtgtgaa | taactcttac | atacagcgaa | gtgaacatcc | acttgcccag | 420 |
| ctttactgcc | attcaatcat | ggaacaccat | cattttgacc | agtgcctgat | gattcttaat | 480 |
| agtccaggca | atcagattct | cagtggcctc | tccattgaag | aatataagac | cacgttgaaa | 540 |
| ataatcaagc | aagctatttt | agctacaaac | ctagcactgt | acattaagag | gcgaggagaa | 600 |
| tttttgaac | ttataagaaa | aaatcaattc | aatttggaag | atcctcatca | aaaggagttg | 660 |
| tttttggcaa | tgctgatgac | agcttgtgat | cttttttgcaa | ttacaaaacc | ctggcctatt | 720 |
| caacaacgga | tagcggaact | tgtagcaact | gaatttttg | atcaaggaga | cagagagaga | 780 |
| aaagaactca | acatagaacc | ccctgattta | atgaacaggg | agaagaaaaa | caaaattcca | 840 |
| agtatgcaag | ttgggttcat | agatgccatc | tgcttgcaac | tgtatgaggc | cctgacccac | 900 |
| gtgtcagagg | actgtttccc | tttgctagat | ggctgcagaa | agaacaggca | gaaatggcag | 960 |
| gcccttgcag | agcagcag | | | | | 978 |

<210> SEQ ID NO 52
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 52

| | | | | | |
|---|---|---|---|---|---|
| gaagaaacaa | gagagctacg | gtcgttagcg | gctgctgtgg | tgccatctgc | ccagacccctt | 60 |
| aaaattactg | accttagctt | cagtgacttt | gagctgtctg | atctggaaac | agcactgtgt | 120 |
| acaattcgga | tgtttactga | cctcaacctt | gtgcagaact | tccggatgaa | acatgaggtt | 180 |
| ctttgcagat | ggattttaag | tgttaagaag | aattatcgga | agaatgttgc | ctatcataat | 240 |
| tggagacatg | cctttaatac | agctcagtgc | atgtttgccg | ctctaaaagc | aggcaaaatt | 300 |
| cagaacaagc | tgactgacct | ggagatactt | gcattgctga | ttgctgcact | aagccacgat | 360 |
| ttggatcacc | gtggtgtgaa | taactcttac | atacagcgaa | gtgaacatcc | acttgcccag | 420 |
| ctttactgcc | gttcaatcat | ggaacaccat | cattttgacc | agtgcctgat | gattcttaat | 480 |
| agtccaggca | atcagattct | cagtggcctc | tccattgaag | aatataagac | cacgttgaaa | 540 |
| ataatcaagc | aagctatttt | agctacagac | ctagcactgt | acattaagag | gcgaggagaa | 600 |

```
tttttttgaac ttataagaaa aaatcaattc aatttggaag atcctcatca aaaggagttg   660
tttttggcaa tgctgatgac agcttgtgat ctttctgcaa ttacaaaacc ctggcctatt   720
caacaacgga tagcggaact tgtagcaact gaattttttg atcaaggaga cagagagaga   780
aaagaactca acatagaacc cactgattta atgaacaggg agaagaaaaa caaaatccca   840
agtatgcaag ttgggttcat agatgccacc tgcttgcaac tgtatgaggc cctgacccac   900
gtgtcagagg actgtttccc tttgctagat ggctgcagaa agaacaggca gaaatggcag   960
gcccttgcag aacagcag                                                 978

<210> SEQ ID NO 53
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 53
```

Glu Glu Thr Arg Glu Leu Gln Ser Leu Ala Ala Ala Val Val Pro Ser
1               5                   10                  15

Ala Gln Thr Leu Lys Ile Thr Asp Phe Ser Leu Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
        50                  55                  60

Ile Leu Ser Val Lys Glu Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
        130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asn Leu Ala
                180                 185                 190

Leu Tyr Ile Lys Arg Arg Gly Glu Phe Phe Glu Leu Ile Arg Lys Asn
            195                 200                 205

Gln Phe Asn Leu Glu Asp Pro His Gln Lys Glu Leu Phe Leu Ala Met
        210                 215                 220

Leu Met Thr Ala Cys Asn Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Phe Asn Ile Glu Pro Thr Asp Leu Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
            290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 54
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 54
gaagaaacaa gagagctaca gtcgttagcg gctgctgtgg tgccatctgc ccagacccctt    60 aaaattactg actttagcct cagtgacttt gagctgtctg atctggaaac agcactgtgt   120
acaattcgga tgtttactga cctcaacctt gtgcagaact tccggatgaa acatgaggtt   180
ctttgcagat ggattttaag tgttaaggag aattatcgga agaatgttgc ctatcataat   240
tggagacatg cctttaatac agctcagtgc atgtttgccg ctctaaaagc aggcaaaatt   300
cagaacaagc tgactgacct ggagatactt gcattgctga ttgctgcact aagccacgat   360
ttggatcacc gtggtgtgaa taactcttac atacagcgaa gtgaacatcc acttgcccag   420
ctttactgcc attcaatcat ggaacaccat cattttgacc agtgcctgat gattcttaat   480
agtccaggca atcagattct cagtggcctc tccattgaag aatataagac cacgttgaaa   540
ataatcaagc aagctatttt agctacaaac ctagcactgt acattaagag gcgaggagaa   600
ttttttgaac ttataagaaa aaatcaattc aatttggaag atcctcatca aaaggagttg   660
ttttttgcaa tgctgatgac agcttgtaat ctttctgcaa ttacaaaacc ctggcctatt   720
caacaacgga tagcggaact tgtagcaact gaattttttg atcaaggaga cagagagaga   780
aaagaattta acatagaacc cacagatcta atgaacaggg agaagaaaaa caaaatccca   840
agtatgcaag ttgggttcat agatgccatc tgcttgcaac tgtatgaggc cctgacccac   900
gtgtcagagg actgtttccc tttgctagat ggctgcagaa agaacaggca gaaatggcag   960
gcccttgcag aacagcag                                                  978

<210> SEQ ID NO 55
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 55

Glu Glu Thr Arg Glu Leu Gln Ser Leu Ala Ala Val Val Pro Ser
1               5                   10                  15

Ala Gln Thr Leu Lys Ile Thr Asp Phe Ser Leu Ser Asp Phe Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Arg Met Lys His Glu Val Leu Cys Arg Trp
    50                  55                  60

Ile Leu Ser Val Lys Glu Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
        130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asn Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
210                 215                 220

Leu Met Thr Ala Cys Gly Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Lys Glu Phe Asn Ile Glu Pro Thr Asp Leu Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
290                 295                 300

Cys Phe Pro Leu Leu Asp Gly Cys Arg Lys Asn Arg Gln Lys Trp Gln
305                 310                 315                 320

Ala Leu Ala Glu Gln Gln
            325

<210> SEQ ID NO 56
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 56
gaagaaacaa gagagctaca gtcgttagcg gctgctgtgg tgccatctgc ccagaccctt      60
aaaattactg actttagcct cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaaggag aattatcgga agaatgttgc ctatcataat     240
tggagacatg cctttaatac agctcagtgc atgtttgccg ctctaaaagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ctttactgcc attcaatcat ggaacaccat cattttgacc agtgcctgat gattcttaat     480

```
agtccaggca atcagattct cagtggcctc tccattgaag aatataagac cacgttgaaa    540
ataatcaagc aagctatttt agctacaaac ctagcactgt acattaagag gcgaggagaa    600 tttttttgaac ttataagaaa aaatcaattc aatttggaag atcctcatca aaaggagttg   660
tttttggcaa tgctgatgac agcttgtggt ctttctgcaa ttacaaaacc ctggcctatt    720
caacaacgga tagcggaact tgtagcaact gaatttttg atcaaggaga cagagagaga    780
aaagaattta acatagaacc cacagatcta atgaacaggg agaagaaaaa caaaatccca   840
agtatgcaag ttgggttcat agatgccatc tgcttgcaac tgtatgaggc cctgacccac    900
gtgtcagagg actgttccc tttgctagat ggctgcagaa agaacaggca gaaatggcag     960
gcccttgcag aacagcag                                                  978
```

```
<210> SEQ ID NO 57
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 57

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Glu
225                 230                 235                 240

Phe Tyr Pro Tyr Asp Val Pro Asp Tyr Ala Glu Glu Thr Arg Glu Leu
                245                 250                 255
```

| | | | | | | | | | | | | |
|---|---|---|---|---|---|---|---|---|---|---|---|---|
|Gln|Ser|Leu|Ala|Ala|Val|Val|Pro|Ser|Ala|Gln|Thr|Leu|Lys|Ile|
| | | |260| | |265| | | |270| | |

Thr Asp Phe Ser Leu Ser Asp Phe Glu Leu Ser Asp Leu Glu Thr Ala
            275                 280                 285

Leu Cys Thr Ile Arg Met Phe Thr Asp Leu Asn Leu Val Gln Asn Phe
290                 295                 300

Arg Met Lys His Glu Val Leu Cys Arg Trp Ile Leu Ser Val Lys Glu
305                 310                 315                 320

Asn Tyr Arg Lys Asn Val Ala Tyr His Asn Trp Arg His Ala Phe Asn
            325                 330                 335

Thr Ala Gln Cys Met Phe Ala Ala Leu Lys Ala Gly Lys Ile Gln Asn
            340                 345                 350

Lys Leu Thr Asp Leu Glu Ile Leu Ala Leu Leu Ile Ala Ala Leu Ser
            355                 360                 365

His Asp Leu Asp His Arg Gly Val Asn Asn Ser Tyr Ile Gln Arg Ser
            370                 375                 380

Glu His Pro Leu Ala Gln Leu Tyr Cys His Ser Ile Met Glu His His
385                 390                 395                 400

His Phe Asp Gln Cys Leu Met Ile Leu Asn Ser Pro Gly Asn Gln Ile
            405                 410                 415

Leu Ser Gly Leu Ser Ile Glu Glu Tyr Lys Thr Thr Leu Lys Ile Ile
            420                 425                 430

Lys Gln Ala Ile Leu Ala Thr Asn Leu Ala Leu Tyr Ile Lys Arg Arg
            435                 440                 445

Gly Glu Phe Phe Glu Leu Ile Arg Lys Asn Gln Phe Asn Leu Glu Asp
450                 455                 460

Pro His Gln Lys Glu Leu Phe Leu Ala Met Leu Met Thr Ala Cys Asp
465                 470                 475                 480

Leu Ser Ala Ile Thr Lys Pro Trp Pro Ile Gln Gln Arg Ile Ala Glu
            485                 490                 495

Leu Val Ala Thr Glu Phe Phe Asp Gln Gly Asp Arg Glu Arg Lys Glu
            500                 505                 510

Phe Asn Ile Glu Pro Thr Asp Leu Met Asn Arg Glu Lys Lys Asn Lys
            515                 520                 525

Ile Pro Ser Met Gln Val Gly Phe Ile Asp Ala Ile Cys Leu Gln Leu
530                 535                 540

Tyr Glu Ala Leu Thr His Val Ser Glu Asp Cys Phe Pro Leu Leu Asp
545                 550                 555                 560

Gly Cys Arg Lys Asn Arg Gln Lys Trp Gln Ala Leu Ala Glu Gln Gln
            565                 570                 575

<210> SEQ ID NO 58
<211> LENGTH: 1731
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic Destabilizing Domain (DD)"

<400> SEQUENCE: 58
atggtgagca agggcgccga gctgttcacc ggcatcgtgc ccatcctgat cgagctgaat    60
ggcgatgtga atggccacaa gttcagcgtg agcggcgagg gcgagggcga tgccacctac   120
ggcaagctga ccctgaagtt catctgcacc accggcaagc tgcctgtgcc ctggcccacc   180
ctggtgacca ccctgagcta cggcgtgcag tgcttctcac gctaccccga tcacatgaag   240

```
cagcacgact tcttcaagag cgccatgcct gagggctaca tccaggagcg caccatcttc      300
ttcgaggatg acggcaacta caagtcgcgc gccgaggtga agttcgaggg cgataccctg      360
gtgaatcgca tcgagctgac cggcaccgat ttcaaggagg atggcaacat cctgggcaat      420
aagatggagt acaactacaa cgcccacaat gtgtacatca tgaccgacaa ggccaagaat      480
ggcatcaagg tgaacttcaa gatccgccac aacatcgagg atggcagcgt gcagctggcc      540
gaccactacc agcagaatac ccccatcggc gatggccctg tgctgctgcc cgataaccac      600
tacctgtcca cccagagcgc cctgtccaag accccaacg agaagcgcga tcacatgatc      660
tacttcggct tcgtgaccgc cgccgccatc acccacggca tggatgagct gtacaaggaa      720
ttctatccgt acgacgtacc agactacgca gaagaaacaa gagagctaca gtcgttagcg      780
gctgctgtgg tgccatctgc ccagacccct aaaattactg actttagcct cagtgacttt      840
gagctgtctg atctggaaac agcactgtgt acaattcgga tgtttactga cctcaacctt      900
gtgcagaact tccggatgaa acatgaggtt ctttgcagat ggattttaag tgttaaggag      960
aattatcgga agaatgttgc ctatcataat tggagacatg cctttaatac agctcagtgc     1020
atgtttgccg ctctaaaagc aggcaaaatt cagaacaagc tgactgacct ggagatactt     1080
gcattgctga ttgctgcact aagccacgat ttggatcacc gtggtgtgaa taactcttac     1140
atacagcgaa gtgaacatcc acttgcccag ctttactgcc attcaatcat ggaacaccat     1200
cattttgacc agtgcctgat gattcttaat agtccaggca atcagattct cagtggcctc     1260
tccattgaag aatataagac cacgttgaaa ataatcaagc aagctatttt agctacaaac     1320
ctagcactgt acattaagag gcgaggagaa tttttttgaac ttataagaaa aaatcaattc     1380
aatttggaag atcctcatca aaaggagttg ttttttggcaa tgctgatgac agcttgtgat     1440
ctttctgcaa ttacaaaacc ctggcctatt caacaacgga tagcggaact tgtagcaact     1500 gaatttttg atcaaggaga cagagagaga aaagaattca acatagaacc cacagatcta     1560
atgaacaggg agaagaaaaa caaaatccca agtatgcaag ttgggttcat agatgccatc     1620
tgcttgcaac tgtatgaggc cctgacccac gtgtcagagg actgttttccc tttgctagat     1680 ggctgcagaa agaacaggca gaaatggcag gcccttgcag aacagcagtg a              1731
```

<210> SEQ ID NO 59
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 59

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
```

```
                    85                  90                  95
Arg Thr Ile Phe Phe Glu Asp Asp Gly Asn Tyr Lys Ser Arg Ala Glu
                100                 105                 110

Val Lys Phe Glu Gly Asp Thr Leu Val Asn Arg Ile Glu Leu Thr Gly
                115                 120                 125

Thr Asp Phe Lys Glu Asp Gly Asn Ile Leu Gly Asn Lys Met Glu Tyr
            130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Ile Tyr Phe Gly Phe
        210                 215                 220

Val Thr Ala Ala Ala Ile Thr His Gly Met Asp Glu Leu Tyr Lys Glu
225                 230                 235                 240

Phe Glu Glu Thr Arg Glu Leu Gln Ser Leu Ala Ala Val Val Pro
                245                 250                 255

Ser Ala Gln Thr Leu Lys Ile Thr Asp Phe Ser Leu Ser Asp Phe Glu
            260                 265                 270

Leu Ser Asp Leu Glu Thr Ala Leu Cys Thr Ile Arg Met Phe Thr Asp
        275                 280                 285

Leu Asn Leu Val Gln Asn Phe Arg Met Lys His Glu Val Leu Cys Arg
    290                 295                 300

Trp Ile Leu Ser Val Lys Glu Asn Tyr Arg Lys Asn Val Ala Tyr His
305                 310                 315                 320

Asn Trp Arg His Ala Phe Asn Thr Ala Gln Cys Met Phe Ala Ala Leu
                325                 330                 335

Lys Ala Gly Lys Ile Gln Asn Lys Leu Thr Asp Leu Glu Ile Leu Ala
            340                 345                 350

Leu Leu Ile Ala Ala Leu Ser His Asp Leu Asp His Arg Gly Val Asn
        355                 360                 365

Asn Ser Tyr Ile Gln Arg Ser Glu His Pro Leu Ala Gln Leu Tyr Cys
    370                 375                 380

His Ser Ile Met Glu His His His Phe Asp Gln Cys Leu Met Ile Leu
385                 390                 395                 400

Asn Ser Pro Gly Asn Gln Ile Leu Ser Gly Leu Ser Ile Glu Glu Tyr
                405                 410                 415

Lys Thr Thr Leu Lys Ile Ile Lys Gln Ala Ile Leu Ala Thr Asn Leu
            420                 425                 430

Ala Leu Tyr Ile Lys Arg Arg Gly Glu Phe Phe Glu Leu Ile Arg Lys
        435                 440                 445

Asn Gln Phe Asn Leu Glu Asp Pro His Gln Lys Glu Leu Phe Leu Ala
    450                 455                 460

Met Leu Met Thr Ala Cys Asp Leu Ser Ala Ile Thr Lys Pro Trp Pro
465                 470                 475                 480

Ile Gln Gln Arg Ile Ala Glu Leu Val Ala Thr Glu Phe Phe Asp Gln
                485                 490                 495

Gly Asp Arg Glu Arg Lys Glu Phe Asn Ile Glu Pro Thr Asp Leu Met
            500                 505                 510
```

```
Asn Arg Glu Lys Lys Asn Lys Ile Pro Ser Met Gln Val Gly Phe Ile
        515                 520                 525

Asp Ala Ile Cys Leu Gln Leu Tyr Glu Ala Leu Thr His Val Ser Glu
        530                 535                 540

Asp Cys Phe Pro Leu Leu Asp Gly Cys Arg Lys Asn Arg Gln Lys Trp
545                 550                 555                 560

Gln Ala Leu Ala Glu Gln Gln Tyr Pro Tyr Asp Val Pro Asp Tyr Ala
                565                 570                 575

<210> SEQ ID NO 60
<211> LENGTH: 1731
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 60
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
ctggtgacca ccctgagcta cggcgtgcag tgcttctcac gctacccccga tcacatgaag     240 cagcacgact tcttcaagag cgccatgcct gagggctaca tccaggagcg caccatcttc     300
ttcgaggatg acggcaacta caagtcgcgc gccgaggtga agttcgaggg cgatacccctg     360 gtgaatcgca tcgagctgac cggcaccgat ttcaaggagg atggcaacat cctgggcaat     420
aagatggagt acaactacaa cgcccacaat gtgtacatca tgaccgacaa ggccaagaat     480
ggcatcaagg tgaacttcaa gatccgccac aacatcgagg atggcagcgt gcagctggcc     540
gaccactacc agcagaatac ccccatcggc gatggccctg tgctgctgcc cgataaccac     600
tacctgtcca cccagagcgc cctgtccaag acccccaacg agaagcgcga tcacatgatc     660
tacttcggct tcgtgaccgc cgccgccatc acccacggca tggatgagct gtacaaggaa     720
ttcgaagaaa caagagagct acagtcgtta gcggctgctg tggtgccatc tgcccagacc     780
cttaaaatta ctgactttag cctcagtgac tttgagctgt ctgatctgga acagcactg     840 tgtacaattc ggatgtttac tgacctcaac cttgtgcaga acttccggat gaaacatgag     900
gttctttgca gatggatttt aagtgttaag gagaattatc ggaagaatgt tgcctatcat     960
aattggagac atgcctttaa tacagctcag tgcatgtttg ccgctctaaa agcaggcaaa    1020
attcagaaca agctgactga cctggagata cttgcattgc tgattgctgc actaagccac    1080
gatttggatc accgtggtgt gaataactct tacatacagc gaagtgaaca tccacttgcc    1140
cagctttact gccattcaat catggaacac atcatttttg accagtgcct gatgattctt    1200
aatagtccag gcaatcagat tctcagtggc ctctccattg aagaatataa gaccacgttg    1260
aaaataatca agcaagctat tttagctaca aacctagcac tgtacattaa gaggcgagga    1320
gaattttttg aacttataag aaaaaatcaa ttcaatttgg aagatcctca tcaaaaggag    1380 ttgttttttgg caatgctgat gacagcttgt gatcttttctg caattacaaa accctggcct    1440
attcaacaac ggatagcgga acttgtagca actgaatttt ttgatcaagg agacagagag    1500
agaaaagaat tcaacataga acccacagat ctaatgaaca gggagaagaa aaacaaaatc    1560
ccaagtatgc aagttgggtt catagatgcc atctgcttgc aactgtatga ggccctgacc    1620
```

```
cacgtgtcag aggactgttt cccttttgcta gatggctgca gaaagaacag gcagaaatgg    1680
caggcccttg cagaacagca gtatccgtac gacgtaccag actacgcatg a              1731
```

<210> SEQ ID NO 61
<211> LENGTH: 2502
<212> TYPE: DNA
<213> ORGANISM: Homo sapiens

<400> SEQUENCE: 61

```
atgttgccct ttggagacaa acaagagaa atggtcaatg catggtttgc tgagagagtt      60
cacaccatcc ctgtgtgcaa ggaaggtatc agaggccaca ccgaatcttg ctcttgtccc    120
ttgcagcaga gtcctcgtgc agataacagt gcccctggaa caccaaccag gaaaatctct    180
gcctctgaat tgaccggcc tcttagaccc attgttgtca aggattctga gggaactgtg     240
agcttcctct ctgactcaga aaagaaggaa cagatgcctc taaccccctcc aaggtttgat   300 catgatgaag ggaccagtg ctcaagactc ttggaattag tgaaggatat ttctagtcat     360
ttggatgtca cagccttatg tcacaaaatt ttcttgcata ccatggact gatatctgct     420 gaccgctatt ccctgttcct tgtctgtgaa gacagctcca atgacaagtt tcttatcagc    480
cgcctctttg atgttgctga aggttcaaca ctggaagaag tttcaaataa ctgtatccgc    540
ttagaatgga acaaaggcat tgtgggacat gtggcagcgc ttggtgagcc cttgaacatc    600
aaagatgcat atgaggatcc tcggttcaat gcagaagttg accaaattac aggctacaag    660
acacaaagca ttctttgtat gccaattaag aatcataggg aagaggttgt tggtgtagcc    720
caggccatca caagaaatc aggaaacggt gggacatttt ctgaaaaaga tgaaaaggac    780
tttgctgctt atttggcatt ttgtggtatt gttcttcata atgctcagct ctatgagact    840
tcactgctgg agaacaagag aaatcaggtg ctgcttgacc ttgctagttt aattttttgaa  900 gaacaacaat cattagaagt aattttgaag aaaatagctg ccactattat ctctttcatg    960
caagtgcaga aatgcaccat tttcatagtg gatgaagatt gctccgattc tttttctagt   1020
gtgtttcaca tggagtgtga ggaattagaa aaatcatctg atacattaac aagggaacat   1080
gatgcaaaca aaatcaatta catgtatgct cagtatgtca aaaatactat ggaaccactt   1140
aatatcccag atgtcagtaa ggataaaaga tttccctgga caactgaaaa tacaggaaat    1200
gtaaaccagc agtgcattag aagtttgctt tgtacaccta taaaaatgg aaagaagaat    1260 aaagttatag gggtttgcca acttgttaat aagatggagg agaatactgg caaggttaag    1320
cctttcaacc gaaatgacga acagtttctg gaagcttttg tcatcttttg tggcttgggg    1380
atccagaaca cgcagatgta tgaagcagtg gagagagcca tggccaagca aatggtcaca    1440
ttggaggttc tgtcgtatca tgcttcagca gcagaggaag aaacaagaga gctacagtcg    1500
ttagcggctg ctgtggtgcc atctgcccag acccttaaaa ttactgactt tagcttcagt    1560
gactttgagc tgtctgatct ggaaacagca ctgtgtacaa ttcggatgtt tactgacctc    1620
aaccttgtgc agaacttcca gatgaaacat gaggttctttt gcagatggat tttaagtgtt    1680
aagaagaatt atcggaagaa tgttgcctat cataattgga gacatgcctt taatacagct    1740
cagtgcatgt ttgctgctct aaaagcaggc aaaattcaga acaagctgac tgacctggag    1800
atacttgcat tgctgattgc tgcactaagc cacgatttgg atcaccgtgg tgtgaataac    1860
tcttacatac agcgaagtga acatccactt gcccagctttt actgccattc aatcatggaa    1920
caccatcatt ttgaccagtg cctgatgatt cttaatagtc caggcaatca gattctcagt    1980
ggcctctcca ttgaagaata taagaccacg ttgaaaataa tcaagcaagc tattttagct    2040
```

-continued

| | |
|---|---|
| acagacctag cactgtacat taagaggcga ggagaatttt ttgaacttat aagaaaaaat | 2100 |
| caattcaatt tggaagatcc tcatcaaaag gagttgtttt tggcaatgct gatgacagct | 2160 |
| tgtgatcttt ctgcaattac aaaaccctgg cctattcaac aacggatagc agaacttgta | 2220 |
| gcaactgaat tttttgatca aggagacaga gagagaaaag aactcaacat agaacccact | 2280 |
| gatctaatga acagggagaa gaaaaacaaa atcccaagta tgcaagttgg gttcatagat | 2340 |
| gccatctgct tgcaactgta tgaggccctg acccacgtgt cagaggactg tttccctttg | 2400 |
| ctagatggct gcagaaagaa caggcagaaa tggcaggccc ttgcagaaca gcaggagaag | 2460 |
| atgctgatta tggggaaag cggccaggcc aagcggaact ga | 2502 |

<210> SEQ ID NO 62
<211> LENGTH: 2472
<212> TYPE: DNA
<213> ORGANISM: Homo sapiens

<400> SEQUENCE: 62

| | |
|---|---|
| atggtcaatg catggtttgc tgagagagtt cacaccatcc ctgtgtgcaa ggaaggtatc | 60 |
| agaggccaca ccgaatcttg ctcttgtccc ttgcagcaga gtcctcgtgc agataacagt | 120 |
| gccctggaa caccaaccag gaaaatctct gcctctgaat ttgaccggcc tcttagaccc | 180 |
| attgttgtca aggattctga gggaactgtg agcttcctct ctgactcaga aagaaggaa | 240 |
| cagatgcctc taaccccctcc aaggtttgat catgatgaag gggaccagtg ctcaagactc | 300 |
| ttggaattag tgaaggatat ttctagtcat ttggatgtca cagccttatg tcacaaaatt | 360 |
| ttcttgcata tccatggact gatatctgct gaccgctatt ccctgttcct tgtctgtgaa | 420 |
| gacagctcca atgacaagtt tcttatcagc cgcctctttg atgttgctga aggttcaaca | 480 |
| ctggaagaag tttcaaataa ctgtatccgc ttagaatgga caaaggcat gtgggacat | 540 |
| gtggcagcgc ttggtgagcc cttgaacatc aaagatgcat atgaggatcc tcggttcaat | 600 |
| gcagaagttg accaaattac aggctacaag acacaaagca ttctttgtat gccaattaag | 660 |
| aatcataggg aagaggttgt tggtgtagcc caggccatca acaagaaatc aggaaacggt | 720 |
| gggacattta ctgaaaaaga tgaaaaggac tttgctgctt atttggcatt ttgtggtatt | 780 |
| gttcttcata tgctcagct ctatgagact tcactgctgg agaacaagag aaatcaggtg | 840 |
| ctgcttgacc ttgctagttt aatttttgaa gaacaacaat cattagaagt aattttgaag | 900 |
| aaaatagctg ccactattat ctctttcatg caagtgcaga atgcaccat tttcatagtg | 960 |
| gatgaagatt gctccgattc ttttttctagt gtgtttcaca tggagtgtga ggaattagaa | 1020 |
| aaatcatctg atacattaac aagggaacat gatgcaaaca aaatcaatta catgtatgct | 1080 |
| cagtatgtca aaaatactat ggaaccactt aatatcccag atgtcagtaa ggataaaaga | 1140 |
| tttccctgga caactgaaaa tacaggaaat gtaaaccagc agtgcattag aagtttgctt | 1200 |
| tgtacaccta taaaaatgg aaagaagaat aaagttatag gggtttgcca acttgttaat | 1260 |
| aagatggagg agaatactgg caaggttaag cctttcaacc gaaatgacga acagtttctg | 1320 |
| gaagcttttg tcatcttttg tggcttgggg atccagaaca cgcagatgta tgaagcagtg | 1380 |
| gagagagcca tggccaagca aatggtcaca ttggaggttc tgtcgtatca tgcttcagca | 1440 |
| gcagaggaag aaacaagaga gctacagtcg ttagcggctg ctgtggtgcc atctgcccag | 1500 |
| acccttaaaa ttactgactt tagcttcagt gactttgagc tgtctgatct ggaaacagca | 1560 |
| ctgtgtacaa ttcggatgtt tactgacctc aaccttgtgc agaacttcca gatgaaacat | 1620 |

```
gaggttcttt gcagatggat tttaagtgtt aagaagaatt atcggaagaa tgttgcctat    1680
cataattgga gacatgcctt taatacagct cagtgcatgt ttgctgctct aaaagcaggc    1740
aaaattcaga acaagctgac tgacctggag atacttgcat tgctgattgc tgcactaagc    1800
cacgatttgg atcaccgtgg tgtgaataac tcttacatac agcgaagtga acatccactt    1860
gcccagcttt actgccattc aatcatggaa caccatcatt ttgaccagtg cctgatgatt    1920
cttaatagtc caggcaatca gattctcagt ggcctctcca ttgaagaata taagaccacg    1980
ttgaaaataa tcaagcaagc tatttagct acagacctag cactgtacat taagaggcga     2040 ggagaattt ttgaacttat aagaaaaaat caattcaatt tggaagatcc tcatcaaaag     2100
gagttgtttt tggcaatgct gatgacagct tgtgatcttt ctgcaattac aaaaccctgg    2160
cctattcaac aacggatagc agaacttgta gcaactgaat ttttttgatca aggagacaga    2220 gagagaaaag aactcaacat agaacccact gatctaatga acaggagaa gaaaaacaaa     2280 atcccaagta tgcaagttgg gttcatagat gccatctgct tgcaactgta tgaggccctg    2340
acccacgtgt cagaggactg ttttcccttg ctagatggct gcagaaagaa caggcagaaa    2400
tggcaggccc ttgcagaaca gcaggagaag atgctgatta atggggaaag cggccaggcc    2460
aagcggaact ga                                                        2472

<210> SEQ ID NO 63
<211> LENGTH: 1023
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 63
gaagaaacaa gagagctaca gtcgttagcg gctgctgtgg tgccatctgc ccagacccct      60
aaaattactg actttagctt cagtgacttt gagctgtctg atctggaaac agcactgtgt     120
acaattcgga tgtttactga cctcaacctt gtgcagaact tccggatgaa acatgaggtt     180
ctttgcagat ggatttttaag tgttaagaag aattatcgga agaatgttgc ctatcataat     240
tggagacatg cctttaatac agctcagtgc atgtttgccg ctctaaaagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ctttactgcc attcaatcat ggaacaccat cattttgacc agtgcctgat gattcttaat     480
agtccaggca atcagattct cagtggcctc tccattgaag aatataagac cacgttgaaa     540
ataatcaagc aagctatttt agctacagac ctagcactgt acattaagag gcgaggagaa     600
ttttttgaac ttataagaaa aaatcaattc aatttggaag atcctcatca aaaggagttg     660
tttttggcaa tgctgatgac agcttgtgat ctttctgcaa ttacaaaacc ctggcctatt     720
caacaacgga tagcggaact gtagcaact gaatttttg atcaaggaga cagagagaga      780 aagaactca acatagaacc cactgatcta atgaacaggg agaagaaaa caaaatccca     840 agtatgcaag ttgggttcat agatgccatc tgcttgcaac tgtatgaggc cctgacccac     900
gtgtcagagg actgtttccc tttgctagat ggctgcaaga agaacaggca gaaatggcag    960
gcccttgcag aacagcagga gaagatgctg attaatgggg aaagcggcca ggccaagcgg    1020
aac                                                                  1023
```

<210> SEQ ID NO 64
<211> LENGTH: 1230
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 64

```
ggggtttgcc aacttgttaa taagatggag gagaatactg gcaaggttaa gcctttcaac      60
cgaaatgacg aacagtttct ggaagctttt gtcatctttt gtggcttggg gatccagaac     120
acgcagatgt atgaagcagt ggagagagcc atggccaagc aaatggtcac attggaggtt     180
ctgtcgtatc atgcttcagc agcagaggaa gaaacaagag agctacagtc gttagcggct     240
gctgtggtgc catctgccca gacccttaaa attactgact ttagcttcag tgactttgag     300
ctgtctgatc tggaaacagc actgtgtaca attcggatgt ttactgacct caaccttgtg     360
cagaacttcc ggatgaaaca tgaggttctt tgcagatgga ttttaagtgt taagaagaat     420
tatcggaaga atgttgccta tcataattgg agacatgcct taatacagc tcagtgcatg      480
tttgccgctc taaagcagg caaaattcag aacaagctga ctgacctgga gatacttgca     540
ttgctgattg ctgcactaag ccacgatttg gatcaccgtg gtgtgaataa ctcttacata     600
cagcgaagtg aacatccact tgcccagctt tactgccatt caatcatgga acaccatcat     660
tttgaccagt gcctgatgat tcttaatagt ccaggcaatc agattctcag tggcctctcc     720
attgaagaat ataagaccac gttgaaaata tcaagcaag ctatttagc tacagaccta      780
gcactgtaca ttaagaggcg aggagaattt tttgaactta taagaaaaaa tcaattcaat     840
ttggaagatc ctcatcaaaa ggagttgttt ttggcaatgc tgatgacagc ttgtgatctt     900
tctgcaatta caaaaccctg gcctattcaa caacggatag cggaacttgt agcaactgaa     960
ttttttgatc aaggagacag agagagaaaa gaactcaaca tagaacccac tgatctaatg    1020
aacagggaga agaaaaacaa aatcccaagt atgcaagttg ggttcataga tgccatctgc    1080
ttgcaactgt atgaggccct gacccacgtg tcagaggact gtttccctt gctagatggc     1140
tgcagaaaga caggcagaa atggcaggcc ttgcagaac agcaggagaa gatgctgatt     1200
aatggggaaa gcggccaggc caagcggaac                                    1230
```

<210> SEQ ID NO 65
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic Destabilizing Domain (DD)"

<400> SEQUENCE: 65

```
gaaccactta atatcccaga tgtcagtaag gataaaagat ttccctggac aactgaaaat      60
acaggaaatg taaaccagca gtgcattaga agtttgcttt gtacacctat aaaaaatgga     120
aagaagaata aagttatagg ggtttgccaa cttgttaata agatggagga gaatactggc     180
aaggttaagc ctttcaaccg aaatgacgaa cagtttctgg aagcttttgt catcttttgt     240
ggcttgggga tccagaacac gcagatgtat gaagcagtgg agagagccat ggccaagcaa     300
atggtcacat ggaggttct gtcgtatcat gcttcagcag cagaggaaga aacaagagag      360
ctacagtcgt tagcggctgc tgtggtgcca tctgcccaga cccttaaaat tactgacttt     420
```

```
agcttcagtg actttgagct gtctgatctg gaaacagcac tgtgtacaat tcggatgttt    480
actgacctca accttgtgca gaacttccgg atgaaacatg aggttctttg cagatggatt    540
ttaagtgtta agaagaatta tcggaagaat gttgcctatc ataattggag acatgccttt    600
aatacagctc agtgcatgtt tgccgctcta aaagcaggca aaattcagaa caagctgact    660
gacctggaga tacttgcatt gctgattgct gcactaagcc acgatttgga tcaccgtggt    720
gtgaataact cttacataca gcgaagtgaa catccacttg cccagctttta ctgccattca    780 atcatggaac accatcattt tgaccagtgc ctgatgattc ttaatagtcc aggcaatcag    840
attctcagtg gcctctccat tgaagaatat aagaccacgt tgaaaataat caagcaagct    900
attttagcta cagacctagc actgtacatt aagaggcgag gagaattttt tgaacttata    960
agaaaaaatc aattcaattt ggaagatcct catcaaaagg agttgttttt ggcaatgctg   1020
atgacagctt gtgatctttc tgcaattaca aaaccctggc ctattcaaca acggatagcg   1080
gaacttgtag caactgaatt ttttgatcaa ggagacagag agagaaaaga actcaacata   1140
gaacccactg atctaatgaa cagggagaag aaaaacaaaa tcccaagtat gcaagttggg   1200
ttcatagatg ccatctgctt gcaactgtat gaggccctga cccacgtgtc agaggactgt   1260 ttcccttttgc tagatggctg cagaaagaac aggcagaaat ggcaggccct tgcagaacag   1320
caggagaaga tgctgattaa tggggaaagc ggccaggcca agcggaac                1368
```

<210> SEQ ID NO 66
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 66

```
Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Arg Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Glu Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Ser Leu Lys Ile Ile Lys Gln Ala Ile Leu Ala Thr Asp Leu Ala
            180                 185                 190
```

```
Leu Tyr Ile Lys Arg Arg Gly Glu Phe Phe Glu Leu Ile Arg Lys Asn
            195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255

Asp Arg Glu Arg Glu Leu Asn Ile Glu Pro Thr Asp Leu Met Asn
            260                 265                 270

Arg Glu Lys Lys Asn Lys Ile Pro Ser Met Gln Val Gly Phe Ile Asp
            275                 280                 285

Ala Ile Cys Leu Gln Leu Tyr Glu Ala Leu Thr His Val Ser Glu Asp
            290                 295                 300

Cys Phe Pro Leu Leu Asp Gly Cys Arg Lys Asn Arg Gln Glu Trp Gln
305                 310                 315                 320

Ala Leu Ala Glu Gln Gln
                325

<210> SEQ ID NO 67
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 67

Glu Gly Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
            35                  40                  45

Asn Leu Val Gln Asn Phe Arg Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
            115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
            195                 200                 205
```

```
Gln Phe Asn Leu Glu Asp Pro His Gln Lys Glu Leu Phe Ala Met
    210                 215                 220
Leu Met Thr Ala Cys Asp Leu Ser Ala Ile Thr Lys Pro Trp Pro Ile
225                 230                 235                 240
Gln Gln Arg Ile Ala Glu Leu Val Ala Thr Glu Phe Phe Asp Gln Gly
            245                 250                 255
Asp Arg Glu Arg Lys Glu Leu Asn Ile Glu Pro Thr Asp Leu Met Asn
            260                 265                 270
Arg Glu Lys Asn Lys Ile Pro Ser Met Gln Val Gly Phe Ile Asp
        275                 280                 285
Ala Ile Cys Leu Gln Leu Tyr Glu Ala Leu Thr His Val Ser Glu Asp
290                 295                 300
Ser Phe Pro Leu Leu Asp Gly Cys Arg Lys Asn Arg Gln Lys Trp Gln
305                 310                 315                 320
Ala Leu Ala Glu Gln Gln
            325

<210> SEQ ID NO 68
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 68

Glu Glu Thr Arg Glu Leu Gln Ser Leu Ala Ala Val Val Pro Ser
1               5                   10                  15
Ala Gln Thr Leu Lys Ile Thr Asp Phe Ser Phe Ser Asp Phe Glu Leu
            20                  25                  30
Ser Asp Leu Glu Thr Ala Leu Cys Thr Ile Arg Met Phe Thr Asp Leu
        35                  40                  45
Asn Leu Val Gln Ser Phe Arg Met Lys His Glu Val Leu Cys Arg Trp
    50                  55                  60
Ile Leu Ser Val Lys Lys Asn Tyr Arg Glu Asn Val Ala Tyr His Asn
65                  70                  75                  80
Trp Arg His Ala Phe Asn Thr Ala Gln Cys Met Phe Ala Ala Leu Lys
                85                  90                  95
Ala Gly Lys Ile Gln Asn Lys Leu Thr Asp Leu Glu Ile Leu Ala Leu
            100                 105                 110
Leu Ile Ala Ala Leu Ser His Asp Leu Asp His Arg Gly Val Ser Asn
        115                 120                 125
Ser Tyr Ile Gln Arg Ser Glu His Pro Leu Ala Gln Leu Tyr Cys His
    130                 135                 140
Ser Ile Met Glu His His His Phe Asp Gln Cys Leu Met Ile Leu Asn
145                 150                 155                 160
Ser Pro Gly Asn Gln Ile Leu Ser Gly Leu Ser Ile Glu Glu Tyr Lys
                165                 170                 175
Thr Thr Leu Lys Ile Ile Lys Gln Ala Ile Leu Ala Thr Asp Leu Ala
            180                 185                 190
Leu Tyr Ile Lys Arg Arg Gly Glu Phe Phe Glu Leu Ile Arg Lys Asn
        195                 200                 205
Gln Phe Asn Leu Glu Asp Pro His Gln Lys Glu Leu Phe Leu Ala Met
    210                 215                 220
Leu Met Thr Ala Cys Val Leu Ser Ala Ile Thr Lys Pro Trp Pro Ile
225                 230                 235                 240
```

```
225                 230                 235                 240
Gln Gln Arg Ile Ala Glu Leu Val Ala Thr Glu Phe Phe Asp Gln Gly
                245                 250                 255

Asp Arg Glu Arg Lys Glu Leu Asn Ile Glu Pro Thr Asp Leu Met Asn
                260                 265                 270

Arg Glu Lys Lys Asn Lys Ile Pro Ser Met Gln Val Gly Phe Ile Asp
                275                 280                 285

Ala Ile Cys Leu Gln Leu Tyr Glu Ala Leu Thr His Val Ser Glu Asp
                290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 69
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 69

Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
                20                  25                  30

Ser Asp Leu Glu Thr Ala Leu Cys Thr Ile Arg Met Phe Thr Asp Leu
                35                  40                  45

Asn Leu Val Gln Asn Phe Arg Met Lys His Glu Val Leu Cys Arg Trp
            50                  55                  60

Ile Leu Ser Val Lys Lys Asn Tyr Arg Lys Asn Val Ala Tyr His Asn
65              70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
                100                 105                 110

Leu Ile Ala Ala Leu Ser His Asp Leu Asp His Arg Gly Val Asn Asn
                115                 120                 125

Ser Tyr Ile Gln Arg Ser Glu His Pro Leu Ala Gln Pro Tyr Cys His
                130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
                180                 185                 190

Leu Tyr Ile Lys Arg Arg Gly Glu Phe Phe Glu Leu Ile Arg Lys Asn
                195                 200                 205

Gln Phe Asn Leu Glu Asp Pro His Gln Lys Glu Leu Leu Leu Ala Met
                210                 215                 220

Leu Met Thr Ala Cys Asp Leu Ser Ala Ile Thr Lys Pro Trp Pro Ile
225                 230                 235                 240

Gln Gln Arg Ile Ala Glu Leu Val Ala Thr Glu Phe Phe Asp Gln Gly
                245                 250                 255
```

```
Asp Arg Glu Arg Lys Glu Leu Asn Ile Glu Pro Thr Asp Leu Met Asn
            260                 265                 270

Arg Glu Lys Lys Asn Lys Ile Pro Ser Met Gln Val Gly Phe Ile Asp
        275                 280                 285

Ala Ile Cys Leu Gln Leu Tyr Glu Ala Leu Thr His Val Ser Glu Asp
    290                 295                 300

Cys Phe Pro Leu Leu Asp Gly Cys Arg Lys Asn Arg Gln Lys Trp Gln
305                 310                 315                 320

Ala Leu Ala Glu Gln Gln
                325

<210> SEQ ID NO 70
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 70
gaagaaacaa gagagctaca gtcgttagcg gctgctgtgg tgccatctgc ccagaccctt      60
aaaattactg actttagctt cagtgacttt gagctgtctg atctggaaac agcactgtgt     120
acaattcgga tgtttactga cctcaacctt gtgcagaact tccggatgaa acatgaggtt     180 cttttgcagat ggattttaag tgttaagaag aattatcgga agaatgttgc ctatcataat    240
tggagacatg cctttaatac agctcagtgc atgtttgccg ctctaaaagc aggcgaaatt    300
cagaacaagc tgactgacct ggagatactt gcattgctga ttgctgcact aagccacgat    360
ttggatcacc gtggtgtgaa taactcttac atacagcgaa gtgaacaccc acttgcccag    420
ctttactgcc attcaatcat ggaacaccat catttttgacc agtgcctgat gattcttaat    480
agtccaggca atcagattct cagtggcctc tccattgaag aatataagac ctcgttgaaa    540
ataatcaagc aagctatttt agctacagac ctagcactgt acattaagag gcgaggagaa    600 tttttttgaac ttataagaaa aaatcaattc aatttggaag atcctcatca aaaggagttg    660
tttttggcaa tgctgatgac agcttgtgat cttttctgcaa ttacaaaacc ctggccaatt    720
caacaacgga tagcggaact tgtagcaact gaattttttg atcaaggaga cagagagaga    780
gaagaactca acatagaacc cactgatcta atgaacagga gaagaaaaa caaaatccca    840 agtatgcaag ttgggttcat agatgccatc tgcttgcaac tgtatgaggc cctgacccac    900
gtgtcagagg actgtttccc tttgctagat ggctgcagaa agaacaggca ggaatggcag    960
gcccttgcag aacagcag                                                  978

<210> SEQ ID NO 71
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 71
gaaggaacaa gagagctaca gtcgttagcg gctgctgtgg tgccatctgc ccagaccctt      60
aaaattactg actttagctt cagtgacttt gagctgtctg atctggaaac agcactgtgt     120
acaattcgga tgtttactga cctcaacctt gtgcagaact tccggatgaa acatgaggtt     180
```

```
ctttgcagat ggattttaag tgttaagaag aattatcgga agaatgttgc ctatcataat      240
tggagacatg cctttaatac agctcagtgc atgtttgccg ctctaaaagc aggcaaaatt      300
cagaacaagc tgactgacct ggagatactt gcattgctga ttgctgcact aagccacgat      360
ttggatcacc gtggtgtgaa taactcttac atacagcgaa gtgaacatcc acttgcccag      420
ctttactgcc attctatcat ggaacaccat cattttgacc agtgcctgat gattcttaat      480
agtccaggca atcagattct cagtggcctc tccattgaag aatataagac cacgttgaaa      540
ataatcaagc aagctatttt agcaacagac ctagcactgt acattaagag gcgaggagaa      600
ttttttgaac ttataagaaa aaatcaattc aatttggaag atcctcatca aaaggagttg      660
tttttggcaa tgctgatgac agcttgtgat ctttctgcaa ttacaaaacc ctggcctatt      720
caacaacgga tagcggaact tgtagcaact gaatttttg atcaaggaga cagagagaga       780
aaagaactca acatagaacc cactgatcta atgaacaggg agaagaaaaa caaaatccca      840
agtatgcaag ttgggttcat agacgccatc tgcttgcaac tgtatgaggc cctgacccac      900
gtgtcagagg acagtttccc tttgctagat ggctgcagaa agaacaggca gaaatggcag      960
gcccttgcag aacagcag                                                   978
```

<210> SEQ ID NO 72
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Destabilizing Domain (DD)"

<400> SEQUENCE: 72

```
gaagaaacaa gagagctaca gtcgttagcg gctgctgtgg tgccatctgc ccagacccct       60
aaaattactg actttagctt cagtgacttt gagctgtctg atctggaaac agcactgtgt      120
acaattcgga tgtttactga cctcaacctt gtgcagagct tccggatgaa acatgaggtt      180
ctttgcagat ggattttaag tgttaagaag aattatcggg agaatgttgc ctatcataat      240
tggagacatg cctttaatac agctcagtgc atgtttgccg ctctaaaagc aggcaaaatt      300
cagaacaagc tgactgacct ggagatactt gcattgctga ttgctgcact aagccacgat      360
ttggatcacc gtggtgtgag taactcttac atacagcgaa gtgaacatcc acttgcccag      420
ctttactgcc attcaatcat ggaacaccat cattttgacc agtgcctgat gattcttaat      480
agtccaggca atcagattct cagtggcctc tccattgaag aatataagac cacgttgaaa      540
ataatcaagc aagctatttt agctacagac ctagcactgt acattaagag gcgaggagaa      600
ttttttgaac ttataagaaa aaatcaattc aatttggaag atcctcatca aaaggagttg      660
tttttggcaa tgctgatgac agcttgtgtt ctttctgcaa ttacaaaacc ctggcctatt      720
caacaacgga tagcggaact tgtagcaact gaatttttg atcaaggaga cagagagaga       780
aaagaactca acatagaacc cactgatcta atgaacaggg agaagaaaaa caaaatccca      840
agtatgcaag ttgggttcat agatgccatc tgcttgcaac tgtatgaggc cctgacccac      900
gtgtcagagg actgtttccc tttgctagat ggctgcagaa agaacaggca gaaatggcag      960
gcccttgcag aacagcag                                                   978
```

<210> SEQ ID NO 73
<211> LENGTH: 978
<212> TYPE: DNA

<213> ORGANISM: Artificial Sequence
<220> FEATURE:
<221> NAME/KEY: source
<223> OTHER INFORMATION: /note="Description of Artificial Sequence:
    Synthetic Destabilizing Domain (DD)"

<400> SEQUENCE: 73

```
gaagaaacaa gagagctaca gtcgttagcg gctgctgtgg tgccatctgc ccagacccctt      60
aaaattactg actttagctt cagtgacttt gagctgtctg atctggaaac agcactgtgt     120
acaattcgga tgtttactga cctcaacctt gtgcagaact tccggatgaa acatgaggtt     180
ctttgcagat ggattttaag tgttaagaag aattatcgga agaatgttgc ctatcataat     240
tggagacatg cctttaatac agctcagtgc atgtttgccg ctctaaaagc aggcaaaatt     300
cagaacaagc tgactgacct ggagatactt gcattgctga ttgctgcact aagccacgat     360
ttggatcacc gtggtgtgaa taactcttac atacagcgaa gtgaacatcc acttgcccag     420
ccttactgcc attcaatcat ggaacaccat cattttgacc agtgcctgat gattcttaat     480
agtccaggca atcagattct cagtggcctc tccattgaag aatataagac cacgttgaaa     540
ataatcaagc aagctatttt agctacagac ctagcactgt acattaagag gcgaggagaa     600
ttttttgaac ttataagaaa aaatcaattc aatttggaag atcctcatca aaaggagttg     660
ttgttggcaa tgctgatgac agcttgtgat ctttctgcaa ttacaaaacc ctggcctatt     720
caacaacgga tagcggaact cgtagcaact gaatttttttg atcaaggaga cagagagaga     780
aaagaactca acatagaacc cactgatcta atgaacaggg agaagaaaaa caaaatccca     840
agtatgcaag ttgggttcat agatgccatc tgcttgcaac tgtatgaggc cctgacccac     900
gtgtcagagg actgtttccc tttgctagat ggctgcagaa agaacaggca gaaatggcag     960
gcccttgcag aacagcag                                                   978
```

<210> SEQ ID NO 74
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic Tag"

<400> SEQUENCE: 74

Tyr Pro Tyr Asp Val Pro Asp Tyr Ala
1               5

<210> SEQ ID NO 75
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic Tag"

<400> SEQUENCE: 75

```
tatccgtacg acgtaccaga ctacgca                                           27
```

<210> SEQ ID NO 76
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic POI sequence"

<400> SEQUENCE: 76

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys
225                 230                 235

<210> SEQ ID NO 77
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic POI sequence"

<400> SEQUENCE: 77
atggtgagca agggcgccga gctgttcacc ggcatcgtgc ccatcctgat cgagctgaat     60
ggcgatgtga atggccacaa gttcagcgtg agcggcgagg gcgagggcga tgccacctac    120
ggcaagctga ccctgaagtt catctgcacc accggcaagc tgcctgtgcc ctggcccacc    180
ctggtgacca cccctgagcta cggcgtgcag tgcttctcac gctaccccga tcacatgaag    240
cagcacgact tcttcaagag cgccatgcct gagggctaca tccaggagcg caccatcttc    300
ttcgaggatg acggcaacta caagtcgcgc gccgaggtga agttcgaggg cgataccctg    360
gtgaatcgca tcgagctgac cggcaccgat ttcaaggagg atggcaacat cctgggcaat    420
aagatggagt acaactacaa cgcccacaat gtgtacatca tgaccgacaa ggccaagaat    480
ggcatcaagg tgaacttcaa gatccgccac aacatcgagg atggcagcgt gcagctggcc    540

-continued

```
gaccactacc agcagaatac ccccatcggc gatggccctg tgctgctgcc cgataaccac    600
tacctgtcca cccagagcgc cctgtccaag gaccccaacg agaagcgcga tcacatgatc    660
tacttcggct tcgtgaccgc cgccgccatc acccacggca tggatgagct gtacaag       717
```

PDE5A DESTABILIZING DOMAINS

CROSS-REFERENCE TO RELATED APPLICATIONS

This application is a U.S. National Stage Application under 35 U.S.C. § 371 which claims the benefit of priority to International Patent Application No. PCT/US2018/039096, filed Jun. 22, 2018, which claims the benefit of priority to U.S. Provisional Patent Application No. 62/524,384 filed on Jun. 23, 2017, each of which is hereby incorporated by reference in its entirety.

STATEMENT REGARDING FEDERALLY SPONSORED RESEARCH OR DEVELOPMENT

This section intentionally left blank.

REFERENCE TO THE SEQUENCE LISTING

This application contains a Sequence Listing which has been filed electronically in ASCII format and is hereby incorporated by reference in its entirety. The ASCII copy, created on Jun. 22, 2018, is named 091511-0624_8285 WO00_SL.txt and is 213,645 bytes in size.

TECHNICAL FIELD

Rapid and reversible methods for destabilizing specific proteins using cell permeable, synthetic molecules are described. Variants of the human PDE5A proteins that are rapidly and constitutively degraded in the cells confer instability to the fusion proteins. Addition of a ligand that binds to the variant destabilizing domain prevents protein degradation, allowing the biological function of the fusion protein to be studied in detail.

BACKGROUND

The ability to control the abundance of a specific protein in cells represents a powerful approach to interrogating complex biological behavior and in gene therapy. One of the most well-established ways to modulate protein activity is to knockdown the corresponding gene-of-interest either by targeting its precursor DNA or RNA molecules. While recent advances in genome editing tools have significantly improved the efficiency of perturbing specific genes, such efforts can be laborious and are not readily reversible. Alternatively, RNAi allows researchers to more quickly assess the effects of gene silencing; however, this approach is often plagued by incomplete knockdown, off-target specificity, and other nonspecific interactions. Because each of these approaches modulates a protein indirectly, they ultimately suffer from long experimental delays, given that the previously transcribed and synthesized protein molecules must be degraded before effects can be observed.

To circumvent the challenges modulating gene-of-interest, approaches that directly control protein level using cell permeable small molecules have been developed. These approaches directly recruit enzymes involved in the ubiquitin-proteasome system (UPS) to the protein of interest (POI), thereby promoting its degradation. One approach involves a cell-permeable ligand that is used in conjunction with a single genetically encoded domain to regulate any protein of interest, to which the domain is genetically fused. Mutants of domains (proteins) are engineered to be metabolically unstable in the absence of their high affinity ligand and are referred to as the destabilizing domains (DDs) (Stankunas, K., et al., (2003). *Mol. Cell* 12, 1615-1624; Banaszynski, L. A., et al., (2006) *Cell,* 126(5): 995-1004; reviewed in Banaszynski, L. A., and Wandless, T. J. (2006) *Chem. Biol.* 13, 11-21; Iwamoto, M., et al. (2010). *Chem Biol.* 17(9):981-8; Egeler, E. L. et al. (2011). *J Biol Chem.* 286(36):31328-36; and Rakhit R, Navarro R, Wandless T J (2014) *Chem Biol.* Sep 18; 21(9):1238-52; Navarro, R. et al. (2016) *ACS Chem Biol.* 11(8): 2101-2104). The instability of a DD, conferred to any fused partner protein results in degradation of the entire protein by the proteasome. The high affinity ligand binds to and stabilizes the DD in a dose dependent manner. The genetic fusion of the DD to the protein of interest ensures specificity, and small-molecule control confers reversibility and dose-dependence to protein stability and function.

A system as herein described, is a ligand regulated protein stability system, with the Destabilizing Domains containing protein stability systems as the prototype model. Controlling protein function using protein stability systems described herein is a more attractive approach than targeting precursor DNA or mRNA, as targeting of protein is rapid and is not limited by the intrinsic half-life of targeted proteins.

Provided are novel protein domains, in particular, destabilizing domains derived from human cGMP-specific Phosphodiesterase type 5A (PDE5A), particularly, the catalytic domain of human PDE5A, that displays small molecule dependent ligand stability; and the protein stability systems comprising such DDs. Methods for conditionally stabilizing proteins using the same are also provided.

BRIEF SUMMARY

Provided herein are novel protein domains displaying ligand dependent stability. Such protein domains are called destabilizing domains (DDs). In the absence of its binding ligand, the DD is destabilizing and causes degradation of a payload fused to the DD (e.g., a protein of interest (POI), while in the presence of its binding ligand, the fused DD and payload can be stabilized and its stability is dose dependent.

In some aspects, conditional protein stability systems are provided, the systems comprising a protein of interest fused in-frame to a single-protein, ligand dependent destabilization domain derived from a region or portion of human PDE5A. The destabilization domain may be derived from the catalytic domain of PDE5A and/or the GAF domain; and may include one or more amino acid substitutions selected from E535D, E536G, Q541R, K555R, F559L S560G, F561L, F564L, F564S, V585A, N587S, K591E, I599V, K604E, K608E, N609H, K630R, K633E, N636S, I648V, N661S, S663P, L675P, Y676D, Y676N, C677R, H678R, D687A, T711A, T712S, D724N, L738H, N742S, F744L, L746S, F755L, A762S, D764V, D764N, D764G, S766F, K795E, L797F, I799T, L804P,T802P, S815C, M816A, M816T, I824T, C839S, F840S, and K852E. The PDE5A derived DDs may also contain additional substitutions such as Q589R. In some embodiments, the conditional protein stability system comprises a destabilizing domain selected from the group of amino acid sequences identified by SEQ ID NOs. 19-35 (encoded by SEQ ID NOs. 36-52) and SEQ ID NOs.66-69 (encoded by SEQ ID NO. 70-73).

In some embodiments, the ligand may be Sildenafil, Vardenafil, Tadalafil, Avanafil, Lodenafil, Mirodenafil, Udenafil, Benzamidenafil, Dasantafil, or Beminafil.

In one embodiment, cells comprising nucleic acids encoding a fusion protein comprising a protein of interest fused in frame to a PDE5A derived destabilizing domain are provided. In some embodiments, the cells are in an organism. In another aspect, a kit of parts comprising PDE5A derived DDs is provided.

Methods for conditionally stabilizing a protein of interest, using the DDs, systems and compositions are also provided.

In addition to the exemplary aspects and embodiments described above, further aspects and embodiments will become apparent by reference to the drawings and by study of the following descriptions.

DETAILED DESCRIPTION

I. Introduction

Figure 1:
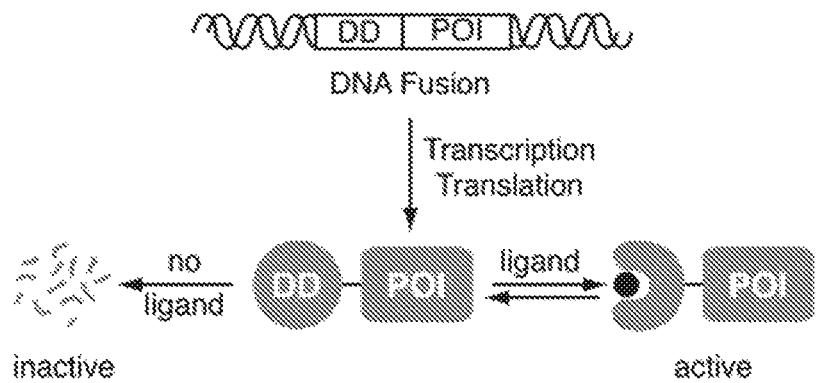
FIG. 1 illustrates a method for conditionally controlling protein stability. A genetic fusion of a destabilizing domain (DD) to a protein of interest (PO) results in degradation of the entire fusion protein. Addition of a ligand for the destabilizing domain protects the fusion protein from degradation.

Techniques for modulating transcription of DNA and RNA expression provide powerful tools for studying specific genes and their biological function. For example, the tet/dox, and Cre/lox systems have been widely used to target gene expression at the transcriptional level (Ryding A. D. S. et al. (2001), *J. Endocrinol.* 171:1-14) and RNA interference provides a method to achieve post-transcriptional gene silencing Fire, A. et al. (1998) *Nature* 391:806-811; Medema, R. H. (2004) *Biochem. J.* 380:593-603; Raab, R. M. and Stephanopoulos, G. (2004) *Biotechnology & Bioengineering* 88:121-132).

Techniques have also been developed to regulate proteins on a post-translational level. Experimental methods have been developed to regulate protein stability and function rapidly and reversibly using protein domains that are conditionally stable in cultured cell or living animals. Such methods are often controlled by the binding of a small molecule ligand (Baker, M. (2012) *Nat. Methods* 9, 443-447). Methods to conditionally regulate protein abundance in cells are useful to biologists to study a protein's function(s) in complex biological systems. However, methods for regulating protein function directly are limited, especially in mammalian cells. Inhibitors or activators of particular proteins have been identified, and often take the form of cell permeable small molecules. Many of these molecules have found widespread use as biological probes, often because the speed, dosage-dependence, and reversibility of their activities, which complement methods for genetically modulating (Schreiber, S. L. (2003) *Chem. & Eng. News* 81:51-61). However, these inhibitors or activators are often promiscuous, affecting several proteins rather than a specific protein (Davies, S. P. et al. (2000) *Biochem. J.* 351:95-105; Bain, J. et al. (2003) *Biochem. J.* 371:199-204; Godl, K. et al. (2003) *Proc. Natl. Acad. Sci. U.S.A.* 100: 15434-15439; Tan, D. S. (2005) *Nat. Chem. Biol.* 1:74-84; Mayer, T. U. et al. (1999) *Science,* 286:971-974).

A method by which specific kinases can be inhibited using a small molecule modulator has also been developed (Bishop, A. C. et al. (1998) *Current Biology* 8:257-266). This method involved mutating a protein of interest, typically replacing a large conserved residue in the active site with a smaller residue, such as glycine or alanine. Specificity is achieved by chemically modifying a promiscuous inhibitor to include a bulky side-chain substituent (e.g. R-group), which fills the corresponding cavity in the binding site of the modified protein of interest, while preventing the productive interactions with other kinases. While this so called "bump-hole" approach has been successful both in cultured cells and in mice Bishop, A. C. et al. (2000) *Nature* 407:395-401; Wang, H. et al. (2003) *Proc. Natl. Acad. Sci. U.S.A.* 100: 4287-4292, Chen, X. et al. (2005) *Neuron* 46:13-21), it appears to be limited to ATPases and GTPases. Additional methods are required to probe the function of a wider variety of proteins.

Alternative strategies to perturb protein function by exploring existing cellular processes have been devised. For example, a method has been developed for controlling protein function based on the importance of certain N-terminal residues for protein stability (Bachmair, A. et al. (1986). *Science* 234:179-186). Szostak and coworkers showed that a small peptide sequence could be fused to the N-terminus of a protein of interest to modulate protein stability (Park, E-C. et al. (1992) *Proc. Natl. Acad. Sci. U.S.A.* 89:1249-1252). Varshaysky and coworkers have further isolated a temperature sensitive peptide sequence that greatly reduced the half-life of dihydrofolate reductase (DHFR) at the non-permissive temperature (Dohmen, R. J. et al. (1994) *Science* 263:1273-1276). This approach has been used to study proteins in yeast (Labib, K. et al. (2000) *Science* 288:1643-1646; Kanemaki, M. et al. (2003) *Nature* 423:720-724). Furthermore, dimeric small molecules have been engineered to conditionally target fusion proteins for degradation via E3 ligase or the proteasome, itself (Janse, D. M. et al. (2004) *J. Biol. Chem.* 279:21415-21420). However, these systems require either a prior knowledge of the high-affinity ligands that modulate the activity of a protein of interest or they are restricted to genetically engineered yeast strains.

An alternative approach for controlling protein function directly is to interfere with subcellular localization. For example, several methods have been developed to regulate protein localization using a small molecule by taking advantage of the FKBP-FRB ternary complex (Kohler, J. J. et al. (2003) *Chem. Biol.* 10:1303-1331; Inoue, T. et al. (2005) *Nature Methods* 2:415-418). Rapamycin and FK506 are potent, commercially available immunosuppressive agents, which are ligands of the FK506-binding protein (FKBP12, FKBP). Rapamycin also binds to FKBP-rapamycin-associated protein (FRAP). FRAP is also called the mammalian target of rapamycin (mTOR), rapamycin and FKBP target 1 (RAFT1), and FKBP-rapamycin-binding (FRB). Rapamycin binds to and inhibits FRAP/mTOR by interacting with its FRB domain to inhibit/delay G1 cell cycle progression in mammalian cells (see, e.g. Choi, J. et al. (1996) Science 273:239-42 and Vilella-Bach, M. et al. (1999) J. Biol. Chem. 274:4266-72. The FRB domain is required for FKBP-rapamycin-associated protein kinase activity and G1 progression. Fusions of proteins of interest can be made to either FKBP or to the FRP domain of FRAP/mTOR. Colocalization of the protein of interest is induced upon addition of rapamycin. Because rapamycin has inherent biological activity, researchers have developed a "bump-hole" strategy (similar to that described above), wherein rapamycin derivatives possessing large substituents at the FRB binding interface bind poorly to the wild-type FRB domain and thus the target FRAP/mTOR; binding is restored upon introduction of compensatory cavity-forming mutations in FRB. Specifically, a C20-methallyl-rapamycin derivative (MaRap) binds to a triple-mutated variant of FRB called FRB* (Liberles, S. D. et al. (1997) *Proc. Natl. Acad. Sci. U.S.A.* 94:7825-7830).

Recently, numerous applications have been described employing light responsive protein domains. The LOV (Light-Oxygen-Voltage) domains are part of plant photoreceptor proteins and detect blue light via a flavin cofactor (Herrou, J. et al. *Nat. Rev. Microbiol.* 9, 713-723 (2011)). The LOV2 domain of oat phototropin 1 (AsLOV2) holds a c-terminal alpha helix that is tightly bound to the LOV core domain in dark. Exposure to light results in unfolding of the helix. The AsLOV2 domain has been used to regulate certain protein activities by the steric inhibition of an effector protein or by restricting a specific protein conformation. (Wu, Y. I. et al. (2009) *Nature* 461, 104-108; Lee, J. et al. (2008) *Science* 322, 438-442; Strickland, D., et al. (2008) *Proc. Natl. Acad. Sci. USA* 105, 10709-10714). These methods are suitable for the reported engineered proteins but not generally applicable to other proteins. Alternatively, engineered AsLOV2 and other photosensory domains have been used to establish light mediated protein-protein interactions (Shimizu-Sato, S., et al. (2002) *Nat. Biotechnol.* 20, 1041-1044; Levskaya, A., et al. (2009) *Nature* 461, 997-1001; Yazawa, M., et al. (2009) *Nat. Biotechnol.* 27, 941-945; Kennedy, M. J. et al. (2010) *Nat. Methods* 7, 973-975; Strickland, D. et al. (2012) *Nat. Methods* 9, 379-384; Wang, X., et al. (2012) *Nat. Methods* 9, 266-269; Polstein, L. R. et al. (2012) *J. Am. Chem. Soc.* 134, 16480-16483; Lungu, O. I., et al. (2012) *Chem. Biol.* 19, 507-517; Zhou, X. X. et al. (2012) *Science* 338, 810-814). Thus, translocation strategies to the cell membrane or the nucleus can allow location specific protein activity and light induced gene expression systems respectively. These technologies may be useful in some cases, but they often lack the ability to control protein levels once present in the cells, and none of the existing methods developed so far is suitable for fast and reversible regulation of protein levels. Furthermore, while the aforementioned methods for regulating protein function directly are noteworthy, a need remains for a convenient, general method for regulating protein function, particularly a method that does not require the interaction of multiple proteins. Regulation of protein stability in cells in a more spatial or temporal manner is also desirable.

Building on the FRB* domain system, Banaszynski et al., developed a cell permeable ligand system of mutants of FKBP12 which are engineered to be unstable in the absence of a high affinity ligand, Shield-1 (Banaszynski et al., *Cell*. (2006); 126:995-1004). They termed these unstable domains, destabilizing domains (DDs). The FKBP/shield-1 tuning system has been successfully used in several studies to control target proteins. For example, Dettwier et al., fused FKBP to tune the express of NADPH P450 oxidoreductase (POR) (Dettwier et al., *PLoS One*, 2014, 9(11): e113540). The FKBP DD-shield system has been used in cell lines, transgenic mice, protozoan Entamoeba *histolytica*, the flatworm Caenorhabditis *elegans*, the *medaka*, and transgenic xenografts to investigate the activity of a protein of interest (Maynard-Smith et al., (2007), *J Biol Chem.* 282(34): 24866-24872; Liu et al., (2014) *Int J Parasitol.*, 44(10):729-735; Cho et al., (2013) *PLoS One.*, 8(8): e72393; Banaszynski et al. (2008) *Nat Med*, 14(10):1123-1127; Rodriguez and Wolfgang, (2011) *Chem Biol.*, 19(3):391-398; and Froschauer et al., (2015) *PLoS One*, 10(7): e0131252), for iPSC reprogramming (Sui et al., (2014) *Stem cell Reports.*, 2(5): 721-733).

Other DD ligand pairs include estrogen receptor domains which can be regulated by several estrogen receptor antagonists (Miyazaki et al., (2012) *J Am Chem. Soc*, 134(9): 3942-3945), and fluorescent destabilizing domain (FDD) derived from bilirubin-inducible fluorescent protein, UnaG. A FDD and its cognate ligand bilirubin (BR) can induce degradation of a protein fused to the FDD (Navarro et al. (2016) *ACS Chem Biol*, June 6, Epub). Other known DDs and their applications in protein stability include those described in U.S. Pat. Nos. 8,173,792 and 8,530,636, the contents of which are each incorporated herein by reference in their entirety.

In an orthogonal approach, the destabilizing domains of the bacterial dihydrofolate reductase (ecDHFR) were explored. (Iwamoto et al. (2010) *Chem Biol.*, 17(9):981-988; and Tai et al. (2012), *PLoS One*. 7(9): e46269). Numerous inhibitors of DHFR have been developed as drugs and one such inhibitor Trimethoprim (TMP), inhibits ecDHFR much more potently than mammalian DHFR providing specificity to the interaction (Iwamoto, et al., (2010) *Chem Biol*. September 24; 17(9): 981-988).

The present findings expand upon the technology of conditional protein stability systems by utilizing destabilizing domains derived from human PDE5A protein. The destabilization and stabilization of a protein of interest can be controlled by PDE5A derived DDs having stabilizing or destabilizing properties and their ligands e.g. Sildenafil and Vardenafil which bind to such protein domains. The presence and/or absence of the ligand can conditionally stabilize the protein of interest that is genetically fused to the protein of interest.

II. Compositions

Described herein are compositions, systems and methods for modulating the stability and function of proteins rapidly and reversibly, in vitro and in vivo, through the administration of cell-permeable small molecules to cultured cells or living animals. The coding sequence for a protein of interest (POI) is genetically fused to a sequence encoding a stability-affecting protein domain capable of interacting with a small-molecule ligand, the presence, absence, or amount of which ligand modulates the stability of the fusion protein. These compositions, systems and methods are designed to provide (1) protein domains in the form of cDNA constructs that, when fused to any gene-of-interest, can be used by investigators to degrade proteins-of-interest; and (2) cell-permeable small molecules that bind to and stabilize the destabilizing domains (DD), thereby restoring the function of the protein-of-interest. A feature of the conditional system is that it is a "single ligand domain" system, which minimizes the number of components in the system and the complexity of the system.

In some embodiments, provided are ligand-regulated conditional protein stability systems which enable the stability of a protein of interest to be modulated (i.e. manipulated or controlled), following its expression. In conditional protein stability systems described herein, stability is modulated by adding an amount of a stabilizing ligand, which binds to a fusion protein containing a destabilizing protein domain fused to a POI, thereby stabilizing the fusion protein and allowing the POI to function in the cell. As used herein, "POI" refers to any protein, or functional fragment or derivative, thereof, that one skilled in the art wishes to study, or for which, one desires to conditionally destabilize and regulate the degradation of the protein functional fragment or derivative thereof. Described herein are ligand regulated protein stability systems and destabilizing protein domains comprising PDE5A derived destabilizing domains. The overall architecture of the ligand regulated protein stability system is presented in FIG. 1. Introducing a fusion protein consisting of the DD and the protein interest into a cell results in the expression of the protein. The stability of the fusion protein is modulated upon administration of the ligand.

In some embodiments, stability of the fusion protein is increased upon administration of the ligand. This strategy is referred to as the "drug-on" in that the stabilizing ligand must be present for the expression of the desired fusion protein. However, if the POI exhibits a dominant negative phenotype, the system may effectively be "drug-off" in that removal of the stabilizing ligand is required for the expression of the desired fusion protein. In this embodiment, addition of a stabilizing ligand results in the stabilization of the fusion protein and loss of function of the target protein. A similar situation may exist if a constitutively active variant of a protein e.g. an oncogene, was placed under the control of a ligand responsive fusion protein, wherein the addition of ligand (rather than its withdrawal) triggers the event of interest and ensures the specificity of the conditional stabilization. This may result in a decrease in the stability of the fusion protein upon administration of the ligand.

Preferred destabilizing domains direct the degradation of a fusion protein in the absence of a stabilizing small molecule. Preferred destabilization domains reduce the amount of fusion protein present in a cell to less than 20%, less than 10%, less than 5%, less than 2% or even less than 1% of the amount of the fusion protein present upon the addition of the stabilizing ligand, or compared to the amount of the naturally-occurring POI (i.e. the native protein, not a fusion protein). In this context, the naturally occurring POI is deleted or disrupted in the genome of the cells or animal in which the conditional protein stability system is used or replaced by a DNA encoding the fusion protein. In this manner, the only source of the POI is the conditionally stabilized fusion protein, allowing its function to be studied in the absence of interfering wildtype/naturally-occurring protein.

In some embodiments, methods for modulating protein, expression, function or level by measuring the stabilization ratio are provided. As used herein, the stabilization ratio may be defined as the ratio of expression, function or level of a protein of interest in response to the ligand to the expression, function or level of the protein of interest in the absence of the ligand specific to the destabilizing domain. In some aspects, the stabilization ratio is at least 1, such as by at least 1-10, 1-20, 1-30, 1-40, 1-50, 1-60, 1-70, 1-80, 1-90, 1-100, 20-30, 20-40, 20-50, 20-60, 20-70, 20-80, 20-90, 20-95, 20-100, 30-40, 30-50, 30-60, 30-70, 30-80, 30-90, 30-95, 30-100, 40-50, 40-60, 40-70, 40-80, 40-90, 40-95, 40-100, 50-60, 50-70, 50-80, 50-90, 50-95, 50-100, 60-70, 60-80, 60-90, 60-95, 60-100, 70-80, 70-90, 70-95, 70-100, 80-90, 80-95, 80-100, 90-95, 90-100 or 95-100.

The position of the POI with respect to the DD, within the fusion protein to achieve optimal DD regulation. In some embodiments, the POI may be fused to the N terminus of the DD. In another embodiment, the POI may be fused to the C terminus of the DDs. In some embodiments, the fusion protein may include more than one POIs fused to one or more DDs.

Destabilizing Domains

As used herein, the term "destabilizing domains" (DDs), refers to protein domains that are unstable and degraded in the absence of ligand, but whose stability is rescued by binding to a high affinity cell-permeable ligand. Destabilizing domains (DDs) can be fused to a target protein of interest (POI) and can convey its destabilizing property to the protein of interest, causing protein degradation. The presence, absence or an amount of a small molecule ligand that binds to or interacts with the DD, can, upon such binding or interaction modulate the stability of the payload(s) and consequently the function of the payload. A protein domain with destabilizing property (e.g. a DD) is used in conjunction with a cell-permeable ligand to regulate any protein of interest when it is fused with the destabilizing domain. DDs render the attached protein of interest unstable in the absence of a DD-binding ligand such that the protein is rapidly degraded by the ubiquitin-proteasome system of the cell. However, when a specific small molecule ligand binds its intended DD as a ligand binding partner, the instability is reversed and protein function is restored. The conditional nature of DD stability allows a rapid and non-perturbing switch from stable protein to unstable substrate for degradation. Such a destabilization domain may or may not require the interaction of another protein for modulating stability of the POI. In some embodiments, the ligand regulated destabilizing domain merely requires exposure to a small molecule ligand, and does not require the formation of a ternary complex, as does the FKBP-rapamycin-FRB complex. An exemplary species is a "single-domain", ligand dependent destabilization domain, wherein the single polypeptide comprises only a single domain (i.e. folded structure or functional unit as determined by X-ray crystallography, protease digestion, and/or computer modeling).

Due to its reversibility, specificity and the fast and easy regulation on protein level, the post-transcriptional tuning system provides a useful system for gene regulation. Furthermore, the regulation may be dose-dependent, thereby altering the protein-turnover rate to transform a short-lived or no detectable protein into a protein that functions for a precisely controlled period of time (Iwamoto et al., *Chem. Biol.* 2010, 17: 981-988).

Candidate destabilizing domain sequence identified from protein domains of known wildtype proteins (as a template) may be mutated to generate libraries of mutants based on the template candidate domain sequence. Libraries of mutants may be generated by any methods known in the art including error prone polymerase chain reaction and nucleotide analog mutagenesis. Destabilizing domains identified using random mutagenesis may be used to identify structural properties of the candidate DDs that may be required for destabilization, which may then be used to further generate libraries of mutations using site directed mutagenesis.

Human PDE5A Derived DDs

In some embodiments, the DDs of the present compositions and systems are derived from human PDE5A (cGMP-specific phosphodiesterase type 5A) protein. PDE5A is a cGMP selective phosphodiesterase and a member of the cyclic nucleotide phosphodiesterase family. PDE5A specifically hydrolyzes cGMP to 5'GMP thereby regulating intracellular concentrations of cyclic nucleotides, a process that is important for smooth muscle relaxation in the cardiovascular system.

In some embodiments, the PDE5A derived destabilizing domains may be derived from variants, and/or isoforms of PDE5A. Three isoforms of PDE5A namely, PDE5A, Isoform 1, PDE5A Isoform 2, and PDE5A Isoform 3 have been identified. These isoforms differ at their N terminal regions, and have unique first exons followed by a common sequence of 823 amino acids. Accordingly, PDE5 derived DDs may be derived from PDE5A, Isoform 1 (SEQ ID NO. 1; encoded by the nucleotide sequence of SEQ ID NO. 2); PDE5A Isoform 2 (SEQ ID NO. 3; encoded by SEQ ID NO. 61 or nucleotides 113-2614 of the nucleotide sequence of SEQ ID NO. 4) and/or PDE5A Isoform 3 (SEQ ID NO. 5; encoded by SEQ ID NO. 62 or nucleotides 95-2566 of the nucleotide sequence of SEQ ID NO. 6).

All PDE5A isoforms contain a catalytic domain that is located near the C terminus of the protein and is relatively selective for cGMP as a substrate at physiological levels. The substrate binding site is also the binding site for several known PDE5 inhibitors such as Sildenafil, which have been utilized to treat cardiovascular diseases and erectile dysfunction. Towards the N terminus, 2 homologous GAF domains are located. One of the GAF domains, GAF-A contains a high affinity binding site for cGMP. Occupancy of this domain by cGMP is known to cause activation of the catalytic domain. Moreover, the affinity of this site for cGMP is increased by cGMP-dependent protein kinase-mediated phosphorylation of serine 92. In another embodiment, the PDE5A derived DD may comprise the catalytic domain of PDE5A, spanning from amino acid position 535 to position 860 of UniProt ID: O76074 (SEQ ID NO. 1), as represented in SEQ ID NO. 7 (encoded by SEQ ID NO. 8). In addition to the catalytic domain, PDE5A derived DDs may also comprise one or more GAF domains and/or the C terminal portion that extends beyond the catalytic domain. In one embodiment, the PDE5A derived DD may consist of amino acids from position 535 to position 875 of SEQ ID NO. 1. In another embodiment, the PDE5A derived DD may consist of amino acids from position 466 to 875 or position 420 to 875 of SEQ ID NO. 1.

The destabilization domains described herein may also include amino acid and nucleotide substitutions that do not affect stability, including conservative, non-conservative substitutions and or polymorphisms. In one embodiment, the PDE5A derived DD may contain a polymorphism at residue 589 of SEQ ID NO. 1, wherein the DD may comprise an arginine residue instead of a glutamine residue and is denoted as Q589R. Additional polymorphisms may include glycine to aspartate substitution at residue 36 of SEQ ID NO. 1, denoted as G36D, and valine to alanine substitution at position 93 of SEQ ID NO. 1, denoted as V93A. In some embodiments, the PDE5 DD may comprise all three polymorphisms, G36D, V93A, Q589R. These polymorphisms are represented in GenBank Accession Number AB527373.1 consisting of the amino acid sequence of SEQ ID NO. 9, (encoded by SEQ ID NO. 10), wherein the annotation of amino acid position and mutation in "G36D, V93A, Q589R" is with respect to SEQ ID NO. 1. The catalytic domain of PDE5A with the Q589R polymorphism is represented by the amino acid sequence of SEQ ID NO. 11, encoded by the nucleotide sequence of SEQ ID NO. 12. PDE5A derived DDs with Q589R polymorphism described herein may also include amino acids 535-875 of PDE5A with Q589R polymorphism with amino acid sequence of SEQ ID NO. 13 (encoded by SEQ ID NO. 63). In some embodiments the nucleotide sequence of "535-875 of PDE5A" may include a stop codon (by SEQ ID NO. 14). In some embodiments the PDE5A derived DDs may include amino acids 466-875 of PDE5A comprising the Q589R polymorphism, and with amino acid sequence of SEQ ID NO. 15 (encoded by SEQ ID NO. 64). In some embodiments, the nucleotide sequence of "466-875 of PDE5A" may include a stop codon (SEQ ID NO. 16). In some embodiments, the PDE5A derived DDs may comprise amino acids 420-875 of PDE5A comprising Q589R polymorphism and with amino acid sequence of SEQ ID NO. 17 (encoded by SEQ ID NO. 65). In some embodiments, the nucleotide sequence of "420-875 of PDE5A" may include a stop codon (SEQ ID NO. 18).

According to the methods described herein, the inventors of the present disclosure identified several human PDE5A derived destabilizing mutations by random mutagenesis of the catalytic domain of PDE5A. The destabilization of the mutants in the absence of the binding ligand, Sildenafil was tested. Table 1 provides the PDE5A derived destabilizing mutations. The position number of the mutated amino acids listed in Table 1 is relative to the full length human PDE5A of SEQ ID NO. 1. In some embodiments, any of the PDE5A derived DDs may include a methionine at position 1 of the amino acid sequence.

TABLE 1

PDE5 DDs

| PDE5A mutant | Clone NO. | Sequence | Amino Acid SEQ ID NO. | Nucleic Acid SEQ ID NO. |
|---|---|---|---|---|
| Methionine, 535-860 of PDE5A (Q589R, K633E, T712S, K852E, K795E) | — | MEETRELQSLAAAVVPSAQTLKITDFSFSDFELSDLET ALCTIRMFTDLNLVQNFRMKHEVLCRWILSVKKNYR KNVAYHNWRHAFNTAQCMFAALKAGEIQNKLTDLE ILALLIAALSHDLDHRGVNNSYIQRSEHPLAQLYCHSI MEHHHFDQCLMILNSPGNQILSGLSIEEYKTSLKIIKQ AILATDLALYIKRRGEFFELIRKNQFNLEDPHQKELFL AMLMTACDLSAITKPWPIQQRIAELVATEFFDQGDRE REELNIEPTDLMNREKKNKIPSMQVGFIDAICLQLYE ALTHVSEDCFPLLDGCRKNRQEWQALAEQQ | 19 | 36 |
| Methionine, 535-860 of PDE5A (E536G, Q589R, C839S) | — | MEGTRELQSLAAAVVPSAQTLKITDFSFSDFELSDLE TALCTIRMFTDLNLVQNFRMKHEVLCRWILSVKKNY RKNVAYHNWRHAFNTAQCMFAALKAGKIQNKLTD LEILALLIAALSHDLDHRGVNNSYIQRSEHPLAQLYC HSIMEHHHFDQCLMILNSPGNQILSGLSIEEYKTTLKII KQAILATDLALYIKRRGEFFELIRKNQFNLEDPHQKE LFLAMLMTACDLSAITKPWPIQQRIAELVATEFFDQG DRERKELNIEPTDLMNREKKNKIPSMQVGFIDAICLQ LYEALTHVSEDSFPLLDGCRKNRQKWQALAEQQ | 20 | 37 |

TABLE 1-continued

PDE5 DDs

| PDE5A mutant | Clone NO. | Sequence | Amino Acid SEQ ID NO. | Nucleic Acid SEQ ID NO. |
|---|---|---|---|---|
| Methionine, 535-860 of PDE5A (N587S, Q589R, K608E, N661S, D764V) | — | MEETRELQSLAAAVVPSAQTLKITDFSFSDFELSDLET ALCTIRMFTDLNLVQSFRMKHEVLCRWILSVKKNYR ENVAYHNWRHAFNTAQCMFAALKAGKIQNKLTDLE ILALLIAALSHDLDHRGVSNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACVLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 21 | 38 |
| Methionine, 535-860 of PDE5A (Q589R, L675P, F755L) | — | MEETRELQSLAAAVVPSAQTLKITDFSFSDFELSDLET ALCTIRMFTDLNLVQNFRMKHEVLCRWILSVKKNYR KNVAYHNWRHAFNTAQCMFAALKAGKIQNKLTDL EILALLIAALSHDLDHRGVNNSYIQRSEHPLAQPYCH SIMEHHHFDQCLMILNSPGNQILSGLSIEEYKTTLKIIK QAILATDLALYIKRRGEFFELIRKNQFNLEDPHQKELL LAMLMTACDLSAITKPWPIQQRIAELVATEFFDQGDR ERKELNIEPTDLMNREKKNKIPSMQVGFIDAICLQLY EALTHVSEDCFPLLDGCRKNRQKWQALAEQQ | 22 | 39 |
| 535-860 of PDE5A (Q589R, D687A, D764N, S815C) | #2 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQLYCHSI MEHHHFAQCLMILNSPGNQILSGLSIEEYKTTLKIIKQ AILATDLALYIKRRGEFFELIRKNQFNLEDPHQKELFL AMLMTACNLSAITKPWPIQQRIAELVATEFFDQGDRE RKELNIEPTDLMNREKKNKIPCMQVGFIDAICLQLYE ALTHVSEDCFPLLDGCRKNRQKWQALAEQQ | 23 | 40 |
| 535-860 of PDE5A (Q589R, Y676D, L738H) | #13 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQLDCHSI MEHHHFDQCLMILNSPGNQILSGLSIEEYKTTLKIIKQ AILATDLALYIKRRGEFFEHIRKNQFNLEDPHQKELFL AMLMTACDLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 24 | 41 |
| 535-860 of PDE5A (Q589R, K591E, N609H, D764V) | #28 | EETRELQSLAAAVVPSAQTLKITDFSFSDFELSDLETA LCTIRMFTDLNLVQNFRMEHEVLCRWILSVKKNYRK HVAYHNWRHAFNTAQCMFAALKAGKIQNKLTDLEI LALLIAALSHDLDHRGVNNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACVLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 25 | 42 |
| 535-860 of PDE5A (Q589R, D764G) | #40 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACGLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 26 | 43 |
| 535-860 of PDE5A (F561L, Q589R, K604E, D724N, L797F) | #41 | EETRELQSLAAAVVPSAQTLKITDFSLSDFELSDLETA LCTIRMFTDLNLVQNFRMKHEVLCRWILSVKENYRK NVAYHNWRHAFNTAQCMFAALKAGKIQNKLTDLEI LALLIAALSHDLDHRGVNNSYIQRSEHPLAQLYCHSI MEHHHFDQCLMILNSPGNQILSGLSIEEYKTTLKIIKQ AILATNLALYIKRRGEFFELIRKNQFNLEDPHQKELFL AMLMTACDLSAITKPWPIQQRIAELVATEFFDQGDRE RKEFNIEPTDLMNREKKNKIPSMQVGFIDAICLQLYE ALTHVSEDCFPLLDGCRKNRQKWQALAEQQ | 27 | 44 |

TABLE 1-continued

PDE5 DDs

| PDE5A mutant | Clone NO. | Sequence | Amino Acid SEQ ID NO. | Nucleic Acid SEQ ID NO. |
|---|---|---|---|---|
| 535-860 of PDE5A (E535D, K555R, F564S, Q589R, K630R, C677R, N742S, I799T, M816A) | #42 | DETRELQSLAAAVVPSAQTLRITDFSFSDSELSDLETA LCTIRMFTDLNLVQNFRMKHEVLCRWILSVKKNYRK NVAYHNWRHAFNTAQCMFAALRAGKIQNKLTDLEI LALLIAALSHDLDHRGVNNSYIQRSEHPLAQLYRHSI MEHHHFDQCLMILNSPGNQILSGLSIEEYKTTLKIIKQ AILATDLALYIKRRGEFFELIRKSQFNLEDPHQKELFL AMLMTACDLSAITKPWPIQQRIAELVATEFFDQGDRE RKELNTEPTDLMNREKKNKIPSAQVGFIDAICLQLYE ALTHVSEDCFPLLDGCRKNRQKWQALAEQQ | 28 | 45 |
| 535-860 of PDE5A (Q589R, N609H, Y676N, A762S) | #43 | EETRELQSLAAAVVPSAQTLKITDFSFSDFELSDLETA LCTIRMFTDLNLVQNFRMKHEVLCRWILSVKKNYRK HVAYHNWRHAFNTAQCMFAALKAGKIQNKLTDLEI LALLIAALSHDLDHRGVNNSYIQRSEHPLAQLNCHSI MEHHHFDQCLMILNSPGNQILSGLSIEEYKTTLKIIKQ AILATDLALYIKRRGEFFELIRKNQFNLEDPHQKELFL AMLMTSCDLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 29 | 46 |
| 535-860 of PDE5A (Q589R, N636S, D687A, D764N, S815C) | #69 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQSKLTDLEI LALLIAALSHDLDHRGVNNSYIQRSEHPLAQLYCHSI MEHHHFAQCLMILNSPGNQILSGLSIEEYKTTLKIIKQ AILATDLALYIKRRGEFFELIRKNQFNLEDPHQKELFL AMLMTACNLSAITKPWPIQQRIAELVATEFFDQGDRE RKELNIEPTDLMNREKKNKIPCMQVGFIDAICLQLYE ALTHVSEDCFPLLDGCRKNRQKWQALAEQQ | 30 | 47 |
| 535-860 of PDE5A (Q589R, I599V, T711A, F744L, L746S, L804P) | #19 | EETRELQSLAAAVVPSAQTLKITDFSFSDFELSDLETA LCTIRMFTDLNLVQNFRMKHEVLCRWVLSVKKNYR KNVAYHNWRHAFNTAQCMFAALKAGKIQNKLTDL EILALLIAALSHDLDHRGVNNSYIQRSEHPLAQLYCH SIMEHHHFDQCLMILNSPGNQILSGLSIEEYKATLKIIK QAILATDLALYIKRRGEFFELIRKNQLNSEDPHQKELF LAMLMTACDLSAITKPWPIQQRIAELVATEFFDQGDR ERKELNIEPTDPMNREKKNKIPSMQVGFIDAICLQLY EALTHVSEDCFPLLDGCRKNRQKWQALAEQQ | 31 | 48 |
| 535-860 of PDE5A (S560G, V585A, N587S, Q589R, K591E, S663P, F840S) | #35 | EETRELQSLAAAVVPSAQTLKITDFGFSDFELSDLETA LCTIRMFTDLNLAQSFRMEHEVLCRWILSVKKNYRK NVAYHNWRHAFNTAQCMFAALKAGKIQNKLTDLEI LALLIAALSHDLDHRGVNNPYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACDLSAITKPWPIQQRIAELVATEFFDQGDRE RKELNIEPTDLMNREKKNKIPSMQVGFIDAICLQLYE ALTHVSEDCSPLLDGCRKNRQKWQALAEQQ | 32 | 49 |
| 535-860 of PDE5A (Q589R, I648V, M816T) | #55 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLVAALSHDLDHRGVNNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACDLSAITKPWPIQQRIAELVATEFFDQGDRE RKELNIEPTDLMNREKKNKIPSTQVGFIDAICLQLYEA LTHVSEDCFPLLDGCRKNRQKWQALAEQQ | 33 | 50 |
| 535-860 of PDE5A (F561L, F564L, Q589R, D724N, S766F, T802P) | #8 | EETRELQSLAAAVVPSAQTLKITDFSLSDLELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQLYCHSI MEHHHFDQCLMILNSPGNQILSGLSIEEYKTTLKIIKQ AILATNLALYIKRRGEFFELIRKNQFNLEDPHQKELFL AMLMTACDLFAITKPWPIQQRIAELVATEFFDQGDRE RKELNIEPPDLMNREKKNKIPSMQVGFIDAICLQLYE ALTHVSEDCFPLLDGCRKNRQKWQALAEQQ | 34 | 51 |

TABLE 1-continued

PDE5 DDs

| PDE5A mutant | Clone NO. | Sequence | Amino Acid SEQ ID NO. | Nucleic Acid SEQ ID NO. |
|---|---|---|---|---|
| 535-860 of PDE5A (Q541R, F559L, Q589R, H678R, I824T) | #25 | EETRELRSLAAAVVPSAQTLKITDLSFSDFELSDLETA LCTIRMFTDLNLVQNFRMKHEVLCRWILSVKKNYRK NVAYHNWRHAFNTAQCMFAALKAGKIQNKLTDLEI LALLIAAL SHDLDHRGVNNSYIQRSEHPLAQLYCRSI MEHHHFDQCLMILNSPGNQILSGLSIEEYKTTLKIIKQ AILATDLALYIKRRGEFFELIRKNQFNLEDPHQKELFL AMLMTACDLSAITKPWPIQQRIAELVATEFFDQGDRE RKELNIEPTDLMNREKKNKIPSMQVGFIDATCLQLYE ALTHVSEDCFPLLDGCRKNRQKWQALAEQQ | 35 | 52 |
| 535-860 of PDE5A (Q589R, K633E, T712S, K852E, K795E) | #3 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGEIQNKLTDLEI LALLIAALSHDLDHRGVNNSYIQRSEHPLAQLYCHSI MEHHHFDQCLMILNSPGNQILSGLSIEEYKTSLKIIKQ AILATDLALYIKRRGEFFELIRKNQFNLEDPHQKELFL AMLMTACDLSAITKPWPIQQRIAELVATEFFDQGDRE REELNIEPTDLMNREKKNKIPSMQVGFIDAICLQLYE ALTHVSEDCFPLLDGCRKNRQEWQALAEQQ | 66 | 70 |
| 535-860 of PDE5A (E536G, Q589R, C839S) | #53 | EGTRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACDLSAITKPWPIQQRIAELVATEFFDQGDRE RKELNIEPTDLMNREKKNKIPSMQVGFIDAICLQLYE ALTHVSEDSFPLLDGCRKNRQKWQALAEQQ | 67 | 71 |
| 535-860 of PDE5A (N587S, Q589R, K608E, N661S, D764V) | #57 | EETRELQSLAAAVVPSAQTLKITDFSFSDFELSDLETA LCTIRMFTDLNLVQSFRMKHEVLCRWILSVKKNYRE NVAYHNWRHAFNTAQCMFAALKAGKIQNKLTDLEI LALLIAALSHDLDHRGVSNSYIQRSEHPLAQLYCHSI MEHHHFDQCLMILNSPGNQILSGLSIEEYKTTLKIIKQ AILATDLALYIKRRGEFFELIRKNQFNLEDPHQKELFL AMLMTACVLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 68 | 72 |
| 535-860 of PDE5A (Q589R, L675P, F755L) | #30 | EETRELQSLAAAVVPSAQTLKITDFSFSDFELSDLETA LCTIRMFTDLNLVQNFRMKHEVLCRWILSVKKNYRK NVAYHNWRHAFNTAQCMFAALKAGKIQNKLTDLEI LALLIAALSHDLDHRGVNNSYIQRSEHPLAQPYCHSI MEHHHFDQCLMILNSPGNQILSGLSIEEYKTTLKIIKQ AILATDLALYIKRRGEFFELIRKNQFNLEDPHQKELLL AMLMTACDLSAITKPWPIQQRIAELVATEFFDQGDRE RKELNIEPTDLMNREKKNKIPSMQVGFIDAICLQLYE ALTHVSEDCFPLLDGCRKNRQKWQALAEQQ | 69 | 73 |

In some embodiments, the DDs derived from PDE5A may comprise one, two, three, four, five or more mutations to the catalytic domain of PDE5A selected from E535D, E536G, Q541R, K555R, F559L, S560G, F561L, F564L, F564S, V585A, N587S, K591E, I599V, K604E, K608E, N609H, K630R, K633E, N636S, I648V, N661S, S663P, L675P, S766F, Y676D, Y676N, C677R, H678R, D687A, T711A, T712S, D724N, L738H, N742S, F744L, L746S, F755L, A762S, D764V, D764N, D764G, K795E, L797F, I799T, L804P, T802P, S815C, M816A, M816T, I824T, C839S, F840S, and K852E.

The amino acid sequences of the destabilizing domains, in some embodiments, have at least about 40%, 50 or 60% identity, further at least about 70% identity, preferably at least about 75% or 80% identity, more preferably at least about 85%, 86%, 87%, 88%, 89% or 90% identity, and further preferably at least about 91%, 92%, 93%, 94%, 95%, 96%, 97%, 98% or 99% identity to the amino acid sequence set forth therein. Percent identity may be determined, for example, by comparing sequence information using the advanced BLAST computer program, including version Magic-BLAST 1.2.0, available from the National Institutes of Health. The BLAST program is based on the alignment method discussed in Karl and Altschul (1990) *Proc. Natl. Acad. Sci USA,* 87:2264-68 (the contents of which are incorporated by reference in their entirety). Accordingly, PDE5A sequence of SEQ ID NO. 1 was analyzed using BLAST and sequences that demonstrated up to 40% homology were identified. This analysis identified Phosphodiesterase 11 isoform 1, Phosphodiesterase 11 isoform 2, Phosphodiesterase 11 isoform 3 and Phosphodiesterase 11 isoform 4 which bear approximately 40% homology to PDE5A. DDs may in some instances be derived from PDE11 isoforms.

In some embodiments, PDE5A derived destabilizing domains may be identified by the method of walk-through mutagenesis. The method of walk through mutagenesis consists of introducing a predetermined amino acid in to each position in a predefined region (or several different regions) of the amino acid sequence of a parent polypeptide. A PDE5A protein library is generated which contains multiple mutant PDE5A proteins, each having the predetermined amino acid in one or more positions in the region and collectively, in every position in the region. In some embodiments, predetermined regions selected for mutagenesis may include regions of PDE5A which are enriched for destabilizing mutations. In some embodiments, the predetermined region for mutagenesis may be selected from a portion of PDE5A of SEQ ID NO. 1, wherein the predetermined region spans from 531-541, position 555-564, position 587-591, position 604-609, position 630-636, position 674-678, position 762-766, position 795-797; a position 809-816 or any combination of thereof. This method allows for systematic evaluation of the role of a specific amino acid in the ligand dependent stabilization. Walk through mutagenesis methods are described in further detail in U.S. Pat. Nos. 6,649,340, 5,830,650, and 5,798,208 (the contents of which are incorporated by reference in their entirety).

Amino acid substitutions utilized for methods described herein may be conservative or non-conservative substitutions. Conservative amino acid substitutions may be made in the amino acid sequences described herein to obtain derivatives of the peptides that may advantageously be utilized. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having acidic side chains, such as aspartic acid and glutamic acid; amino acids having acidic side chains, including glutamine and asparagine; basic amino acids, including lysine, arginine and histidine; amino acids having aromatic ring side chains, including phenylalanine, tyrosine, and tryptophan; and amino acids having sulfur containing side chains, including cysteine and methionine. Additionally, amino acids having acidic side chains, such as aspartic acid and glutamic acid, can often be substituted with amino acids having amide side chains such as asparagine and glutamine.

The destabilizing domains may also be fragments of the above described destabilizing domains, including fragments containing variant amino acid sequences. Preferred fragments are unstable in the absence of a stabilizing ligand and stabilized by the presence of ligand. Such fragments are readily identified using assays described herein. Preferred fragments retain the ability to bind to a stabilizing ligand with similar efficiency to the destabilizing domains described herein or with at least 90% efficiency, or at least 80% efficiency, at least 70% or at least 50% efficiency with respect to the described destabilizing domains. Preferred destabilizing domains may be fused at the N terminus or C terminus of a POI.

Ligands

Stabilizing ligands for use include Sildenafil (i.e. 5-[2-ethoxy-5-(4-methylpiperazin-1-yl) sulfonylphenyl]1-1-methyl-3-propyl-4H-pyrazolo[4,3-d] pyrimidin-7-one), a commercially available PDE5A inhibitor. In some embodiments, ligands known to bind to full length or a portion of PDE5A may be utilized as stabilizing ligands. For example, stabilizing ligands may include but are not limited to known PDE5A inhibitors, including Vardenafil, Tadalafil, Avanafil, Lodenafil, Mirodenafil, Udenafil, Benzamidenafil, Dasantafil, and Beminafil. Other stabilizing ligands that may be useful include Sildenafil-derived ligands containing portions of the ligand known to mediate binding to PDE5A. Ligands may also be modified to reduce off-target binding to Phosphodiesterases and increase specific binding to PDE5A. Stabilizing ligands may also be selected through the analysis of the dependence of the stabilizing capability of the ligand on its chemical structure, through Structure Activity Relationships (SAR) studies. Any of the methods related to SAR, known in art may be utilized to identify stabilizing ligands.

Proteins of Interest

In some embodiments, proteins of interest may be a natural protein in an organism genome, or variants, mutants, derivatives thereof. The natural protein may be from, for example, a mammalian organism, a bacterium, and a virus. In one example, the protein of interest, or a polypeptide may be derived from human genome.

In some embodiments, the proteins of interest may be selected from, but are not limited to enzymes, structural proteins, signaling proteins, regulatory proteins, transport or carrier proteins, sensory proteins, motor proteins, immune proteins, and storage proteins.

Proteins of interest may also be selected from any known reporter protein, which refers to any protein capable of creating a detectable signal, in response to an input. Examples include alkaline phosphatase, β-galactosidase, chloramphenicol acetyltransferase, β-glucuronidase, peroxidase, (β-lactamase, catalytic antibodies, bioluminescent proteins e.g. luciferase, and fluorescent proteins such as Green fluorescent protein (GFP).

III. Methods, Cells and Transduced Animals

Also disclosed is method for conditionally stabilizing a protein of interest, which consists of fusing a nucleic acid encoding the protein of interest fused in-frame to a nucleic acid encoding a destabilizing domain, optionally in combination with one or more of the substitutions identified herein. In one example, the cells are transfected with nucleic acids encoding a fusion protein comprising a protein of interest fused in frame to a variant PDE5A protein. Expression of the DD fusion protein may be driven by the endogenous promoter, ideally reproducing the spatial and temporal expression patterns of the unmodified gene.

The cells may be transfected, e.g. using an expression vector or transduced (i.e. infected) using a viral vector, including, but not limited to a vector derived from a retrovirus (e.g. a lentivirus), herpesvirus, pox virus, adenovirus, adeno-associated virus, or an RNA virus, such as poliovirus, flavivirus, alphavirus or the like. The exemplary viral vector is a retrovirus.

The cells may be eukaryotic cells, including but not limited to cells from humans, primates, rodents, and other animals, including domesticated animals. The cells may also be from plants, insects, amphibians, and apicomplexan parasites. The cells may be in culture or in a living organism. The wild-type or naturally occurring gene or allele encoding the POI may be deleted to facilitate study of the conditionally stabilized POI.

The present methods and compositions also allow the creation of transgenic animals harboring engineered alleles that direct the expression of a ligand stabilized POI. Expression of the DD fusion protein may be driven by the endogenous promoter ideally reproducing the spatial and temporal expression patterns of the unmodified gene. The ligand may be administered regularly from an early age (including in utero) to stabilize the fusion protein until the mice achieve a specified age, at which time, withdrawal of the ligand results in a rapid degradation of the fusion protein. Unlike Cre-mediated gene disruption, this method is reversible, such that simply reinitiating the administration of the ligand, allows the rapid, reversible and conditional control of protein function in a complex system.

The ability to specifically and conditionally stabilize a POI in a cell will enable the study of many proteins to determine their biological function and importance in a cell. The present methods and compositions represent a significant improvement over current methods of conditional protein regulation.

IV. Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Conservative amino acid substitutions: As used herein, a "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of glutamine for aspartate is considered a conservative substitution since both are similarly-sized negatively-charged amino acids. Groupings of amino acids by physico-chemical properties are known to those of skill in the art.

Domain: As used herein, the terms "domain" and "region" are used interchangeably herein and refer to a contiguous sequence of amino acids within a POI or destabilizing domain, typically characterized by being either conserved or variable and having a defined function, such as ligand binding, conferring stability or instability, enzymatic function, etc.

Degradation: As used herein, "degradation" or "destruction" of a protein means its hydrolysis into smaller proteins or amino acids, such as by the cellular proteasome.

Destabilized: As used herein, the term "destable," "destabilize," "destabilizing region" or "destabilizing domain" means a region or molecule that is less stable than a starting, reference, wild-type or native form of the same region or molecule.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Fused: As used herein, "fused" means arranged in-frame as part of the same contiguous sequence of amino acids in a polypeptide. Fusion can be direct such that there are no additional amino acid residues or via a linker to improve performance or add functionality.

Homologous: Two amino acid sequences or two nucleotide sequences are considered "homologous" if they have an alignment score of >5 (in standard deviation units) using the program ALIGN with the mutation gap matrix and a gap penalty of 6 or greater (Dayhoff, M. O., in Atlas of Protein Sequence and Structure (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, 70%, 80%, 90%, 95%, or even 98% identical when optimally aligned using the ALIGN program mentioned above.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Introduction of nucleic to cells: As used herein, "introduction of nucleic to cells" means transfection, transduction (infection), or transformation of nucleic acids (e.g., DNA) into cells, such that the nucleic acids may be used by the cell to express a protein of interest.

Modulate: "Modulate" intends a lessening, an increase, or some other measurable change, e.g., in the stability or biological function of a protein.

Mutant: As used herein, a "mutant" is a mutated protein designed or engineered to alter properties or functions relating to protein stabilization and/or ligand binding.

Protein of interest (POI): As used herein, a "protein of interest" or "POI" is any protein, or functional fragment or derivative, thereof, that one skilled in the art wishes to study.

Preferentially binds: As used herein, "preferentially binds" means to bind with greater efficiency to a subject molecule (such as a particular amino acid sequence) than another molecule. The difference in binding efficiency may be 5-fold, 10-fold, 50-fold, 100-fold, 500-fold, 1,000-fold, 10,000-fold, or more.

PDE5A variant: "PDE5A variant" refers to a protein wherein one or more amino acid residues, are substituted for an amino acid other than the amino acid in the PDE5A (SEQ ID NO. 1). Other amino acid positions that can be substituted are indicated in the Tables and Figures.

Protein: As used herein, the terms "protein" and "polypeptide" are used interchangeably and without distinction to refer to a compound made up of a chain of amino acid residues linked by peptide bonds. Unless otherwise indicated, the sequence for peptides is given in the order from the "N" (or amino) terminus to the "C" (or carboxyl) terminus. It is understood that polypeptides include a contiguous sequence of amino acid residues.

Peptide: A peptide or peptide fragment is "derived from" a parent peptide or polypeptide if it has an amino acid sequence that is homologous to, but not identical to, the parent peptide or polypeptide, or of a conserved fragment from the parent peptide or polypeptide.

Small molecule ligand: A "small molecule ligand" is a discrete small-molecule, well known in the pharmaceutical and material sciences, which is to be distinguished from, e.g., a polypeptide or nucleic acids, which is a polymer consisting of monomeric subunits. Small molecule ligands may be naturally-occurring or synthetic as exemplified by pharmaceutical products, laboratory reagents, and the like.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a secondary status or state or to a reference compound or entity.

Variant: As used herein, a "variant" protein is a protein having an amino acid sequence that does not occur in nature, as exemplified by sequences in GenBank.

V. Kits of Parts

The methods and compositions described herein may be packaged together with instructions for use, as in a kit of parts. Preferred kits of parts include a PDE5A variant, a stabilizing ligand, and instructions for use. The PDE5A variant may include a substitution described herein, or may include other substitutions identified using the methods decried herein. The stabilizing ligand may be as described herein or a variant or derivative that functions in a similar manner. Instructions may include the nucleotide sequences of a plasmid encoding a PDE5A variant and instructions and guidelines for inserting (i.e. cloning) a POI into the plasmid-in frame with the PDE5A variant. The instructions may also include dosing recommendations and hardware such as syringes, to deliver the fusion protein to an organism or to cells.

EXAMPLES

Example 1

PDE5A Library Generation

Diversity in the PDE5A catalytic domain sequence (Q589R) (SEQ ID NO. 11) was generated using a combination of error-prone PCR and nucleotide analog mutagenesis. Primers for mutagenic PCR were designed to anneal upstream of the 5' restriction site to be used for cloning the mutagenesis products into pBMN iHcRed-tandem retroviral expression vector and to anneal downstream of the 3' restriction site. Three independent conditions were used to generate diversity. Condition set A utilized 4 ng template, 0.5 µM of each oligonucleotide primer, 5 units Taq polymerase, 5 mM $MgCl_2$, 0.2 mM $MnCl_2$, 0.4 mM dNTPs in equal ratio, and an excess of 0.2 mM dATP and dCTP. Condition set B was identical to A, except that dGTP and dTTP were present in excess. Condition set C utilized the non-natural nucleotides 8-oxo-dGTP and dPTP to encourage nucleotide mis-incorporation. The PDE5A libraries were pooled and ligated into the pBMN iHcRed-t retroviral expression vector, affording a library containing approximately $3 \times 10^4$ members.

Example 2

Cell Culture and Transduction

The NIH3T3 cell line was cultured in DMEM supplemented with 10% heat-inactivated donor bovine serum (Invitrogen), 2 mM glutamine, 100 U/ml penicillin and 100 µg/ml streptomycin.

The ΦNX ecotropic packaging cell line was transfected using standard Lipofectamine 2000 protocols. Viral supernatants were harvested 48 hours, post transfection, filtered and concentrated 10-fold using Amicon Ultra centrifugal filter device with a 100kDa cutoff. NIH 3T3 cells were incubated with concentrated retroviral supernatants supplemented with 4 µg/ml polybrene for 4 hours at 37° C. Cells were washed once with PBS and cultured in growth media for 24-36 hours to allow for viral integration.

Example 3

Fluorescence-Activated Cell Sorting (FACS)

The transduced NIH3T3 cells were subjected to analysis using fluorescence-activated cell sorting (FACS) to screen the libraries of PDE5A mutants. 24 hours prior to analysis, transduced NIH3T3 cells were plated at $1 \times 10^5$ cells per well of a 12-well plate. Cells were removed from the plate using PBS and 2 mM EDTA, washed once with PBS, and resuspended in 200 µL, PBS. FACS analysis was performed on instruments at the Stanford Shared FACS Facility with 10,000 events represented.

Example 4

Cell-Based Screening Assay

To identify destabilizing domains that are responsive to the PDE5A ligand, Sildenafil, a cell-based screening assay was employed in which the fluorescence of green fluorescent protein derived from *Aequorea coerulescens* (AcGFP) served as an indicator of PDE5A stability. A library based on the PDE5A catalytic domain sequences was generated using error prone PCR and then cloned in-frame in front of AcGFP. A Moloney murine leukemia retroviral expression was used to stably integrate this library of PDE5A-AcGFP fusions into NIH-3T3 fibroblasts, and the transduced cells were subjected to three rounds of sorting using flow cytometry. In the first round, cells were treated with 10 µM of PDE5A ligand, Sildenafil for 16-24 before analysis. Fluorescent cells were collected and further cultured in the absence of ligand for 60 hours. Analysis revealed that approximately 5% of the cell population exhibited decreased fluorescence levels indicating that most the sequences were either unmutated or contained mutations that did affect the stability of the fusion protein. This small population of cells exhibiting decreased fluorescence was collected and cultured once more in the presence of 10 µM Sildenafil for 24 hours, at which time AcGFP-expressing cells were collected and the genomic DNA was isolated.

Example 5

Identification of C-Terminal PDE5A-Derived Destabilizing Domains

A library of AcGFP-PDE5A fusions i.e., C-terminal PDE5A mutants was screened using the cell-based screening assay described previously to identify C-terminal destabilizing domains. Several clones that exhibited desired characteristics, i.e., low basal expression in the absence of ligand and high expression in the presence of ligand were selected that. Identified candidates were subjected to further characterization by FACS. Cells were split into two treatment groups and incubated with either Sildenafil (10 μM) or vehicle alone for 24 hours. Cells that were mock transduced or transduced with the wild-type PDE5A construct were also included in the analysis. The stabilization ratio was calculated as the fold change in GFP intensity of the AcGFP-PDE5A construct in Sildenafil treated sample compared to vehicle alone treated sample. The results are presented in Table 2 where the C terminal PDE5A mutants are denoted as PDE5AC. Among the identified mutants, PDE5AC (#2) and PDE5AC (#41) showed stabilization ratios greater than 6 suggesting strong ligand dependent stabilization.

TABLE 2

FACS analysis of C-terminal PDE5A mutants

| Clone No. | Sildenafil (10 μM) | Mean Fluorescence intensity | Stabilization ratio |
|---|---|---|---|
| NIH3T3 control | − | 345 | — |
| PDE5AC Wild-type | − | 9520 | 0.9 |
|  | + | 8797 |  |
| PDE5AC (#2) | − | 1023 | 6.5 |
|  | + | 6577 |  |
| PDE5AC (#8) | − | 1066 | 3.1 |
|  | + | 3310 |  |
| PDE5AC (#13) | − | 1076 | 5.8 |
|  | + | 6284 |  |
| PDE5AC (#25) | − | 1452 | 1.6 |
|  | + | 2340 |  |
| PDE5AC (#28) | − | 1382 | 4.4 |
|  | + | 6055 |  |
| PDE5AC (#40) | − | 1255 | 4.7 |
|  | + | 5923 |  |
| PDE5AC (#41) | − | 1000 | 6.1 |
|  | + | 6115 |  |
| PDE5AC (#42) | − | 1658 | 3.5 |
|  | + | 5861 |  |
| PDE5AC (#43) | − | 1017 | 5.4 |
|  | + | 5518 |  |
| PDE5AC (#69) | − | 1126 | 5.6 |
|  | + | 6365 |  |

Figure 2:
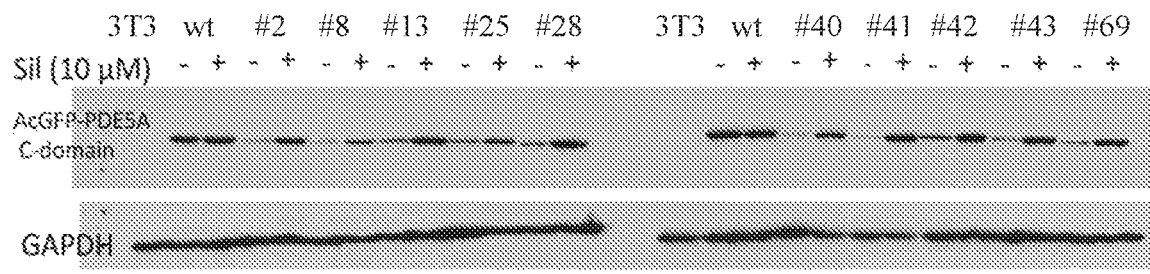
FIG. 2 is a western blot depicting the ligand dependent stabilization of PDE5A, C terminal fusion proteins.

Identified PDE5A mutants were further validated using immunoblot analysis. NIH3T3 cells expressing AcGFP-PDE5A fusions were incubated with 10 μM Sildenafil or vehicle alone for 24 hours and the stability of PDE5A mutants was evaluated at the protein level. Cell lysates obtained from transduced NIH3T3 cells were immunoblotted using the anti-XFP antibody (1:3000) at 4° C. overnight. Samples were also immunoblotted with anti-GAPDH antibody (1:10000) to ensure uniform protein loading. Samples were then incubated with secondary anti-mouse antibody (1:3000) at room temperature for 1 hour, followed by visualization using appropriate methods. Immunoblot results are presented in FIG. 2. All PDE5A mutants demonstrated enhanced GFP expression in the presence of the ligand. The difference in band intensity recapitulates the pattern from the FACS analysis. Consistent with the FACS analysis, PDE5AC (#2) and PDE5AC (#41) displayed most drastic difference in the intensity of the bands from mock treated sample and Sildenafil treated sample, indicating strong ligand dependent stabilizing effect.

Identified PDE5A mutants were sequenced and sequences were compared to the wild-type sequence of human PDE5A catalytic domain to identify mutations. The mutations identified are shown in Table 3 where the C terminal PDE5A mutants are denoted as PDE5AC. The number of amino acid mutations was calculated based on the wildtype PDE5A amino acid sequence of SEQ ID NO. 1.

TABLE 3

Sequence analysis of C-terminal PDE5A mutants

| Clone No. | No. of amino acid mutations | Amino acid mutations | Protein SEQ ID NO. |
|---|---|---|---|
| PDE5AC (#2) | 4 | Q589R, D687A, D764N, S815C | 23 |
| PDE5AC (#13) | 3 | Q589R, Y676D, L738H | 24 |
| PDE5AC (#28) | 4 | Q589R, K591E, N609H, D764V | 25 |
| PDE5AC (#40) | 2 | Q589R, D764G | 26 |
| PDE5AC (#41) | 5 | F561L, Q589R, K604E, D724N, L797F | 27 |
| PDE5AC (#42) | 9 | E535D, K555R, F564S, Q589R, K630R, C677R, N742S, I799T, M816A | 28 |
| PDE5AC (#43) | 4 | Q589R, N609H, Y676N, A762S | 29 |
| PDE5AC (#69) | 5 | Q589R, N636S, D687A, D764N, S815C | 30 |
| PDE5AC (#8) | 5 | F561L, F564L, Q589R, D724N, S766F, T802P | 34 |
| PDE5AC (#25) | 5 | Q541R, F559L, Q589R, H678R, I824T | 35 |

Sequence analysis (see Table 3) revealed that residue D764 as a frequently mutated residue. D764G alone in Clone 40 induced 4.7-fold of ligand dependent stabilization, suggesting that it may be important for PDE5A protein stability. The error prone mutagenesis also introduced several silent mutations which was evident by the analysis of the nucleotide sequence.

Example 6

Optimization of C-Terminal PDE5A Mutants

Identified C-terminal PDE5A mutants were further optimized to improve ligand dependent stabilization properties. Additional point mutations or linker sequences were evaluated for their effect on PDE5A mutant characteristics.

D764 Mutation

Residue D764 was identified as a mutational hotspot from sequence analysis. PDE5AC (#41) was engineered with either D764N or D764G mutation via site-directed mutagenesis. PDE5AC (#41) +D764N comprises the amino acid sequence of SEQ ID NO. 53 (encoded by SEQ ID NO. 54) and PDE5AC (#41) +D764G comprises the amino acid sequence of SEQ ID NO. 55 (encoded by SEQ ID NO. 56). AcGFP-PDE5A variants were evaluated for Sildenafil dependent stabilization via FACS as described previously. Results from FACS analysis are presented in Table 4 where the C terminal PDE5A mutants are denoted as PDE5AC. The stabilization ratio was calculated as the fold change in GFP intensity of the AcGFP-PDE5A construct in Sildenafil treated sample compared to vehicle alone treated sample.

TABLE 4

Effect of D764 mutations

| Clone No. | Sildenafil (10 μM) | Mean Fluorescence intensity | Stabilization ratio |
|---|---|---|---|
| NIH3T3 control | − | 303 | — |
| Wild-type | − | 6992 | 1.0 |
|  | + | 7093 |  |
| PDE5AC (#2) | − | 671 | 5.2 |
|  | + | 3483 |  |
| PDE5AC (#40) | − | 917 | 4.6 |
|  | + | 4229 |  |
| PDE5AC (#41) | − | 734 | 6.3 |
|  | + | 4647 |  |
| PDE5AC (#41) + D764G | − | 709 | 1.0 |
|  | + | 730 |  |
| PDE5AC (#41) + D764N | − | 684 | 1.5 |
|  | + | 1007 |  |

The results in Table 4, show that addition of D764G or D764N to PDE5AC (#41) did not improve its ligand dependent stabilization but rather abolished its responsiveness to Sildenafil as indicated by a reduction in the stabilization ration upon addition of ligand. These data show that effect of the mutations at the D764 position is dependent on the context of other mutations present on PDE5A. The combination of mutations in PDE5AC (#41), requires further optimization.

Protein Tags

Figure 3:
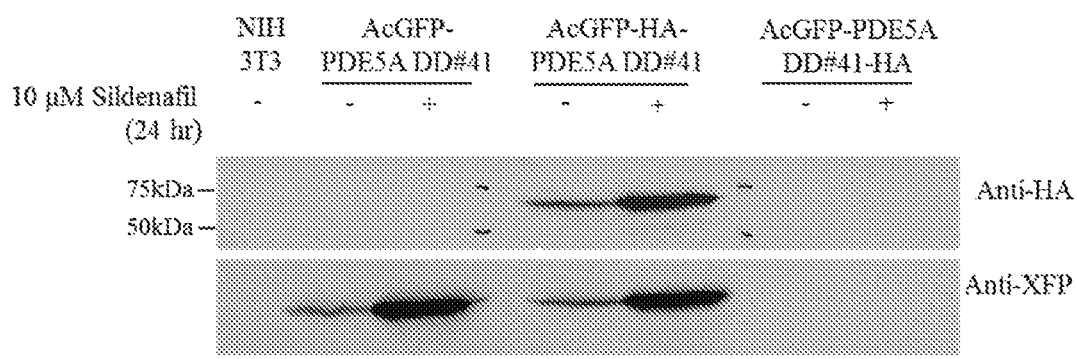
FIG. 3 is a western blot depicting the effect of HA tag on the stability of PDE5A mutants.

A hemagglutinin (HA) sequence (SEQ ID NO. 74; encoded by SEQ ID NO. 75) was cloned in-frame at either the 5'- or 3'-ends of the PDE5A mutant sequence from PDE5AC (#41). The construct further included AcGFP (amino acids 1-239 of WT) at the N terminus (SEQ ID NO. 76, encoded by SEQ ID NO. 77) and an EF linker/EcoRI restriction site (GAATTC). The resulting fusion protein adopts either the AcGFP (1-239 of WT)-EF linker-HA-PDE5AC-stop (#41) configuration with an amino acid sequence of SEQ ID NO. 57 (encoded by SEQ ID NO. 58) or AcGFP-EF-Linker-PDE5AC (#41)-HA-stop configuration with an amino acid sequence of SEQ ID NO. 59 (encoded by SEQ ID NO. 60). The effect of the HA sequence on ligand dependent stabilization was evaluated via immunoblot analysis. The transduced NIH3T3 cells were incubated with 10 μM Sildenafil or vehicle alone for 24 hours. Cell lysates obtained from transduced NIH3T3 cells were immunoblotted using either the anti-XFP antibody (1:3000) or anti-HA antibody (1:2000). As show in FIG. 3, HA-tagged fusion protein expression detected with either anti-XFP antibody or anti-HA antibody was nearly identical. AcGFP-HA-PDE5A (#41) exhibited similar level of ligand dependent stabilization compared to Clone 41. However, no protein expression was detected from AcGFP-PDE5A (#41)-HA in either Sildenafil treated sample or mock treated sample. Additional protein tag sequences may be explored to be used in conjunction with destabilizing domains.

Example 7

Evaluation of Extended PDE5A Variants

Extended versions of human PDE5A that included residues in addition to catalytic domain (residues 535-860 of SEQ ID NO. 1) with Q589R polymorphism (SEQ ID NO. 11) were evaluated for use as C-terminal destabilizing domains. Three extended PDE5A sequences were tested that consisted of residues 535-875 of SEQ ID NO. 1 with Q589R polymorphism (SEQ ID NO. 13); residues 466-875 of SEQ ID NO. 1 with Q589R polymorphism (SEQ ID NO. 15); or residues 420-875 of SEQ ID NO. 1 with Q589R polymorphism (SEQ ID NO. 17). These PDE5A sequences were cloned to the 3' end of AcGFP and the AcGFP fusions were assessed for ligand dependent stabilization using FACS as described previously. Results of FACS analysis are presented in Table 5 where the C terminal PDE5A mutants are denoted as PDE5AC. The stabilization ratio was calculated as the fold change in GFP intensity of the AcGFP-PDE5A construct in Sildenafil treated sample compared to vehicle alone treated sample.

TABLE 5

FACS analysis of extended PDE5A variants

| Construct | Sildenafil (10 μM) | Mean Fluorescence intensity | Stabilization ratio |
|---|---|---|---|
| NIH3T3 control | − | 409 | — |
| PDE5AC 535-860 (Q589R) | − | 8431 | 1.0 |
|  | + | 8557 |  |
| PDE5AC 535-875 (Q589R) | − | 6761 | 1.0 |
|  | + | 6462 |  |
| PDE5AC 466-875 (Q589R) | − | 819 | 1.1 |
|  | + | 888 |  |
| PDE5AC 420-875 (Q589R) | − | 620 | 0.9 |
|  | + | 572 |  |

The extended PDE5A variants displayed reduced stability in the absence of Sildenafil compared to the PDE5A catalytic domain (535-860) (Q589R). The reduction was most substantial in PDE5AC 466-875 (Q589R) and PDE5AC 420-875 (Q589R). However, none of the extended PDE5A variants showed ligand responsive stabilization in the presence of Sildenafil. Further, PDE5AC (466-875) (Q589R) and PDE5AC (420-875) (Q589R) showed low basal expression in the absence of ligand while PDE5AC (535-860) (Q589R) and PDE5AC (535-875) (Q589R) showed high basal expression in the absence of ligand. These data show that PDE5AC (535-860) (Q589R) and PDE5AC (535-875) (Q589R) may be suitable for screening and identification of mutations that destabilize PDE5AC since they have high basal expression. This analysis may be utilized in combination with the mutagenesis analysis to identify additional destabilizing domains.

Example 8

Sildenafil Dose Dependency

Figure 4A:
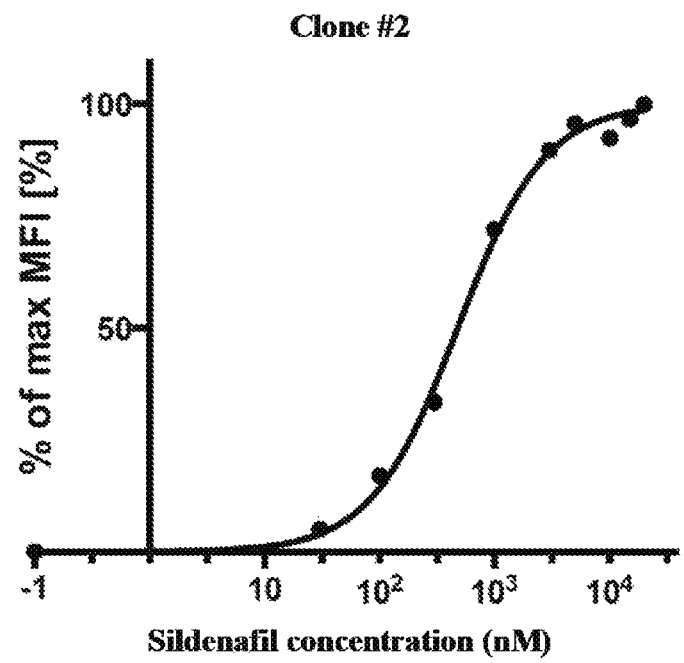
FIG. 4A and FIG. 4B show Sildenafil dose dependent stabilization of PDE5A mutants.
Figure 4B:
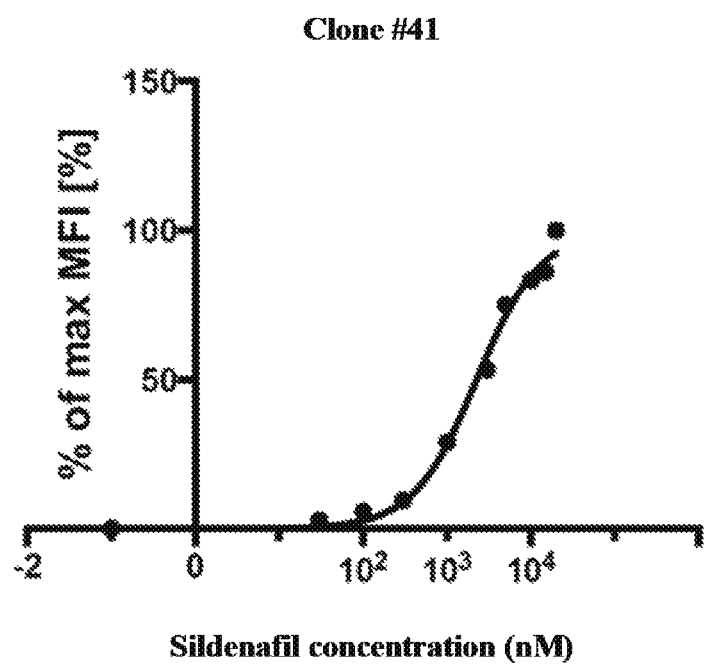

NIH3T3 cells expressing AcGFP-PDE5A variants were incubated with varying concentrations of Sildenafil ranging from 0.003 μM to 30 μM. The stability of PDE5A mutants was measured using FACS and mean fluorescence intensity (MFI) of GFP was calculated. Maximum MFI was observed at highest Sildenafil concentration. Percentage of max MFI (%) was calculated as the ratio of the MFI at a ligand concentration compared to the maximum MFI. Percentage of max MFI was plotted against the concentration of Sildenafil presented in a log scale. Titration curves of PDE5AC (#2) and PDE5AC (#41) are presented in FIG. 4A and FIG. 4B, respectively. Both clones showed an increase in percentage of max MFI with increasing doses of Sildenafil, indicating a ligand dose-dependent stabilization of PDE5A mutants. The half maximal effective concentration or $EC_{50}$ was approximately 0.5 μM for PDE5AC (#2) and 2 μM for PDE5AC (#41).

Example 9

Identification of N-Terminal PDE5A-Derived Destabilizing Domains

A library of PDE5A-AcGFP fusions i.e., N-terminal PDE5A mutants, was screened using the cell-based screening assay described previously to identify N-terminal destabilizing domains. Several clones were selected that exhibited desired characteristics, i.e., low basal expression in the absence of ligand and high expression in the presence of ligand. Identified candidates were subjected to further characterization by FACS. Cells were split into two treatment groups and incubated with either Sildenafil (20 µM) or vehicle alone for 24 hours. Cells that were mock transduced or transduced with the wild-type PDE5A construct were also included in the analysis. The results are presented in Table 6 where the N terminal PDE5A mutants are denoted as PDE5AN. The stabilization ratio was calculated as the fold change in GFP intensity of the PDE5A-AcGFP construct in Sildenafil treated sample compared to vehicle alone treated sample.

TABLE 6

FACS analysis of N-terminal PDE5A mutants

| | Mean Fluorescence Intensity (MFI) | | |
|---|---|---|---|
| Construct | Vehicle control | Sildenafil (20 µM) | Stabilization Ratio |
| 3T3 | 234 | — | — |
| PDE5AN (#51) | 1603 | 1543 | 0.96 |
| PDE5AN (#64) | 991 | 966 | 0.97 |
| PDE5AN (#52) | 224 | 219 | 0.98 |
| PDE5AN (#36) | 230 | 230 | 1.00 |
| PDE5AN (#56) | 1052 | 1054 | 1.00 |
| PDE5AN (#4) | 213 | 218 | 1.02 |
| PDE5AN (#46) | 217 | 227 | 1.05 |
| PDE5AN (#28) | 468 | 501 | 1.07 |
| PDE5AN (#61) | 219 | 235 | 1.07 |
| PDE5AN (#42) | 223 | 240 | 1.08 |
| PDE5AN (#62) | 210 | 227 | 1.08 |
| PDE5AN (#17) | 204 | 224 | 1.10 |
| PDE5AN (#10) | 1157 | 1279 | 1.11 |
| PDE5AN (#14) | 206 | 228 | 1.11 |
| PDE5AN (#32) | 933 | 1074 | 1.15 |
| PDE5AN (#43) | 3407 | 4372 | 1.28 |
| PDE5AN (#18) | 3199 | 4523 | 1.41 |
| PDE5AN (#24) | 1603 | 2290 | 1.43 |
| PDE5AN (#59) | 535 | 1051 | 1.96 |
| PDE5AN (#41) | 920 | 1877 | 2.04 |
| PDE5AN (#9) | 1007 | 2215 | 2.20 |
| PDE5AN (#50) | 960 | 2113 | 2.20 |
| PDE5AN (#1) | 1488 | 3508 | 2.36 |
| PDE5AN (#35) | 1476 | 3684 | 2.50 |
| PDE5AN (#11) | 1143 | 2875 | 2.52 |
| PDE5AN (#53) | 1697 | 4440 | 2.62 |
| PDE5AN (#19) | 1502 | 4297 | 2.86 |
| PDE5AN (#55) | 1257 | 3602 | 2.87 |
| PDE5AN (#26) | 712 | 2633 | 3.70 |
| PDE5AN (#3) | 839 | 3335 | 3.97 |
| PDE5AN (#30) | 1056 | 4713 | 4.46 |
| PDE5AN (#57) | 770 | 5851 | 7.60 |

Among the analyzed mutants, PDE5AN (#57) exhibited highest stabilization ration of 7.6 indicating a strong stabilization as a result of low GFP intensity in the absence of ligand and high GFP intensity in the presence of ligand. A stabilization ratio greater than 1 was observed with all constructs except PDE5AN (#51), PDE5AN (#64), PDE5AN (#52), PDE5AN (#36), and PDE5AN (#56) indicating some level of ligand induced stabilization. Select PDE5A mutants were sequenced and sequences were compared to the wild-type sequence of human PDE5A catalytic domain to identify mutations. Sequence analysis (see Table 7) reveals point mutations different from those in the C-terminal mutants. Interestingly, a D764V mutation also was identified in PDE5AN (#57), highlighting its role in PDE5A structural stability. The number of amino acid mutations in Table 7 was calculated based on the wildtype PDE5A amino acid sequence of SEQ ID NO. 1.

TABLE 7

Sequence analysis of N-terminal PDE5A mutants

| Clone No. | No. of amino acid mutations | Amino acid mutations | Protein SEQ ID NO. |
|---|---|---|---|
| PDE5AN (#3) | 5 | Q589R, K633E, T712S, K852E, K795E | 66 |
| PDE5AN (#53) | 3 | E536G, Q589R, C839S | 67 |
| PDE5AN (#57) | 5 | N587S, Q589R, K608E, N661S, D764V | 68 |
| PDE5AN (#30) | 3 | Q589R, L675F, F755L | 69 |
| PDE5AN (#19) | 6 | Q589R, I599V, T711A, F744L, L746S, L804P | 31 |
| PDE5AN (#35) | 7 | S560G, V585A, N587S, Q589R, K591E, S663P, F840S | 32 |
| PDE5AN (#55) | 3 | Q589R, I648V, M816T | 33 |

Example 10

Comparison of N-Terminal and C-Terminal PDE5A-Derived Destabilizing Domains

The ability of PDE5A derived DDs to destabilize a protein of interest may depend on the position whether the DD is appended to the N terminus or the C terminus of the protein of interest. Mutant #2, and mutant #41 were appended either to the N terminus or C terminus of AcGFP and analyzed using the cell-based screening assay described previously to identify destabilizing domains. Cells were split into two treatment groups and incubated with either Sildenafil (10 µM) or vehicle alone for 24 hours. Cells that were mock transduced or transduced with the N terminal fused wild-type PDE5A or PDE5AN (#40) constructs were also included in the analysis. The results are presented in Table 8 where the C terminal PDE5A mutants are denoted as PDE5AC and N terminal PDE5A mutants are denoted as PDE5AN.

TABLE 8

N-terminal Vs. C-terminal PDE5A derived DD

| | Mean FITC-A | |
|---|---|---|
| Construct | DMSO | Sildenafil (10 µM) |
| 3T3 Parental cells | 571 | — |
| PDE5AN (#2) | 1271 | 2298 |
| PDE5AC (#2) | 1342 | 5030 |
| PDE5AN (#41) | 1284 | 1473 |
| PDE5AC (#41) | 1443 | 4620 |
| PDE5AN (WT) | 7519 | 8012 |
| PDE5AN (#40) | 1438 | 1949 |

The stabilization ratio was calculated as the fold change in GFP intensity of the AcGFP-PDE5A construct in Sildenafil treated sample compared to vehicle alone treated sample. The ratios are presented in Table 9.

TABLE 9

PDE5 DD comparative analysis

| | Stabilization Ratio | |
|---|---|---|
| Construct | N terminus fusion | C terminus fusion |
| #2 | 1.8 | 3.75 |
| #41 | 1.15 | 3.2 |

As shown in Table 9, the stabilization ratios obtained with C terminus fusion proteins was much higher that N terminus fusion proteins. Construct #2 however did show modest ligand dependent stabilization when appended to the N terminus of the protein of interest. These data show that the ability of a particular DD mutant to stabilize or destabilize a protein of interest may depend on the positioning of the DD with respect to the protein.

Example 11

Response of PDE5A-Derived Destabilizing Domains to Vardenafil, Tadalafil and Sildenafil Mutations were created in PDE5A (535-860) catalytic domain using site directed mutagenesis and the mutants were cloned as AcGFP fusion into pELNS vector carrying mCherry marker and packaged in lentiviral vectors. HCT116 cells were transduced with the constructs and stable integrants were selected by cell sorting using mCherry marker. Cells were treated with vehicle (dimethyl sulfoxide, DMSO) or 10 µM Vardenafil (VDF) for 48 hours. Following the treatment, cells were analyzed for GFP expression using FACS. Basal expression was calculated as the ratio of GFP signal in the absence of ligand for a given cell line to auto fluorescence of parental HCT-116 cells. Stabilization ratio was calculated as the ratio of the GFP signal observed in the presence of stabilizing ligand to the signal from the same cell line in the absence of ligand. The results are provided in Table 10.

TABLE 10

Response to Vardenafil

| Construct | Basal (DMSO/Parental) | Stabilization ratio |
|---|---|---|
| PDE5AN (#53) | 14.0 | 6.1 |
| PDE5AC (#13) | 11.3 | 7.0 |
| PDE5AC (#25) | 7.1 | 10.1 |
| PDE5AC (#28) | 10.4 | 6.5 |
| PDE5AC (#42) | 20.0 | 6.0 |
| PDE5AC (#43) | 8.7 | 7.4 |
| PDE5AC (#69) | 6.5 | 6.8 |

As shown in Table 10, PDE5AC (#25), PDE5AC (#28), PDE5AC (#42), and PDE5AC (#43) showed stabilization ratios with Vardenafil that were greater than the stabilization ratios obtained with sildenafil in similar experiments (see Table 2 and Table 6), indicating that Vardenafil stabilization of PDE5A DDs is more potent that sildenafil. For PDE5AN (#3) PDE5AN (#53), PDE5AC (#13) and PDE5AC (#69), stabilization ratios similar to those observed for sildenafil were obtained (see Table 2 and Table 6) indicating that these PDE5A DDs may be stabilized by multiple ligands. All mutants tested also showed some basal expression in the absence of ligand. PDE5AC (#69) and PDE5AC (#25) showed the lowest basal expression levels among the mutants tested.

HCT 116 cells transduced with the PDE5A DD derived GFP constructs were also tested with increasing doses of Vardenafil. The HCT116 cells were incubated for 48 hours with Vardenafil starting at a dose of 0.002 µM to 30 µM. The GFP intensity of the Vardenafil treated samples was compared to the parental untransduced HCT116 and DMSO treated cells for each construct. The mean fluorescence intensity was calculated for each sample and used to calculate the stabilization ratios as well as the basal expression for each construct. The GFP expression was measured using flow cytometry and the mean fluorescence intensity (MFI) was calculated for each sample. The MFI values are shown in Table 11 and Table 12. The stabilization ratios are shown in Table 13 and Table 14 and the basal expression is show in Table 15.

TABLE 11

Response to Vardenafil

| Vardenafil (µM) | PDE5AN (#3) | PDE5AN (#53) | PDE5AC (#13) | PDE5AC (#25) |
|---|---|---|---|---|
| DMSO | 8934 | 14196 | 14659 | 9555 |
| 0.002 | 8767 | 14117 | 18393 | 9737 |
| 0.005 | 9620 | 14485 | 27661 | 9694 |
| 0.014 | 10487 | 15735 | 59673 | 9767 |
| 0.041 | 14086 | 17260 | 78117 | 10468 |
| 0.123 | 20568 | 25577 | 88571 | 13348 |
| 0.370 | 36786 | 43744 | 99160 | 20522 |
| 1.111 | 66543 | 81455 | 99377 | 38958 |
| 3.333 | 98986 | 131016 | 105500 | 66337 |
| 10 | 119591 | 173576 | 97493 | 94642 |
| 30 | 131667 | 188519 | 105335 | 120927 |

TABLE 12

Response to Vardenafil

| Vardenafil (µM) | PDE5AC (#28) | PDE5AC (#42) | PDE5AC (#43) | PDE5AC (#69) |
|---|---|---|---|---|
| DMSO | 13817 | 25111 | 12047 | 9466 |
| 0.002 | 15437 | 25236 | 13329 | 10817 |
| 0.005 | 19446 | 28309 | 17702 | 13682 |
| 0.014 | 29314 | 33958 | 33483 | 27457 |
| 0.041 | 45804 | 46882 | 55300 | 32264 |
| 0.123 | 74153 | 81233 | 70385 | 49884 |
| 0.370 | 81663 | 114847 | 78215 | 74730 |
| 1.111 | 89426 | 136303 | 83052 | 62065 |
| 3.333 | 92290 | 147512 | 88707 | 66625 |
| 10 | 86985 | 161587 | 85867 | 64380 |
| 30 | 93145 | 199877 | 86318 | 22775 |

TABLE 13

Stabilization ratio with Vardenafil

| Vardenafil (µM) | PDE5AN (#3) | PDE5AN (#53) | PDE5AC (#13) | PDE5AC (#25) |
|---|---|---|---|---|
| DMSO | — | — | — | — |
| 0.002 | 1.0 | 1.0 | 1.3 | 1.0 |
| 0.005 | 1.1 | 1.0 | 1.9 | 1.0 |
| 0.014 | 1.2 | 1.1 | 4.1 | 1.0 |
| 0.041 | 1.6 | 1.2 | 5.3 | 1.1 |
| 0.123 | 2.3 | 1.8 | 6.0 | 1.4 |

TABLE 13-continued

Stabilization ratio with Vardenafil

| Vardenafil (µM) | PDE5AN (#3) | PDE5AN (#53) | PDE5AC (#13) | PDE5AC (#25) |
|---|---|---|---|---|
| 0.370 | 4.1 | 3.1 | 6.8 | 2.1 |
| 1.111 | 7.4 | 5.7 | 6.8 | 4.1 |
| 3.333 | 11.1 | 9.2 | 7.2 | 6.9 |
| 10 | 13.4 | 12.2 | 6.7 | 9.9 |
| 30 | 14.7 | 13.3 | 7.2 | 12.7 |

TABLE 14

Stabilization ratio with Vardenafil

| Vardenafil (µM) | PDE5AC (#28) | PDE5AC (#42) | PDE5AC (#43) | PDE5AC (#69) |
|---|---|---|---|---|
| DMSO | — | — | — | — |
| 0.002 | 1.1 | 1.0 | 1.1 | 1.1 |
| 0.005 | 1.4 | 1.1 | 1.5 | 1.4 |
| 0.014 | 2.1 | 1.4 | 2.8 | 2.9 |
| 0.041 | 3.3 | 1.9 | 4.6 | 3.4 |
| 0.123 | 5.4 | 3.2 | 5.8 | 5.3 |
| 0.370 | 5.9 | 4.6 | 6.5 | 7.9 |
| 1.111 | 6.5 | 5.4 | 6.9 | 6.6 |
| 3.333 | 6.7 | 5.9 | 7.4 | 7.0 |
| 10 | 6.3 | 6.4 | 7.1 | 6.8 |
| 30 | 6.7 | 8.0 | 7.2 | 2.4 |

TABLE 15

Basal expression with Vardenafil

| Construct | MFI (with DMSO) | Basal |
|---|---|---|
| Parental | 1954 | — |
| PDE5AN (#3) | 8934 | 4.57 |
| PDE5AN (#53) | 14196 | 7.27 |
| PDE5AC (#13) | 14659 | 7.50 |
| PDE5AC (#25) | 9555 | 4.89 |
| PDE5AC (#28) | 13817 | 7.07 |
| PDE5AC (#42) | 25111 | 12.85 |
| PDE5AC (#43) | 12047 | 6.17 |
| PDE5AC (#69) | 9466 | 4.84 |

All mutants tested showed a dose dependent increase in the expression of GFP. As shown in Table 13 and Table 14, PDE5AC (#13), PDE5AN (#3), PDE5AC (#28), PDE5AC (#42) PDE5AC (#43), and PDE5AC (#69) showed ligand dependent stabilization with as little as 0.005 µM Vardenafil, as indicated by the greater than 1 stabilization ratios obtained with those constructs. PDE5AN (#3) showed the highest stabilization ratio at maximum ligand dose of 30 µM indicating that this construct showed maximum ligand dependent stabilization among the constructs tested. As shown in Table 15, the lowest basal expression was obtained with PDE5AN (#3) which was also the construct that showed the highest stabilization ratio at highest concentration of ligand tested. These data indicate that PDE5AN (#3) has the largest dynamic range among the constructs tested with Vardenafil.

PDE5AN (#3) was cloned as AcGFP fusion into pELNS vector carrying mCherry marker and packaged in lentiviral vectors. HCT116 cells were transduced with the construct and stable integrants were selected by cell sorting using mCherry marker. Cells were treated with vehicle (dimethyl sulfoxide, DMSO) or varying doses of Tadalafil (TDF) for 48 hrs with doses ranging from 0.01 µM to 100 µM. Following the treatment, cells were analyzed for GFP expression using FACS. Basal expression was calculated as the ratio of GFP signal in the absence of ligand for a given cell line to auto fluorescence of parental HCT-116 cells. Stabilization ratio was calculated as the ratio of the GFP signal observed in the presence of stabilizing ligand to the signal from the same cell line in the absence of ligand. The results are provided in Table 16.

TABLE 16

Response to Tadalafil

| Tadalafil (µM) | MFI | Stabilization ratio |
|---|---|---|
| Parental | 1175 | — |
| DMSO | 6944 | — |
| 0.01 | 6781 | 1.0 |
| 0.02 | 6685 | 1.0 |
| 0.05 | 7013 | 1.0 |
| 0.14 | 6988 | 1.0 |
| 0.41 | 7648 | 1.1 |
| 1.23 | 8973 | 1.3 |
| 3.7 | 14097 | 2.0 |
| 11.11 | 26560 | 3.8 |
| 33.33 | 49889 | 7.2 |
| 100 | 68532 | 9.9 |

As shown in Table 16, PDE5AN (#3), a Tadalafil dose dependent increase in the MFI was observed. Stabilization ratios greater than 1 were obtained with Tadalafil at concentrations greater than 0.41 (µM), indicating ligand dependent stabilization of PDE5AN (#3) with sub micromolar concentrations of Tadalafil.

HCT 116 cells transduced with the PDE5A DD derived GFP constructs were also tested with increasing doses of Tadalafil. The HCT116 cells were incubated for 48 hours with Tadalafil starting at dose 0.01 µM to 100 µM. The GFP intensity of the Tadalafil treated samples was compared to the parental untransduced HCT116 and DMSO treated cells for each construct. The mean fluorescence intensity was calculated for each sample and used to calculate the stabilization ratios as well as the basal expression for each construct. The MFI values are shown in Table 17 and Table 18. The stabilization ratios are shown in Table 19 and Table 20 and the basal expression is show in Table 21.

TABLE 17

Response to Tadalafil

| Tadalafil (µM) | PDE5AN (#53) | PDE5AC (#13) | PDE5AC (#25) |
|---|---|---|---|
| DMSO | 12071 | 14416 | 9297 |
| 0.01 | 11635 | 14388 | 9233 |
| 0.02 | 11690 | 14908 | 8860 |
| 0.05 | 12100 | 16488 | 9404 |
| 0.14 | 12331 | 21292 | 9478 |
| 0.41 | 13422 | 33396 | 9858 |
| 1.23 | 16255 | 58867 | 12432 |
| 3.7 | 24201 | 81755 | 19294 |
| 11.11 | 42644 | 92484 | 31763 |
| 33.33 | 80088 | 96959 | 54151 |
| 100 | 104032 | 105048 | 70389 |

TABLE 18

Response to Tadalafil

| Tadalafil (μM) | PDE5AC (#28) | PDE5AC (#42) | PDE5AC (#43) | PDE5AC (#69) |
|---|---|---|---|---|
| DMSO | 15004 | 22601 | 10998 | 8822 |
| 0.01 | 14073 | 22787 | 11444 | 9337 |
| 0.02 | 14513 | 23274 | 11479 | 10353 |
| 0.05 | 15730 | 23278 | 11764 | 12365 |
| 0.14 | 18316 | 24532 | 13429 | 19039 |
| 0.41 | 28462 | 26765 | 18940 | 32821 |
| 1.23 | 44739 | 35325 | 32204 | 52033 |
| 3.7 | 69430 | 59821 | 49646 | 62558 |
| 11.11 | 85998 | 92400 | 64186 | 69440 |
| 33.33 | 95189 | 122658 | 74446 | 68289 |
| 100 | 97016 | 139002 | 76281 | 67259 |

TABLE 19

Stabilization ratio with Tadalafil

| Tadalafil (μM) | PDE5AN (#53) | PDE5AC (#13) | PDE5AC (#25) |
|---|---|---|---|
| DMSO | — | — | — |
| 0.01 | 1.0 | 1.0 | 1.0 |
| 0.02 | 1.0 | 1.0 | 1.0 |
| 0.05 | 1.0 | 1.1 | 1.0 |
| 0.14 | 1.0 | 1.5 | 1.0 |
| 0.41 | 1.1 | 2.3 | 1.1 |
| 1.23 | 1.3 | 4.1 | 1.3 |
| 3.7 | 2.0 | 5.7 | 2.1 |
| 11.11 | 3.5 | 6.4 | 3.4 |
| 33.33 | 6.6 | 6.7 | 5.8 |
| 100 | 8.6 | 7.3 | 7.6 |

TABLE 20

Stabilization ratio with Tadalafil

| Tadalafil (μM) | PDE5AC (#28) | PDE5AC (#42) | PDE5AC (#43) | PDE5AC (#69) |
|---|---|---|---|---|
| DMSO | — | — | — | — |
| 0.01 | 0.9 | 1.0 | 1.0 | 1.1 |
| 0.02 | 1.0 | 1.0 | 1.0 | 1.2 |
| 0.05 | 1.0 | 1.0 | 1.1 | 1.4 |
| 0.14 | 1.2 | 1.1 | 1.2 | 2.2 |
| 0.41 | 1.9 | 1.2 | 1.7 | 3.7 |
| 1.23 | 3.0 | 1.6 | 2.9 | 5.9 |
| 3.7 | 4.6 | 2.6 | 4.5 | 7.1 |
| 11.11 | 5.7 | 4.1 | 5.8 | 7.9 |
| 33.33 | 6.3 | 5.4 | 6.8 | 7.7 |
| 100 | 6.5 | 6.2 | 6.9 | 7.6 |

TABLE 21

Basal expression with Tadalafil

| Tadalafil (μM) | MFI (with DMSO) | Basal Expression |
|---|---|---|
| Parental | 1280 | — |
| PDE5AN (#53) | 12071 | 9.43 |
| PDE5AC (#13) | 14416 | 11.26 |
| PDE5AC (#25) | 9297 | 7.26 |
| PDE5AC (#28) | 15004 | 11.72 |
| PDE5AC (#42) | 22601 | 17.66 |
| PDE5AC (#43) | 10998 | 8.59 |
| PDE5AC (#69) | 8822 | 6.89 |

All mutants tested showed a dose dependent increase in the expression of GFP. As shown in Table 19 and Table 20, PDE5AC (#13), and PDE5AC (#69) showed ligand dependent stabilization with as little as 0.14 μM Tadalafil, as indicated by the greater than 1.5 stabilization ratios obtained with those constructs. PDE5AN (#25) and PDE5AC (#69) showed the highest stabilization ratio at maximum ligand dose of 100 μM indicating that this construct showed maximum ligand dependent stabilization among the constructs tested. As shown in Table 21, the lowest basal expression was obtained with PDE5AC (#69) which was also one of the constructs that showed the highest stabilization ratio at highest concentration of ligand tested. These data indicate that PDE5AC (#69) has the largest dynamic range among the constructs tested with Tadalafil.

Similar experiments were performed in HCT116 cells using sildenafil. The above-mentioned DDs were cloned as AcGFP fusion into pELNS vector carrying mCherry marker and packaged in lentiviral vectors. HCT116 cells were transduced with the constructs and stable integrants were selected by cell sorting using mCherry marker. Cells were treated with sildenafil at the following μM concentrations: 0.01, 0.02, 0.05, 0.14, 0.41, 1.23, 3.7, 11.11, 33.33, and 100 for a duration of 48 hours. The fluorescence was analyzed by flow cytometry and the mean fluorescence intensity was calculated for all samples. All clones tested showed a dose dependent increase in expression. PDE5AC (#28) showed the highest MFI values upon treatment with 100 μM sildenafil. The MFI values are shown in Table 22 and Table 23. The stabilization ratios are shown in Table 24 and Table 25 and the basal expression is show in Table 26.

TABLE 22

Response to Sildenafil

| Sildenafil (μM) | PDE5AN (#3) | PDE5AN (#53) | PDE5AC (#13) | PDE5AC (#25) |
|---|---|---|---|---|
| DMSO | 9835 | 13747 | 15122 | 10217 |
| 0.01 | 9888 | 12801 | 14787 | 10169 |
| 0.02 | 10157 | 14045 | 17318 | 9354 |
| 0.05 | 9952 | 13801 | 26905 | 10120 |
| 0.14 | 10475 | 14048 | 48611 | 10128 |
| 0.41 | 12302 | 16175 | 69042 | 10207 |
| 1.23 | 16826 | 20410 | 84772 | 12328 |
| 3.70 | 27542 | 30372 | 82519 | 17466 |
| 11.11 | 52641 | 59723 | 92732 | 26947 |
| 33.33 | 85509 | 99558 | 93336 | 46897 |
| 100.00 | 103938 | 117792 | 76090 | 51774 |

TABLE 23

Response to Sildenafil

| Sildenafil (μM) | PDE5AC (#28) | PDE5AC (#42) | PDE5AC (#43) | PDE5AC (#69) |
|---|---|---|---|---|
| DMSO | 13208 | 23943 | 11147 | 9575 |
| 0.01 | 14613 | 23295 | 11962 | 9574 |
| 0.02 | 16502 | 23606 | 11940 | 11755 |
| 0.05 | 17801 | 24817 | 15203 | 11944 |
| 0.14 | 26694 | 29495 | 24319 | 19733 |
| 0.41 | 43862 | 40817 | 40470 | 30090 |
| 1.23 | 65762 | 63410 | 57723 | 44180 |
| 3.70 | 83657 | 91798 | 73400 | 52782 |
| 11.11 | 80269 | 127187 | 76900 | 59723 |
| 33.33 | 83663 | 149906 | 94863 | 65183 |
| 100.00 | 80213 | 164269 | 56552 | 51774 |

TABLE 24

Stabilization ratio with Sildenafil

| Sildenafil (μM) | PDE5AN (#3) | PDE5AN (#53) | PDE5AC (#13) | PDE5AC (#25) |
|---|---|---|---|---|
| DMSO | — | — | — | — |
| 0.01 | 1.0 | 0.9 | 1.0 | 1.0 |
| 0.02 | 1.0 | 1.0 | 1.1 | 0.9 |
| 0.05 | 1.0 | 1.0 | 1.8 | 1.0 |
| 0.14 | 1.1 | 1.0 | 3.2 | 1.0 |
| 0.41 | 1.3 | 1.2 | 4.6 | 1.0 |
| 1.23 | 1.7 | 1.5 | 5.6 | 1.2 |
| 3.70 | 2.8 | 2.2 | 5.5 | 1.7 |
| 11.11 | 5.4 | 4.3 | 6.1 | 2.6 |
| 33.33 | 8.7 | 7.2 | 6.2 | 4.6 |
| 100.00 | 10.6 | 8.6 | 5.0 | 5.1 |

TABLE 25

Stabilization ratio with Sildenafil

| Sildenafil (μM) | PDE5AC (#28) | PDE5AC (#42) | PDE5AC (#43) | PDE5AC (#69) |
|---|---|---|---|---|
| DMSO | — | — | — | — |
| 0.01 | 1.1 | 1.0 | 1.1 | 1.0 |
| 0.02 | 1.2 | 1.0 | 1.1 | 1.2 |
| 0.05 | 1.3 | 1.0 | 1.4 | 1.2 |
| 0.14 | 2.0 | 1.2 | 2.2 | 2.1 |
| 0.41 | 3.3 | 1.7 | 3.6 | 3.1 |
| 1.23 | 5.0 | 2.6 | 5.2 | 4.6 |
| 3.70 | 6.3 | 3.8 | 6.6 | 5.5 |
| 11.11 | 6.1 | 5.3 | 6.9 | 6.2 |
| 33.33 | 6.3 | 6.3 | 8.5 | 6.8 |
| 100.00 | 6.1 | 6.9 | 5.1 | 5.4 |

TABLE 26

Basal expression with Sildenafil

| Description | MFI (with DMSO) | Basal expression |
|---|---|---|
| Parental | 1287 | — |
| PDE5AN (#3) | 9835 | 7.6 |
| PDE5AN (#53) | 13747 | 10.7 |
| PDE5AC (#13) | 15122 | 11.7 |
| PDE5AC (#25) | 10217 | 7.9 |
| PDE5AC (#28) | 13208 | 10.3 |
| PDE5AC (#42) | 23943 | 18.6 |
| PDE5AC (#43) | 11147 | 8.7 |
| PDE5AC (#69) | 9575 | 7.4 |

All mutants tested showed a dose dependent increase in the expression of GFP. As shown in Table 22 and Table 23, PDE5AC (#13), showed ligand dependent stabilization with as little as 0.05 μM Sildenafil, as indicated by the greater than 1.5 stabilization ratios obtained with that construct. PDE5AN (#28), PDE5AC (#43) and PDE5AC (#69) showed stabilization ratios greater than 1.5 with 0.14 μM of Sildenafil. PDE5AN (#3) showed the highest stabilization ratio at maximum ligand dose of 100 μM indicating that this construct showed maximum ligand dependent stabilization among the constructs tested. As shown in Table 26, the lowest basal expression was obtained with PDE5AC (#69). These data indicate that the PDE5A DDs described herein can be stabilized by multiple ligands.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A conditional protein stability system, comprising:
   a nucleic acid sequence encoding a fusion protein comprising a protein of interest fused in-frame to a single-protein, ligand dependent destabilizing domain wherein the ligand dependent destabilizing domain comprises SEQ ID NO: 19 (encoded by SEQ ID NO: 36); and
   a ligand, wherein the ligand is Sildenafil or Vardenafil,
   wherein upon introduction of the nucleic acid sequence to a cell,
   the fusion protein is expressed, and
   wherein degradation of the protein of interest is decreased upon administration of the ligand.

2. The conditional protein stability system of claim 1, wherein the ligand dependent destabilizing domain consists of SEQ ID NO: 19 (encoded by SEQ ID NO: 36).

* * * * *